United States Patent
Sørensen et al.

(10) Patent No.: US 6,521,606 B2
(45) Date of Patent: Feb. 18, 2003

(54) MATRIX METALLOPROTEINASE INHIBITORS

(75) Inventors: Morten Dahl Sørensen, Hørsholm (DK); Lars Kristian Albert Blæhr, København (DK); Mette Knak Christensen, Holte (DK)

(73) Assignee: Leo Pharmaceutical Products, Ltd. A/S, Ballerup (DK)

( * ) Notice: Subject to any disclaimer, the term of this patent is extended or adjusted under 35 U.S.C. 154(b) by 21 days.

(21) Appl. No.: 09/899,017

(22) Filed: Jul. 6, 2001

(65) Prior Publication Data
US 2002/0103166 A1 Aug. 1, 2002

Related U.S. Application Data

(60) Provisional application No. 60/219,031, filed on Jul. 18, 2000.

(51) Int. Cl.$^7$ .............................. A61K 31/66; C07F 9/21
(52) U.S. Cl. .......................................... 514/105; 558/81
(58) Field of Search ............................ 558/81; 514/105

(56) References Cited

U.S. PATENT DOCUMENTS

| | | | | |
|---|---|---|---|---|
| 3,732,340 A | * | 5/1973 | Arnold et al. | 558/81 |
| 4,618,692 A | * | 10/1986 | Scheffler et al. | 558/81 |
| 4,684,742 A | * | 8/1987 | Stec et al. | 558/81 |
| 6,420,586 B1 | * | 7/2002 | Hanson et al. | 558/81 |

* cited by examiner

*Primary Examiner*—Deborah C. Lambkin

(57) ABSTRACT

A compound of the general formula I

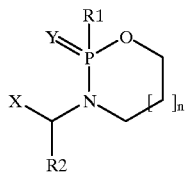

wherein Y is O or S;

n is 1, 2, 3 or 4;

X represents hydroxamic acid, carboxylic acid, phosphonic acid, acetylthiomethyl group or a mercaptomethyl group;

R1 is

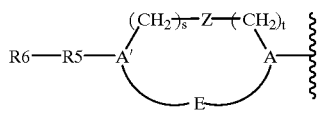

wherein E, when present represents, a bond or optionally substituted methylene or ethylene;

s and t are independently 0, 1, 2 or 3;

A and A' independently represent a bond, or a saturated or unsaturated, optionally substituted cyclic or heterocyclic hydrocarbon di- or triradical;

Z represents a bond, O, S, C(O), C(O)NR7, NR7C(O) or NR7, wherein R7 is hydrogen, hydroxy, branched or straight, saturated or unsaturated, optionally substituted hydrocarbon radical;

R5 represents a bond, alkane or alkene diradical, one or more ether diradicals (R—O—R') or amine diradicals (R—N—R'), wherein R and R' independently represent alkane or alkene diradicals with a C-content from 0 to 3;

R6 represents hydrogen, hydroxy, halogen, cyano, nitro, branched or straight, saturated or unsaturated, optionally substituted hydrocarbon radical, unsaturated optionally substituted cyclic or heterocyclic hydrocarbon radical, NR8R9, C(O)NR8R9, C(O)R8, CO(O)R8, S(O)$_2$R9, wherein each R8 and R9 independently represent hydrogen, halogen, a branched or straight, saturated or unsaturated, optionally substituted hydrocarbon radical;

R2 represents hydrogen, $(C_{1-8})$alkyl, $(C_{2-6})$alkenyl, $(C_{3-8})$cycloalkyl, aryl$(C_{0-6})$alkyl or heteroaryl$(C_{0-6})$alkyl;

provided that if A, A', Z and R5 are all bonds, and s and t are both 0 (zero), then R6 is different from hydrogen;

or a salt, hydrate or solvate thereof.

The compounds are valuable for human and veterinary therapy.

12 Claims, No Drawings

MATRIX METALLOPROTEINASE INHIBITORS

This application claims benefit of U.S. Ser. No. 60/219,031 filed Jul. 18, 2000.

The present invention relates to a hitherto unknown class of compounds comprising new matrix metalloproteinase inhibitors, which are 1,3,2-oxazaphos-phacycloalkane based hydroxamic acids, carboxylic acids, phosphonic acids or thiols, to pharmaceutical compositions containing said compounds, to methods of treating patients with said compounds, and to the use of such compounds in the preparation of medicine. In particular, the compounds are inhibitors of matrix metalloproteinases involved in tissue degradation. Some of the compounds of the invention are, in addition, inhibitors of the release of tumour necrosis factor-α (TNF-α) from cells.

BACKGROUND OF THE INVENTION

Matrix metalloproteinases (MMPs) are a family of zinc endopeptidases, which exhibit proteolytic activity towards most if not all of the constituents of the extra-cellular matrix, such as the interstitial and basement membrane collagens, fibro-nectin, and laminin. They play a key role in both physiological and pathological tissue degradation.

At least 17 different and yet highly homologous MMP-species have been characterised. They share a catalytic domain with the VAAHEXGHXXGXXH motif responsible for ligating zinc, which is essential for the catalytic function. MMP family members differ from each other structurally by the presence or absence of additional domains that contribute to activities, such as substrate specificity, inhibitor binding, matrix binding and cell-surface localisation. [H. Birkedal-Hansen, W. G. Moore, M. K. Bodden, C. J. Windsor, B. Birkedal-Hansen, A. DeCarlo: *Crit. Rev. Oral Biol. Med.* (1993) 4, 197–250 and A. F. Chambers, L. M. Matristan: *J. Natl. Cancer Inst.* (1997) 89(17), 1260–1270]. There are three major groups of MMPs, identified by their substrate preferences: collagenases degrade fibrillar collagen, stromelysins prefer proteoglycans and glycoproteins as substrates and gelatinases are particularly potent in degradation of nonfibrillar and denatured collagens (gelatine).

MMPs are also believed to be important in the processing, or secretion, of biologically important cell mediators, such as TNF-α, and the post translational proteolysis processing, or shedding, of biologically important membrane proteins, such as the low affinity IgE receptor CD 23 (for a more complete list see N. M. Hooper et al.: *Biochem. J.* (1997) 321, 265–279).

Potential therapeutic indications of MMP inhibitors have been discussed in the literature [e.g. T. H. Vu, Z. Werb. (1998) (In: Matrix Metalloproteinases. 1998. Edited by W. C. Parks and R. P. Mecham. Pp115–148. Academic Press. ISBN 0-12-545090-7); D. E. Mullins et al.: *Biochem. Biophys. Acta* (1983) 695, 117–214; B. Henderson et al.: *Drugs of the Future* (1990) 15, 495–508; R. Reich et al.: *Cancer Res.* (1988) 48, 3307–3312]. Compounds which have the property of inhibiting the action of matrix metalloproteinases are thought to be potentially useful for, but not restricted to, the treatment or prophylaxis of conditions involving tissue breakdown and inflammation, for example rheumatoid arthritis, osteoarthritis, osteopenias such as osteoporosis, periodontitis, gingivitis, corneal epidermal or gastric ulceration, skin ageing and tumour metastasis, tumour invasion and tumour growth. MMP inhibitors are also of potential value in the treatment of neuroinflammatory disorders, including those involving myelin degradation, for example multiple sclerosis, as well as in the management of angiogenesis dependent diseases, which include arthritic conditions and solid tumour growth as well as psoriasis, proliferative retinopathies, neovascular glaucoma, ocular tumours, angio fibromas and hemangiomas. However, the relative contributions of individual MMPs in any of the above disease states is not yet fully understood.

TNF-α is a cytokine which is produced as a 28-kDa precursor and released in an active 17-kDa form. This active form can mediate a large number of deleterious effects in vivo, including inflammation, fever, cardiovascular effects, haemorrhage, coagulation and acute phase responses, similar to those seen during acute infections and shock states. Chronic administration of TNF-α can cause cachexia and anorexia; accumulation of excess TNF-α can be fatal. Compounds which inhibit the production or action of TNF-α are therefore thought to be potentially useful for the treatment or prophylaxis of many inflammatory, infectious, immunological and malignant diseases. These include, but are not limited to, septic shock, haemodynamic shock and sepsis syndrome, post ischaemic reperfusion injury, Crohn's disease, mycobacterial infection, meningitis, psoriasis, congestive heart failure, cancer, rheumatoid arthritis and multiple sclerosis.

TNF-α convertase is a metalloprotease involved in the biosynthesis of TNF-α. Inhibition of TNF-α convertase inhibits production of TNF-α. Since excessive TNF-α production has been noted in several disease conditions characterised by MMP-mediated tissue degradation, including multiple sclerosis, arthritis and cancer, compounds which inhibit both MMPs and TNF-α production may have particular advantages in the treatment or prophylaxis of diseases or conditions in which both mechanisms are involved.

Many known MMP inhibitors are peptide derivatives, based on naturally occurring amino acids, and are analogues of the cleavage sites in the natural substrates of the MMPs. Other known MMP inhibitors are less peptidic in structure, and may be viewed as pseudopeptides or peptidomimetics, e.g. sulfonamides. Such compounds usually have a zinc binding group, which most often is a hydroxamic acid, reverse hydroxamic acid, carboxylic acid, sulphhydryl, and oxygenated phosphorous (e.g. phosphinic acid and phosphonamides including aminophosphonic acid) groups.

Although numerous MMP inhibitors with potent in vitro activities are known, many have not been suitable for further development as medicines, since they have lacked any useful activity when administered orally at pharmaceutically acceptably doses. Although it is known that a number of factors influence oral bioavailability, the design of enzyme inhibitors with high oral bioavailability is far from straightforward. Finding a series of compounds that permits a good balance of intrinsic level of activity, water solubility, oral absorption, and favourable pharmacokinetic properties is a continuing problem in the art, since those properties can vary in an unpredictable way in relation to the structure. Identifying MMP inhibitors having such properties remains a challenge.

Prior art has consisted of simple peptidic compounds as well as linear and cyclic sulfonamide compounds, e.g. EP-A-0489577, WO 96/16931, WO 96/33991, WO 97/44315 and WO 00/09485. Only a single example of a prior art patent publication exists depicting simple linear phosphinamide compounds [WO 98/08853]. These are structurally diverse from the cyclic compounds of general formula (I). Prior art has depicted only 1,3,2-oxazaphosphorocycloalkanes with simple phenyl and alkyl substituents, however they do not contain the requisite hydroxamic acid or other zinc binding groups (e.g. PL 149593, FR 2567129, *Izv. Akad. Nauk., Ser. Khim* (1995) (11), 2241–9). It has now surprisingly been found that the novel 1,3,2-oxazaphoshacycloalkane based compounds of general formula (I) of the present invention are potent MMP inhibitors. Preferred compounds of the present invention display nanomolar to micromolar potency in inhibiting MMPs, such as MMP-13, MMP-9 and MMP-3.

The present invention relates to a novel class of compounds of the general formula I

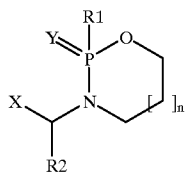

[I]

wherein Y is O or S;

n is 1, 2, 3 or 4;

X represents hydroxamic acid, carboxylic acid, phosphonic acid, acetylthiomethyl group or a mercaptomethyl group;

R1 is

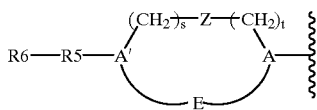

wherein E, when present represents, a bond or optionally substituted methylene or ethylene;

s and t are independently 0, 1, 2 or 3;

A and A' independently represent a bond, or a saturated or unsaturated, optionally substituted cyclic or heterocyclic hydrocarbon di- or triradical;

Z represents a bond, O, S, C(O), C(O)NR7, NR7C(O) or NR7, wherein R7 is hydrogen, hydroxy, branched or straight, saturated or unsaturated, optionally substituted hydrocarbon radical;

R5 represents a bond, alkane or alkene diradical, one or more ether diradicals (R—O—R') or amine diradicals (R—N—R'), wherein R and R' independently represent alkane or alkene diradicals with a C-content from 0 to 3;

R6 represents hydrogen, hydroxy, halogen, cyano, nitro, branched or straight, saturated or unsaturated, optionally substituted hydrocarbon radical, unsaturated optionally substituted cyclic or heterocyclic hydrocarbon radical, NR8R9, C(O)NR8R9, C(O)R8, CO(O)R8, S(O)$_2$R9, wherein each R8 and R9 independently represent hydrogen, halogen, a branched or straight, saturated or unsaturated, optionally substituted hydrocarbon radical;

R2 represents hydrogen, $(C_{1-8})$alkyl, $(C_{2-6})$alkenyl, $(C_{3-8})$cycloalkyl, aryl$(C_{0-6})$alkyl or heteroaryl$(C_{0-6})$alkyl;

provided that if A, A', Z and R5 are all bonds, and s and t are both 0 (zero), then R6 is different from hydrogen;

or a salt, hydrate or solvate thereof.

As used in the specification, unless specified to the contrary, the following terms have the meaning indicated:

"Alkyl" refers to a straight or branched chain alkyl moiety, consisting solely of carbon and hydrogen, containing no unsaturation and having the number of carbon atoms specified, including for example methyl, n-propyl, isobutyl, t-butyl, hexyl and dodecyl.

"$(C_2–C_6)$alkenyl" refers to a straight or branched chain alkenyl moiety having 2 to 6 carbon atoms having at least one double bond of either E or Z stereochemistry where applicable. This term would include, for example, vinyl, allyl, 1- and 2-butenyl and 2-methyl-2-propenyl.

The term "alkoxy" is intended to indicate a radical of formula OR, wherein R is alkyl as defined above, e.g. methoxy, ethoxy, propoxy, butoxy, etc.

The term "alkoxycarbonyl" is intended to indicate a radical of formula —COOR wherein R is alkyl as defined above, e.g. methoxycarbonyl, ethoxycabonyl, n-propoxycarbonyl, isopropoxycarbonyl, etc.

The term "saturated cyclic hydrocarbon" is intended to indicate cyclic compounds, optionally fused bicyclic rings, containing hydrogen and carbon, which are saturated, such as cyclopropane, cyclobutane, cyclopentane, cyclohexane, cycloheptane, cyclooctane, hydrindane and decaline.

The term "unsaturated cyclic hydrocarbon" is intended to indicate cyclic compounds, optionally fused bicyclic rings, containing hydrogen and carbon, in which one or more carbon-carbon bond is unsaturated, such as cyclopentene, cyclohexene, cyclohexadiene, cycloheptene, benzene, naphtene and 1,4-dihydronaphtene, indane and indene.

The term "heterocyclic hydrocarbon" is intended to indicate saturated or unsaturated cyclic compounds of hydrogen, carbon, and one or more heteroatoms selected from O, S, N and P, such as pyrrole, furan, thiophene, imidazole, oxazole, thiazole, pyrazole, pyrrolidine, pyridine, pyrimidine, tetrahydrotiophene, tetrahydrofuran, piperidine, piperazine, phosphalane, phosphorinane and phosporepane.

"Aryl" refers to phenyl or naphtyl.

"Cycloalkyl" means a saturated alicyclic moiety having from 3–8 carbon atoms and includes, for example, cyclopropyl, cyclopentyl, cyclohexyl, and cyclooctyl.

"Heteroaryl" refers to pyridyl, indolyl, thienyl or imidazolyl.

Unless otherwise specified in the context in which it occurs, the term "substituted" as applied to any moiety herein means substituted with up to four substituents, each of which independently may be a $(C_{1-6})$alkoxy, $(C_{1-6})$alkyl, phenyl, hydroxy, thio, $(C_{1-6})$alkylthio, amino, halo (including fluoro, chloro, bromo and iodo), cyano, cyanomethyl, trifluoromethyl, nitro, carboxy, —CONH$_2$, haloalkyl, alkylamino, hydroxyalkyl, alkylcarbonyl, —CONHR12 or —CONR12R12 wherein R12 is a $(C_1-C_6)$ alkyl group or the residue of a natural α-amino acid.

Salts of the compounds of the invention can be formed with bases. Such salts include salts derived from inorganic or organic bases, for example metal salts such as sodium or potassium salts, alkaline earth metal salts such as magnesium or calcium salts, and organic amine salts such as morpholine, piperidine, dimethylamine or diethylamine salts.

If the compounds of the invention contain basic moieties, salts may also be formed with pharmaceutically acceptable inorganic or organic acids, such as hydrochloric, hydrobromic, and hydroiodic acid, phosphoric acid, sulphuric acid, nitric acid, p-toluenesulphonic acid, methanesulphonic acid, formic acid, acetic acid, propionic acid, citric acid, tartaric acid, succinic acid, benzoic acid, maleic acid, these examples being considered as non-limiting for the invention.

There are chiral centres in the compounds according to the invention due to the presence of an asymmetric carbon atom and an asymmetric phosphorous atom. The presence of several chiral centres gives rise to a number of diastereoisomers with R or S stereochemistry at each chiral centre. Likewise, the occurrence of carbon-carbon double bonds and ringsystems gives rise to the presence of geometric and stereo isomeric forms. General formula (I), and (unless specified otherwise) all other formulae in this specification are to be understood to include all such isomers, in pure form, or as mixtures thereof.

In the compounds of the invention, the preferred stereochemistry is in general as follows:

C atom carrying the R2 group —(R), but mixtures in which the above configurations predominate are also contemplated. Without limiting the generality of the foregoing:

Preferred compounds of formula (I) are those in which X represents CONHOH. More preferred compounds of formula (I) are those in which X represents CONHOH, n=1 or 2 and Y represents oxygen.

In a preferred embodiment, R1 is selected from the group consisting of alkoxyphenyl, phenoxyphenyl optionally substituted with halogen, halogen substituted hydrocarbon radical or cyano, phenylalkyl or naphtylalkyl both optionally substituted with halogen, phenyl optionally substituted with halogen or nitro, hydrocarbon radical, biphenyl optionally substituted with halogen, benzylphenoxyl, phenyl—(NH)—C(O)—phenyl optionally substituted with halogen or cyano and methoxy.

Examples of particular R1 groups include 4-methoxyphenyl, 4-(4-chlorophenoxy)-phenyl, 4-(4-bromophenoxy)-phenyl, 4-(4-trifluoromethylphenoxy)-phenyl, 4'bromo-4-biphenylyl, N-(4-chlorbenzoyl)-4-aminophenyl, 4-nitrophenyl, N-benzoyl-4-aminophenyl, 4-phenoxyphenyl.

In a preferred embodiment, R2 is selected from the group consisting of hydrogen, $(C_{1-8})$alkyl, $(C_{2-6})$alkenyl and aryl $(C_{0-6})$alkyl.

Examples of particular R2 groups include hydrogen, isopropyl, allyl, isobutyl, n-butyl, n-octyl and benzyl.

Examples of the invention are:

(±)-2-(4-Chlorophenoxy)-2-oxo-1,3,2-oxazaphosphorinane-3-acetohydroxamic acid.

(±)-2-(4-Chlorophenoxy)-2-oxo-1,3,2-oxazaphosphorepane-3-acetohydroxamic acid.

(±)-2-[(4-Bromophenyl)methyl]-2-oxo-1,3,2-oxazaphosphorinane-3-acetohydroxamic acid.

(±)-2-[(4-Biphenylyl)methyl]-2-oxo-1,3,2-oxazaphosphorinane-3-acetohydroxamic acid.

(±)-2-(4-Biphenylyl)-2-oxo-1,3,2-oxazaphosphorinane-3-acetohydroxamic acid.

(±)-2-(4-Biphenylyl)-2-oxo-1,3,2-oxazaphosphorepane-3-acetohydroxamic acid.

(±)-2-Heptyl-2-oxo-1,3,2-oxazaphosphorinane-3-acetohydroxamic (±)-2-Heptyl-2-oxo-1,3,2-oxazaphosphorepane-3-acetohydroxamic acid.

(±)-2-Oxo-2-[4-(phenylamino)phenyl]-1,3,2-oxazaphosphorinane-3-acetohydroxamic acid.

(±)-2-Oxo-2-phenyl-1,3,2-oxazaphosphorinane-3-acetohydroxamic acid.

(±)-2-Oxo-2-phenyl-1,3,2-oxazaphosphorepane-3-acetohydroxamic acid.

(±)-2-Oxo-2-phenyl-1,3,2-oxazaphosphoronane-3-acetohydroxamic acid (±)-α-Butyl-2-oxo-2-phenyl-1,3,2-oxazaphosphorepane-3-acetohydroxamic acid.

(±)-α-Butyl-2-oxo-2-phenyl-1,3,2-oxazaphosphorepane-3-acetohydroxamic acid.

(±)-2-(4-Methoxyphenyl)-2-oxo-1,3,2-oxazaphosphorinane-3-acetohydroxamic acid.

(±)-2-(4-Methoxyphenyl)-2-oxo-1,3,2-oxazaphosphorepane-3-acetohydroxamic acid.

(±)-2-(4-Methoxyphenyl)-2-oxo-1,3,2-oxazaphosphoronane-3-acetohydroxamic acid.

(αR) -2-(4- Methoxyphenyl)-α-(1-methylethyl)-2-oxo-1,3,2-oxazaphosphorinane-3-acetohydroxamic acid (diastereomer 1).

(αR)-2-(4-Methoxyphenyl)-α-(1-methylethyl)-2-oxo-1,3,2-oxazaphosphorinane-3-acetohydroxamic acid (diastereomer 2).

(±)-α-Butyl-2-(4-methoxyphenyl)-2-oxo-1,3,2-oxazaphosphorinane-3-acetohydroxamic acid (diastereomers 1).

(±)-α-Butyl-2-(4-methoxyphenyl)-2-oxo-1,3,2-oxazaphosphorinane-3-acetohydroxamic acid (diastereomers 2).

(±)-α-Butyl-2-(4-methoxyphenyl)-2-oxo-1,3,2-oxazaphosphorepane-3-acetohydroxamic acid (diastereomers 1).

(±)-α-Butyl-2-(4-methoxyphenyl)-2-oxo-1,3,2-oxazaphosphorepane-3-acetohydroxamic acid (diastereomers 2).

(±)-α-Butyl-2-(4-methoxyphenyl)-2-oxo-1,3,2-oxazaphosphorocane-3-acetohydroxamic acid (diastereomers 1).

(±)-α-Butyl-2-(4-methoxyphenyl)-2-oxo-1,3,2-oxazaphosphorocane-3-acetohydroxamic acid (diastereomers 2).

(±)-α-Allyl-2-(4-methoxyphenyl)-2-oxo-1,3,2-oxazaphosphorinane-3-acetohydroxamic acid (diastereomers 1).

(±)-α-Allyl-2-(4-methoxyphenyl)-2-oxo-1,3,2-oxazaphosphorinane-3-acetohydroxamic acid (diastereomers 2,).

(±)-α-Allyl-2-(4-methoxyphenyl)-2-oxo-1,3,2-oxazaphosphorepane-3-acetohydroxamic acid (diastereomers 1,).

(±)-α-Allyl-2-(4-methoxyphenyl)-2-oxo-1,3,2-oxazaphosphorepane-3-acetohydroxamic acid (diastereomers 2).

(αR)-2-(4-Methoxyphenyl)-α-(2-methylpropyl)-2-oxo-1,3,2-oxazaphosphorinane-3-acetohydroxamic acid (diastereomer 1, compound 130).

(αR)-2-(4-Methoxyphenyl)-α-(2-methylpropyl)-2-oxo-1,3,2-oxazaphosphorinane-3-acetohydroxamic acid (diastereomer 2).

(αS)-2-(4-Methoxyphenyl)-α-(2-methylpropyl)-2-oxo-1,3,2-oxazaphosphorinane-3-acetohydroxamic acid (diastereomer 1).

(αS)-2-(4-Methoxyphenyl)-α-(2-methylpropyl)-2-oxo-1,3,2-oxazaphosphorinane-3-acetohydroxamic acid (diastereomer 2).

(±)-2-(4-Methoxyphenyl)-α-(2-methylpropyl)-2-oxo-1,3,2-oxazaphosphorepane-3-acetohydroxamic acid (diastereomers 1).

(±)-2-(4-Methoxyphenyl)-α-(2-methylpropyl)-2-oxo-1,3,2-oxazaphosphorepane-3-acetohydroxamic acid (diastereomers 2).

(±)-2-(4-Methoxyphenyl)-α-propyl-2-oxo-1,3,2-oxazaphosphorinane-3-acetohydroxamic acid (diastereomers 1).

(±)-2-(4-Methoxyphenyl)-α-propyl-2-oxo-1,3,2-oxazaphosphorinane-3-acetohydroxamic acid (diastereomers 2,).

(±)-2-(4-Methoxyphenyl)-α-octyl-2-oxo-1,3,2-oxazaphosphorepane-3-acetohydroxamic acid (diastereomers 1).

(±)-2-(4-Methoxyphenyl)-α-octyl-2-oxo-1,3,2-oxazaphosphorepane-3-acetohydroxamic acid (diastereomers 2,).

(αR)-2-(4-Methoxyphenyl)-2-oxo-α-phenylmethyl-1,3,2-oxazaphosphorinane-3-acetohydroxamic acid (diastereomer 1).

(αS)-2-(4-Methoxyphenyl)-2-oxo-α-phenylmethyl-1,3,2-oxazaphosphorinane-3-acetohydroxamic acid (diastereomer 1).

(αS)-2-(4-Methoxyphenyl)-2-oxo-α-phenylmethyl-1,3,2-oxazaphosphorinane-3-acetohydroxamic acid (diastereomer 2).

(±)-2-Oxo-2-(4-phenoxyphenyl)-1,3,2-oxazaphosphorinane-3-acetohydroxamic acid.

(±)-2-Oxo-2-(4-phenoxyphenyl)-1,3,2-oxazaphosphorepane-3-acetohydroxamic acid.

(±)-2-Oxo-2-(4-phenoxyphenyl)-1,3,2-oxazaphosphorocane-3-acetohydroxamic acid.

(±)-α-Allyl-2-oxo-2-(4-phenoxyphenyl)-1,3,2-oxazaphosphorinane-3-acetohydroxamic acid (diastereomers 1.).

(±)-α-Allyl-2-oxo-2-(4-phenoxyphenyl)-1,3,2-oxazaphosphorinane-3-acetohydroxamic acid (diastereomers 2).

(αR)-α-(2-Methylpropyl)-2-oxo-2-(4-phenoxyphenyl)-1,3,2-oxazaphosphorinane-3-acetohydroxamic acid (diastereomer 1).

(αR)-α-(2-Methylpropyl)-2-oxo-2-(4-phenoxyphenyl)-1,3,2-oxazaphosphorinane-3-acetohydroxamic acid (diastereomer 2).

(αR)-α-(2-Methylethyl)-2-oxo-2-(4-phenoxyphenyl)-1,3,2-oxazaphosphorinane-3-acetohydroxamic acid (diastereomer 1).

(αR)-α-(2-Methylethyl)-2-oxo-2-(4-phenoxyphenyl)-1,3,2-oxazaphosphorinane-3-acetohydroxamic acid (diastereomer 2).

(±)-α-Butyl-2-oxo-2-(4-phenoxyphenyl)-1,3,2-oxazaphosphorepane-3-acetohydroxamic acid (diastereomers 1).

(±)-α-Butyl-2-oxo-2-(4-phenoxyphenyl)-1,3,2-oxazaphosphorepane-3-acetohydroxamic acid (diastereomers 2).

±)-α-Octyl-2-oxo-2-(4-phenoxyphenyl)- 1,3,2-oxazaphosphorepane-3-acetohydroxamic acid (diastereomers 1).

(±)-α-Octyl-2-oxo-2-(4-phenoxyphenyl)-1,3,2-oxazaphosphorepane-3-acetohydroxamic acid (diastereomers 2).

(±)-2-Oxo-2-(2-phenylethyl)-1,3,2-oxazaphosphorinane-3-acetohydroxamic acid.

(±)-2-(4-Methoxyphenyl)-2-oxo-1,3,2-oxazaphosphorocane-3-acetohydroxamic acid.

(±)-2-Oxo-2-phenyl-1,3,2-oxazaphosphorocane-3-acetohydroxamic acid.

(±)-2-Heptyl-2-oxo-1,3,2-oxazaphosphorocane-3-acetohydroxamic acid (compound 159).

(αR)-2-(4-Biphenylyl)-α-(1-methylethyl)-2-oxo-1,3,2-oxazaphosphorinane-3-acetohydroxamic acid (diastereomer 2).

(±)-2-[4-(4-Chlorophenyloxy)-phenyl]-2-oxo-1,3,2-oxazaphosphorepane-3-acetohydroxamic acid.

(±)-2-[4-(4-Chlorophenyloxy)-phenyl]-2-oxo-1,3,2-oxazaphosphorocane-3-acetohydroxamic acid.

(αR)-2-[4-(4-Chlorophenyloxy)-phenyl]-α-(2-methylethyl)-2-oxo-1,3,2-oxazaphosphorinane-3-acetohydroxamic acid.

(±)-2-(4'-Bromo-4-biphenylyl)-2-oxo-1,3,2-oxazaphosphorinane-3-acetohydroxamic acid.

(±)-2-(4'-Bromo-4-biphenylyl)-2-oxo-1,3,2-oxazaphosphorepane-3-acetohydroxamic acid.

(±)-2-(4'-Bromo-4-biphenylyl)-2-oxo-1,3,2-oxazaphosphorocane-3-acetohydroxamic acid.

(±)- 2-[2-(1-Naphtyl)-ethyl]-2-oxo-1,3,2-oxazaphosphorinane-3-acetohydroxamic acid.

(±)-2-Phenyl-2-thioxo-1,3,2-oxazaphosphorinane-3-acetohydroxamic acid.

(±)-2-Phenyl-2-thioxo-1,3,2-oxazaphosphorepane-3-acetamide.

(±)-2-Phenyl-2-thioxo-1,3,2-oxazaphosphorocane-3-acetamide.

(±)-2-[4-(4-Chlorophenyloxy)-phenyl]-2-oxo-1,3,2-oxazaphosphorinane-3-acetohydroxamic acid.

(±)-2-(4-Bromophenyl)-2-oxo-1,3,2-oxazaphosphorinane-3-acetohydroxamic acid.

(±)-2-(4-Bromophenyl)-2-oxo-1,3,2-oxazaphosphorepane-3-acetohydroxamic acid.

(±)-2-Oxo-2-(4-phenylmethoxyphenyl)-1,3,2-oxazaphosphorinane-3-acetohydroxamic acid.

(±)-2-Oxo-2-(4-phenylmethoxyphenyl)-1,3,2-oxazaphosphorepane-3-acetohydroxamic acid.

(±)-2-Oxo-2-(4-phenylmethoxyphenyl)-1,3,2-oxazaphosphorocane-3-acetohydroxamic acid.

(±)-2-[2-(4-Chlorophenoxy)-phenyl ]-2-oxo-1,3,2-oxazaphosphorepane-3-acetohydroxamic acid (±)-2-Oxo-2-[4-(4-trifluoromethylphenoxy)-phenyl]-1,3,2-oxazaphosphorinane-3-acetohydroxamic acid.

(±)-2-Oxo-2-[4-(4-trifluoromethylphenoxy)-phenyl]-1,3,2-oxazaphosphorepane-3-acetohydroxamic acid.

(αR)-α-(2-Methylethyl)-2-oxo-2-[4-(4-trifluoromethylphenoxy)-phenyl]-1,3,2-oxazaphosphorinane-3-acetohydroxamic acid (diastereomer 1,).

(αR)-α-(2-Methylethyl)-2-oxo-2-[4-(4-trifluoromethylphenoxy)-phenyl]-1,3,2-oxazaphosphorinane-3-acetohydroxamic acid (diastereomer 2).

(±)-2-[4-(4-Bromophenoxy)-phenyl]-2-oxo-1,3,2-oxazaphosphorinane-3-acetohydroxamic acid.

(±)-2-[4-(4-Bromophenoxy)-phenyl]-2-oxo-1,3,2-oxazaphosphorepane-3-acetohydroxamic acid.

(±)-2-(4-nitrophenyl)-2-oxo-1,3,2-oxazaphosphorepane-3-acetohydroxamic acid (±)-2-[N-(4-Chlorobenzoyl)-4-aminophenyl]-2-oxo-1,3,2-oxazaphosphorepane-3-acetohydroxamic acid.

(±)-2-(N-Benzoyl-4-aminophenyl-2-oxo-1,3,2-oxazaphosphorepane-3-acetohydroxamic acid;

and the corresponding carboxylic acids.

The compounds of the present invention can be prepared in a number of ways well known to those skilled in the art of organic synthesis. The compounds of the present invention can be synthesised using the methods outlined below, together with methods known in the art of synthetic organic chemistry, or variations thereof as appreciated by those skilled in the art. Preferred methods include, but are not limited to, those described below.

The novel compounds of formula (I) may be prepared using the reactions and techniques described in this section. The reactions are performed in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognised by one skilled in the art. It is understood by one skilled in the art of organic synthesis that the functionality present on various portions of the educt molecule must be compatible with the reagents and reactions proposed. Not all compounds of formula (I) falling into a given class may be compatible with some of the reaction conditions required in some of the methods described. Such restrictions to the substituents which are compatible with the reaction conditions will be readily apparent to one skilled in the art and alternate methods can be used.

Compounds according to the present invention in which X is a hydroxamic acid group —CONHOH may be prepared from compounds of the invention in which X is a carboxylic acid group —COOH. That process comprises reacting an acid of general formula (II) (in these and the following formulae R1, R2, Y and n have the above meanings unless otherwise specifically indicated; R13 represents an alkyl; R14 represents an alkyl or a silyl).

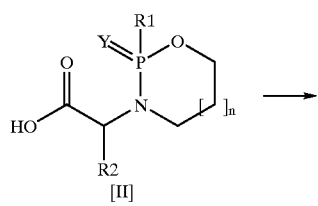
[II]

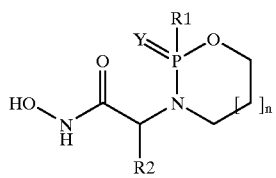

with hydroxylamine, O-protected hydroxylamine, N,O-diprotected hydroxylamine. Other substituents of the acids (II) may themselves be protected from such reaction, then removing any protecting groups from the resulting hydroxamic acid moiety and from any protected substituents in R1, and R2.

The condensation is carried out using any of the many methods for the formation of amide bonds known to one skilled in the art of organic synthesis, e.g. the mixed carbonic anhydride (isobutyl chloroformate) method.

Compounds according to the present invention in which X is a hydroxamic acid group —CONHOH may also be prepared from esters of general formula (III). That process comprises reacting an ester of general formula (III) with hydroxylamine or O-protected hydroxylamine in the presence of a base.

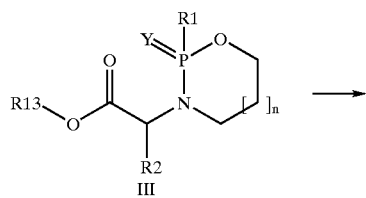
III

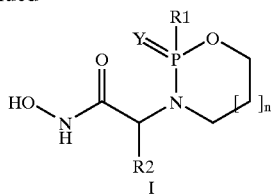
I

Compounds according to the present invention in which X is a carboxylic acid group —COOH may be prepared from esters of general formula (III) by basic hydrolysis.

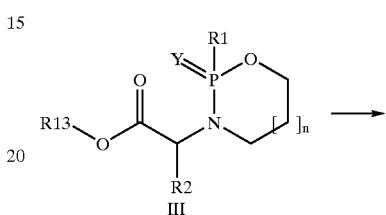
III

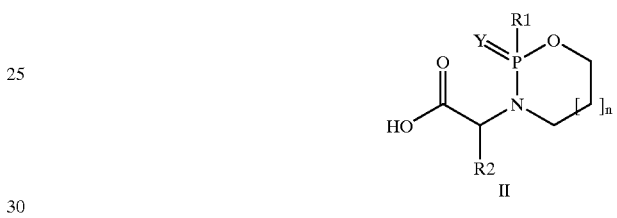
II

The esters of formula (III) may be prepared from phosphonyl dichlorides (IV) and amino alcohols (V) in the presence of a base.

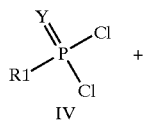
IV

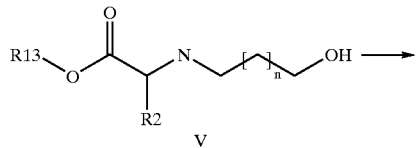
V

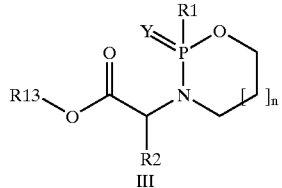
III

The esters of formula (III) may also be prepared from phosphonyl dichlorides (IV) and amino alcohols (VI) in the presence of a base and subsequent alkylation of the intermediate oxazaphosphacycloalkane (VII) utilising haloesters (VIII) in the presence of a base.

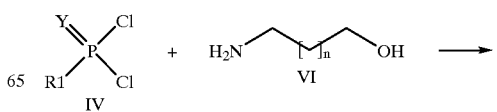
IV VI

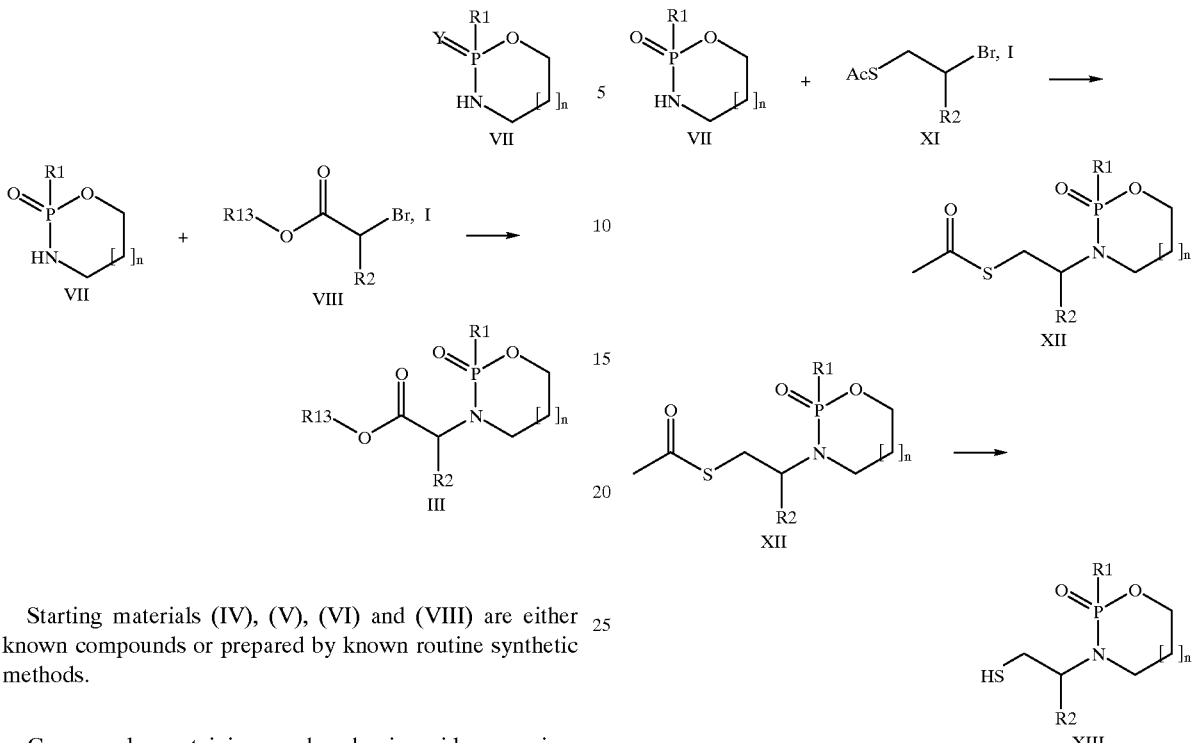

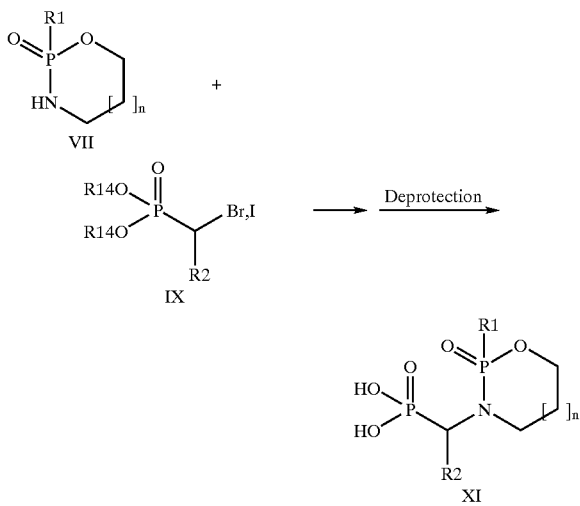

Starting materials (IV), (V), (VI) and (VIII) are either known compounds or prepared by known routine synthetic methods.

Compounds containing a phosphonic acid as a zinc-binding group (X) may be prepared by alkylation of oxazaphosphacycloalkanes (VII) with alkyl or silyl phosphonate halides (IX), in the presence of base, followed by deprotection. The deprotection of alkyl phosphonates is carried out by treatment with TMSI. Silyl phosphonates are readily converted to phosphonic acids by treatment with water.

Compounds containing an acetylthiomethyl moiety (XII) as a zinc binding group may be prepared by alkylation of oxazaphosphacycloalkanes (VII) with an acetylthioethyl halide (XI) in the presence of base. Compounds with a mercaptomethyl zinc-binding group (XIII) may prepared by removal of the acetyl group from compound (XII) with aqueous base.

The present compounds are intended for use in pharmaceutical compositions which are useful in the treatment of the above mentioned diseases.

The amount required of a compound of formula I (hereinafter referred to as the active ingredient) for therapeutic effect will, of course, vary both with the particular compound, the route of administration and the mammal under treatment. A suitable dose of a compound of formula I for systemic treatment is 0.1 to 200 mg/kg body weight, the most preferred dosage being 0.2 to 50 mg/kg of mammal body weight, administered one or more times daily.

While it is possible for an active ingredient, such as a compound according to this invention, to be administered alone as the raw chemical, it is preferable to administer a compound of the invention as a pharmaceutical formulation. Conveniently, the active ingredient comprises from 0.1% to 100% by weight of the formulation. Conveniently, dosage units of a formulation contain between 0.07 mg and 1 g of the active ingredient, preferably from about 0.5 mg to about 500 mg of the active ingredient, more preferably about 50 mg, e.g. for oral administration. For topical administration, the active ingredient preferably comprises from 1% to 20% by weight of the formulation but the active ingredient may comprise as much as 50% w/w. Formulations suitable for nasal or buccal administration may comprise 0.1% to 20% w/w for example about 2% w/w of active ingredient.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and human medical use, of the present invention comprise an active ingredient in association with a pharmaceutically acceptable carrier therefore and optionally other therapeutic ingredient(s). The carrier(s) must be "acceptable" in the sense of being compatible with the other ingredients of the formulations and not deleterious to the recipient thereof. The formulations include those in a form suitable for oral, ophthalmic, rectal, parenteral (including subcutaneous, intramuscular and intravenous), transdermal, intra-articular, topical, nasal, or buccal administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops.

Formulations suitable for administration to the nose or buccal cavity include powder, self-propelling and spray formulations, such as aerosols and atomisers. In addition to the aforementioned ingredients, the formulations of this invention may include one or more additional ingredients.

The compositions may further contain other therapeutically active compounds usually applied in the treatment.

The invention is further illustrated by the following general procedures, preparations and examples.

GENERAL PROCEDURES, PREPARATIONS AND EXAMPLES

The exemplified compounds are listed in Table 4, exemplified compounds of general formula (II) in Table 3, intermediates of general formula (III) in Table 2, and intermediates of general formula (VII) in Table 1.

All melting points are uncorrected. For $^1$H nuclear magnetic resonance (NMR) spectra (300 MHz) and $^{13}$C NMR (75.6 MHz) chemical shift values ($\delta$) (in ppm) are quoted, unless otherwise specified, for deuteriochloroform solutions relative to internal tetramethylsilane ($\delta$=0.00) or chloroform ($\delta$=7.25) or deuteriochloroform ($\delta$=76.81 for $^{13}$C NMR) standards. The value of a multiplet, either defined (doublet (d), triplet (t), quartet (q)) or not (m) at the approximate mid point is given unless a range is quoted. (bs) indicates a broad singlet. Mass spectra were recorded on a QUATTRO II (Micromass). The organic solvents used were anhydrous. Chromatography was performed on silica gel. The following abbreviations have been used throughout:

| | |
|---|---|
| MS | Mass spectroscopy |
| NMM | N-methylmorpholine |
| NMR | Nuclear magnetic resonance |
| rt | Room temperature |
| THF | Tetrahydrofuran |
| TMSI | Trimethylsilyliodid |
| dba | Tris(dibenzylidenacetone)dipalladium (0) |
| ph | phenyl |

TABLE 1

Some compounds of general formula (VII)

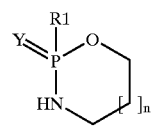

| Comp. No. | Prep no | R1 | Y | n |
|---|---|---|---|---|
| 201 | 1 | phenyl | O | 1 |
| 202 | 2 | phenyl | O | 2 |
| 203 | 3 | phenyl | O | 3 |
| 204 | 4 | 4-methoxy-phenyl | O | 1 |
| 205 | 5 | 4-methoxy-phenyl | O | 2 |
| 206 | 6 | 4-phenoxy-phenyl | O | 2 |
| 207 | 7 | 2-phenyl-ethyl | O | 1 |
| 208 | 8 | n-heptyl | O | 1 |
| 209 | 9 | 4-biphenylyl | O | 1 |

TABLE 2

Some compounds of general formula (III)

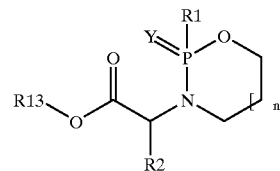

| Comp. no. | Prep. No. | R1 | R2 | R13 | Y | n |
|---|---|---|---|---|---|---|
| 210 | 10 | (4-Cl-phenyl)-oxy | H | Et | O | 1 |
| 211 | 11 | (4-Cl-phenyl)-oxy | H | Me | O | 2 |
| 212 | 12 | (4-Br-phenyl)-methyl | H | Et | O | 1 |
| 213 | 13 | 4-biphenylyl-methyl | H | Et | O | 1 |
| 214 | 14 | 4-biphenylyl | H | Et | O | 1 |
| 215 | 15 | 4-biphenylyl | H | Me | O | 2 |
| 216 | 16 | n-heptyl | H | Et | O | 1 |
| 217 | 17 | n-heptyl | H | Me | O | 2 |

TABLE 2-continued

Some compounds of general formula (III)

| Comp. no. | Prep. No. | R1 | R2 | R13 | Y | n |
|---|---|---|---|---|---|---|
| 218 | 18 | (N-phenyl)-4-aminophenyl | H | Et | O | 1 |
| 219 | 19 | phenyl | H | Et | O | 1 |
| 220 | 20 | phenyl | H | Me | O | 2 |
| 221 | 21 | phenyl (isomers 1) | n-Bu | Et | O | 2 |
| 222 | 22 | phenyl (isomers 2) | n-Bu | Et | O | 2 |
| 223 | 23 | 4-methoxy-phenyl | H | Et | O | 1 |
| 224 | 24 | 4-methoxy-phenyl | H | Me | O | 2 |
| 225 | 25 | 4-methoxy-phenyl | H | Et | O | 4 |
| 226 | 26 | 4-methoxy-phenyl (isomer 1) | i-Pr (R) | Me | O | 1 |
| 227 | 27 | 4-methoxy-phenyl (isomer 2) | i-Pr (R) | Me | O | 1 |
| 228 | 28 | 4-methoxy-phenyl (isomers 1) | n-Bu | Et | O | 2 |
| 229 | 29 | 4-methoxy-phenyl (isomers 2) | n-Bu | Et | O | 2 |
| 230 | 30 | 4-methoxy-phenyl (isomers 1) | n-Bu | Et | O | 3 |
| 231 | 31 | 4-methoxy-phenyl (isomers 2) | n-Bu | Et | O | 3 |
| 232 | 32 | 4-methoxy-phenyl (isomers 1) | allyl | Me | O | 1 |
| 233 | 33 | 4-methoxy-phenyl (isomers 2) | allyl | Me | O | 1 |
| 234 | 34 | 4-methoxy-phenyl (isomers 1) | allyl | Et | O | 2 |
| 235 | 35 | 4-methoxy-phenyl (isomers 2) | allyl | Et | O | 2 |
| 236 | 36 | 4-methoxy-phenyl (isomer 1) | i-Bu (R) | Me | O | 1 |
| 237 | 37 | 4-methoxy-phenyl (isomer 2) | i-Bu (R) | Me | O | 1 |
| 238 | 38 | 4-methoxy-phenyl (isomers 1) | i-Bu | Et | O | 2 |
| 239 | 39 | 4-methoxy-phenyl (isomers 2) | i-Bu | Et | O | 2 |
| 240 | 40 | 4-methoxy-phenyl (isomer 1) | i-Bu (S) | Me | O | 1 |
| 241 | 41 | 4-methoxy-phenyl (isomer 2) | i-Bu (S) | Me | O | 1 |
| 242 | 42 | 4-methoxy-phenyl (isomers 1) | n-Octyl | Et | O | 2 |
| 243 | 43 | 4-methoxy-phenyl (isomers) | n-Octyl | Et | O | 2 |
| 244 | 44 | 4-methoxy-phenyl (isomer 1) | Bn (S) | Et | O | 1 |
| 245 | 45 | 4-methoxy-pheny (isomer 2)l | Bn (S) | Et | O | 1 |
| 246 | 46 | 4-methoxy-phenyl (isomer 1) | Bn (R) | Me | O | 1 |
| 247 | 47 | 4-methoxy-phenyl (isomer 2) | Bn (R) | Me | O | 1 |
| 248 | 48 | 4-phenoxy-phenyl | H | Et | O | 1 |
| 249 | 49 | 4-phenoxy-phenyl | H | Me | O | 2 |
| 250 | 50 | 4-phenoxy-phenyl | H | Me | O | 3 |
| 251 | 51 | 4-phenoxy-pheny (isomers 1)l | allyl | Me | O | 1 |
| 252 | 52 | 4-phenoxy-phenyl (isomers 2) | allyl | Me | O | 1 |
| 253 | 53 | 4-phenoxy-phenyl (isomers 1) | n-Bu | Et | O | 2 |
| 254 | 54 | 4-phenoxy-phenyl (isomers 2) | n-Bu | Et | O | 2 |
| 255 | 55 | 4-phenoxy-phenyl (isomer 1) | i-Bu (R) | Me | O | 1 |
| 256 | 56 | 4-phenoxy-phenyl (isomer 2) | i-Bu (R) | Me | O | 1 |
| 257 | 57 | 4-phenoxy-phenyl (isomers 1) | n-Octyl | Et | O | 2 |
| 258 | 58 | 4-phenoxy-phenyl (isomers 2) | n-Octyl | Et | O | 2 |
| 259 | 59 | 4-phenoxy-phenyl (isomer 1) | i-Pr (R) | Me | O | 1 |
| 260 | 60 | 2-phenylethyl | H | Et | O | 1 |
| 261 | 61 | 4-methoxyphenyl | H | Me | O | 3 |
| 262 | 62 | phenyl | H | Me | O | 3 |
| 263 | 63 | n-heptyl | H | Me | O | 3 |
| 264 | 64 | 4-biphenylyl (Isomer 1) | i-Pr (R) | Me | O | 1 |
| 265 | 65 | 4-biphenylyl (Isomer 2) | i-Pr (R) | Me | O | 1 |
| 266 | 66 | 4-biphenylyl (Isomer 1) | phenyl-methyl (R) | Me | O | 1 |

TABLE 2-continued

Some compounds of general formula (III)

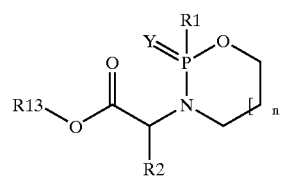

| Comp. no. | Prep. No. | R1 | R2 | R13 | Y | n |
|---|---|---|---|---|---|---|
| 267 | 67 | 4-biphenylyl (Isomer 2) | phenyl-methyl (R) | Me | O | 1 |
| 268 | 68 | 4-(4-Cl-phenyloxy)-phenyl | H | Et | O | 2 |
| 269 | 69 | 4-(4-Cl-phenyloxy)-phenyl | H | Et | O | 3 |
| 270 | 70 | 4'-Br-4-biphenylyl | H | Et | O | 1 |
| 271 | 71 | 4'-Br-4-biphenylyl | H | Et | O | 2 |
| 272 | 72 | 4'-Br-4-biphenylyl | H | Me | O | 3 |
| 273 | 73 | 2-(1-napthyl)-ethyl | H | Et | O | 1 |
| 274 | 74 | phenyl | H | Et | S | 1 |
| 275 | 75 | phenyl | H | Et | S | 2 |
| 276 | 76 | phenyl | H | Me | S | 3 |
| 277 | 77 | 4-(4-Cl-phenyloxy)-phenyl | H | Et | O | 1 |
| 278 | 78 | 4-(4-Cl-phenyloxy)-phenyl (isomer 1) | i-Pr (R) | Me | O | 1 |
| 279 | 79 | 4-(4-Cl-phenyloxy)-phenyl (isomer 2) | i-Pr (R) | Me | O | 1 |
| 280 | 80 | 4-bromophenyl | H | Et | O | 1 |
| 281 | 81 | 4-bromophenyl | H | Et | O | 2 |
| 282 | 82 | 4-benzyloxy-phenyl | H | Et | O | 1 |
| 283 | 83 | 4-benzyloxy-phenyl | H | Et | O | 2 |
| 284 | 84 | 4-benzyloxy-phenyl | H | Et | O | 3 |
| 285 | 85 | 4-(4-CF$_3$)-phenyloxy-phenyl | H | Et | O | 1 |
| 286 | 86 | 4-(4-CF$_3$)-phenyloxy-phenyl | H | Et | O | 2 |
| 287 | 87 | 4-(4-CF$_3$)-phenyloxy-phenyl (isomer 1) | i-Pr (R) | Me | O | 1 |
| 288 | 88 | 4-(4-CF$_3$)-phenyloxy-phenyl (isomer 2) | i-Pr (R) | Me | O | 1 |
| 289 | 89 | 4-(4-Br-phenyloxy)-phenyl | H | Et | O | 1 |
| 290 | 90 | 4-(4-Br-phenyloxy)-phenyl | H | Et | O | 2 |
| 291 | 91 | 4-nitro-phenyl | H | Et | O | 2 |
| 292 | 92 | (N-(4-Cl-benzoyl)-4-aminophenyl | H | Et | O | 2 |
| 293 | 93 | N-benzoyl-aminophenyl | H | Et | O | 2 |
| 294 | 94 | 4-phenoxy-phenyl (isomer 1) | i-Pr (R) | Me | O | 1 |
| 295 | 95 | 4-methoxy-phenyl (isomers 1) | n-Bu | Et | O | 1 |
| 296 | 96 | 4-methoxy-phenyl (isomers 2) | n-Bu | Et | O | 1 |
| 297 | 97 | phenyl | H | Et | O | 4 |

TABLE 3

Some compounds of general formula (II)

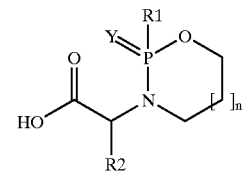

| Comp. No. | Prep. No. | R1 | R2 | Y | n |
|---|---|---|---|---|---|
| 300 | 100 | 4-methoxy-phenyl (isomer 1) | i-Pr (R) | O | 1 |
| 301 | 101 | 4-methoxy-phenyl (isomer 2) | i-Pr (R) | O | 1 |
| 302 | 102 | 4-biphenylyl (isomer 1) | i-Pr (R) | O | 1 |
| 303 | 103 | 4-biphenylyl (isomer 1) | phenyl-methyl (R) | O | 1 |
| 304 | 104 | 4-biphenylyl (isomer 2) | phenyl-methyl (R) | O | 1 |
| 305 | 105 | phenyl | H | O | 2 |
| 306 | 106 | phenyl | H | O | 3 |
| 307 | 107 | phenyl (isomers 1) | n-Bu | O | 2 |
| 308 | 108 | phenyl (isomers 2) | n-Bu | O | 2 |
| 309 | 109 | 4-methoxy-phenyl | H | O | 1 |
| 310 | 110 | 4-methoxy-phenyl | H | O | 2 |
| 311 | 111 | 4-methoxy-phenyl (isomers 1) | n-Bu | O | 1 |
| 312 | 112 | 4-methoxy-phenyl (isomers 2) | n-Bu | O | 1 |

TABLE 3-continued

Some compounds of general formula (II)

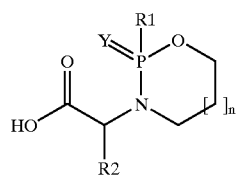

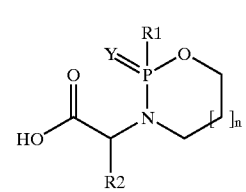

| Comp. No. | Prep. No. | R1 | R2 | Y | n |
|---|---|---|---|---|---|
| 313 | 113 | 4-methoxy-phenyl (isomers 1) | n-Bu | O | 2 |
| 314 | 114 | 4-methoxy-phenyl (isomers 2) | n-Bu | O | 2 |
| 315 | 115 | 4-methoxy-phenyl (isomers 1) | n-Bu | O | 3 |
| 316 | 116 | 4-methoxy-phenyl (isomers 2) | n-Bu | O | 3 |
| 317 | 117 | 4-methoxy-phenyl (isomers 1) | allyl | O | 1 |
| 318 | 118 | 4-methoxy-phenyl (isomers 2) | allyl | O | 1 |
| 319 | 119 | 4-methoxy-phenyl (isomer 1) | i-Bu (R) | O | 1 |
| 320 | 120 | 4-methoxy-phenyl (isomer 2) | i-Bu (R) | O | 1 |
| 321 | 121 | 4-methoxy-phenyl (isomers 1) | i-Bu | O | 2 |
| 322 | 122 | 4-methoxy-pheny (isomers 2)1 | i-Bu | O | 2 |
| 323 | 123 | 4-methoxy-phenyl (isomer 1) | i-Bu (S) | O | 1 |
| 324 | 124 | 4-methoxy-phenyl (isomer 2) | i-Bu (S) | O | 1 |
| 325 | 125 | 4-methoxy-pheny (isomers 1)l | n-Oct | O | 2 |
| 326 | 126 | 4-methoxy-phenyl (isomers 2) | n-Oct | O | 2 |
| 327 | 127 | 4-methoxy-phenyl (isomer 1) | Bn (R) | O | 1 |
| 328 | 128 | 4-methoxy-pheny (isomer 2)l | Bn (R) | O | 1 |
| 329 | 129 | 4-methoxy-phenyl (isomers 1) | n-Pr | O | 1 |
| 330 | 130 | 4-methoxy-phenyl (isomers 2) | n-Pr | O | 1 |
| 331 | 131 | 4-methoxy-phenyl (isomers 1) | allyl | O | 2 |
| 332 | 132 | 4-methoxy-phenyl(isomers 2) | allyl | O | 2 |
| 333 | 133 | 4-phenoxy-phenyl (isomers 1) | allyl | O | 1 |
| 334 | 134 | 4-phenoxy-phenyl (isomers 2) | allyl | O | 1 |
| 335 | 135 | 4-phenoxy-phenyl (isomers 1) | n-Bu | O | 2 |
| 336 | 136 | 4-phenoxy-phenyl (isomers 2) | n-Bu | O | 2 |
| 337 | 137 | 4-phenoxy-phenyl (isomer 1) | i-Bu (R) | O | 1 |
| 338 | 138 | 4-phenoxy-phenyl (isomer 2) | i-Bu (R) | O | 1 |
| 339 | 139 | 4-phenoxy-pheny (isomers 1)1 | n-Oct | O | 2 |
| 340 | 140 | 4-phenoxy-phenyl (isomers 2) | n-Oct | O | 2 |
| 341 | 141 | 4-phenoxy-phenyl (isomer 1) | i-Pr (R) | O | 1 |
| 342 | 142 | 4-phenoxy-phenyl (isomer 2) | i-Pr (R) | O | 1 |
| 343 | 143 | 4-(4-Cl-phenoxy)-phenyl | H | O | 2 |
| 344 | 144 | 4-(4-Cl-phenoxy)-phenyl (isomer 1) | i-Pr (R) | O | 1 |
| 345 | 145 | 4-(4-CF$_3$-phenoxy)-phenyl (isomer 2) | i-Pr (R) | O | 1 |
| 346 | 146 | 4-(4-CF$_3$-phenoxy)-phenyl (isomer 1) | i-Pr (R) | O | 1 |
| 347 | 147 | 4-(4-Br-phenoxy)-phenyl (isomer 2) | H | O | 1 |
| 348 | 148 | 4-(4-Br-phenoxy)-phenyl | H | O | 2 |
| 349 | 149 | 4-nitrophenyl | H | O | 2 |
| 350 | 150 | (N-(4-Cl-benzoyl))-4-aminophenyl | H | O | 2 |
| 351 | 151 | (N-benzoyl)-4-aminophenyl | H | O | 2 |
| 352 | 152 | phenyl | H | S | 1 |
| 353 | 153 | phenyl | H | S | 2 |

TABLE 4

Exemplified compounds (I)

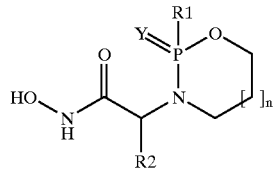

| Comp. No. | Ex. No. | R1 | R2 | Y | n |
|---|---|---|---|---|---|
| 101 | 1 | (4-Cl-phenyl)-oxy | H | O | 1 |
| 102 | 2 | (4-Cl-phenyl)-oxy | H | O | 2 |
| 103 | 3 | (4-Br-phenyl)-methyl | H | O | 1 |
| 104 | 4 | 4-biphenylyl-methyl | H | O | 1 |
| 105 | 5 | 4-biphenylyl | H | O | 1 |
| 106 | 6 | 4-biphenylyl | H | O | 2 |
| 107 | 7 | n-heptyl | H | O | 1 |
| 108 | 8 | n-heptyl | H | O | 2 |
| 109 | 9 | (N-phenyl)-4-aminophenyl | H | O | 1 |
| 110 | 10 | phenyl | H | O | 1 |
| 111 | 11 | phenyl | H | O | 2 |
| 112 | 12 | phenyl | H | O | 4 |
| 113 | 13 | phenyl (isomers 1) | n-Bu | O | 2 |
| 114 | 14 | phenyl (isomers 2) | n-Bu | O | 2 |
| 115 | 15 | 4-methoxy-phenyl | H | O | 1 |
| 116 | 16 | 4-methoxy-phenyl | H | O | 2 |
| 117 | 17 | 4-methoxy-phenyl | H | O | 4 |
| 118 | 18 | 4-methoxy-phenyl (isomer 1) | i-Pr (R) | O | 1 |
| 119 | 19 | 4-methoxy-phenyl (isomer 2) | i-Pr (R) | O | 1 |
| 120 | 20 | 4-methoxy-phenyl (isomers 1) | n-Bu | O | 1 |
| 121 | 21 | 4-methoxy-phenyl (isomers 2) | n-Bu | O | 1 |
| 122 | 22 | 4-methoxy-phenyl (isomers 1) | n-Bu | O | 2 |
| 123 | 23 | 4-methoxy-phenyl (isomers 2) | n-Bu | O | 2 |
| 124 | 24 | 4-methoxy-phenyl (isomers 1) | n-Bu | O | 3 |
| 125 | 25 | 4-methoxy-phenyl (isomers 2) | n-Bu | O | 3 |
| 126 | 26 | 4-methoxy-phenyl (isomers 1) | allyl | O | 1 |
| 127 | 27 | 4-methoxy-phenyl (isomers 2) | allyl | O | 1 |
| 128 | 28 | 4-methoxy-phenyl (isomers 1) | allyl | O | 2 |
| 129 | 29 | 4-methoxy-phenyl (isomers 2) | allyl | O | 2 |
| 130 | 30 | 4-methoxy-phenyl (isomer 1) | i-Bu (R) | O | 1 |
| 131 | 31 | 4-methoxy-phenyl (isomer 2) | i-Bu (R) | O | 1 |
| 132 | 32 | 4-methoxy-phenyl (isomer 1) | i-Bu (S) | O | 1 |
| 133 | 33 | 4-methoxy-phenyl (isomer 2) | i-Bu (S) | O | 1 |
| 134 | 34 | 4-methoxy-phenyl (isomers 1) | i-Bu | O | 2 |
| 135 | 35 | 4-methoxy-phenyl (isomers 2) | i-Bu | O | 2 |
| 136 | 36 | 4-methoxy-phenyl (isomers 1) | n-Pr | O | 1 |
| 137 | 37 | 4-methoxy-phenyl (isomers 2) | n-Pr | O | 1 |
| 138 | 38 | 4-methoxy-phenyl (isomers 1) | n-Oct | O | 2 |
| 139 | 39 | 4-methoxy-phenyl (isomers 2) | n-Oct | O | 2 |
| 140 | 40 | 4-methoxy-phenyl (isomer 1) | Bn (R) | O | 1 |
| 141 | 41 | 4-methoxy-phenyl (isomer 1) | Bn (S) | O | 1 |
| 142 | 42 | 4-methoxy-phenyl (isomer 2) | Bn (S) | O | 1 |
| 143 | 43 | 4-phenoxy-phenyl | H | O | 1 |
| 144 | 44 | 4-phenoxy-phenyl | H | O | 2 |
| 145 | 45 | 4-phenoxy-phenyl | H | O | 3 |
| 146 | 46 | 4-phenoxy-phenyl (isomers 1) | allyl | O | 1 |
| 147 | 47 | 4-phenoxy-phenyl (isomers 2) | allyl | O | 1 |
| 148 | 48 | 4-phenoxy-phenyl (isomer 1) | i-Bu (R) | O | 1 |
| 149 | 49 | 4-phenoxy-phenyl (isomer 2)l | i-Bu (R) | O | 1 |
| 150 | 50 | 4-phenoxy-phenyl (isomer 1) | i-Pr (R) | O | 1 |
| 151 | 51 | 4-phenoxy-phenyl (isomer 2) | i-Pr (R) | O | 1 |

TABLE 4-continued

Exemplified compounds (I)

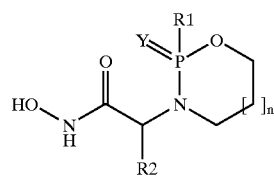

| Comp. No. | Ex. No. | R1 | R2 | Y | n |
|---|---|---|---|---|---|
| 152 | 52 | 4-phenoxy-phenyl (isomers 1) | n-Bu | O | 2 |
| 153 | 53 | 4-phenoxy-phenyl (isomers 2) | n-Bu | O | 2 |
| 154 | 54 | 4-phenoxy-phenyl (isomers 1) | n-Oct | O | 2 |
| 155 | 55 | 4-phenoxy-phenyl (isomers 2) | n-Oct | O | 2 |
| 156 | 56 | 2-phenylethyl | H | O | 1 |
| 157 | 57 | 4-methoxy-phenyl | H | O | 3 |
| 158 | 58 | phenyl | H | O | 3 |
| 159 | 59 | n-heptyl | H | O | 3 |
| 160 | 60 | 4-biphenylyl (isomer 2) | i-Pr (R) | O | 1 |
| 161 | 61 | 4-(4-Cl-phenyloxy)-phenyl | H | O | 2 |
| 162 | 62 | 4-(4-Cl-phenyloxy)-phenyl | H | O | 3 |
| 163 | 63 | 4-(4-Cl-phenyloxy)-phenyl (isomer 1) | i-Pr (R) | O | 1 |
| 164 | 64 | 4'-Br-4-biphenylyl | H | O | 1 |
| 165 | 65 | 4'-Br-4-biphenylyl | H | O | 2 |
| 166 | 66 | 4'-Br-4-biphenylyl | H | O | 3 |
| 167 | 67 | 2-(1-napthyl)-ethyl | H | O | 1 |
| 168 | 68 | phenyl | H | S | 1 |
| 169 | 69 | phenyl | H | S | 2 |
| 170 | 70 | phenyl | H | S | 3 |
| 171 | 71 | 4-(4-Cl-phenyloxy)-phenyl | H | O | 1 |
| 172 | 72 | 4-bromophenyl | H | O | 1 |
| 173 | 73 | 4-bromophenyl | H | O | 2 |
| 174 | 74 | 4-benzyloxy-phenyl | H | O | 1 |
| 175 | 75 | 4-benzyloxy-phenyl | H | O | 2 |
| 176 | 76 | 4-benzyloxy-phenyl | H | O | 3 |
| 177 | 77 | 2-(4-Cl-phenoxy-phenyl) | H | O | 2 |
| 178 | 78 | 4-(4-CF$_3$-phenoxy)-phenyl | H | O | 1 |
| 179 | 79 | 4-(4-CF$_3$-phenoxy)-phenyl | H | O | 2 |
| 180 | 80 | 4-(4-CF$_3$-phenoxy)-phenyl (isomer 1) | i-Pr (R) | O | 1 |
| 181 | 81 | 4-(4-CF$_3$-phenoxy)-phenyl (isomer 2) | i-Pr (R) | O | 1 |

TABLE 4-continued

Exemplified compounds (I)

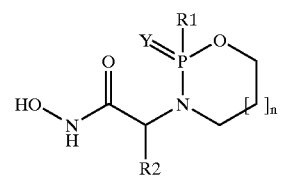

| Comp. No. | Ex. No. | R1 | R2 | Y | n |
|---|---|---|---|---|---|
| 182 | 82 | 4-(4-Br-phenyloxy)-phenyl | H | O | 1 |
| 183 | 83 | 4-(4-Br-phenyloxy)-phenyl | H | O | 2 |
| 184 | 84 | 4-nitrophenyl | H | O | 2 |
| 185 | 85 | (N-(4-Cl-benzoyl))-4-aminophenyl | H | O | 2 |
| 186 | 86 | (N-benzoyl)-4-aminophenyl | H | O | 2 |

General Procedure 1

Formation of hydroxamic acids of general formula (I) from the corresponding carboxylic acids of general formula (II).

A solution of carboxylic acid with general formula (II) (2.9 mmol) in THF (45 ml) was cooled to −10° C. under argon. NMM (0.3 ml, 3.0 mmol) and isobutyl chloroformate (0.4 ml, 3.0 mmol) were then added with stirring. After stirring overnight at −10° C., O-trimethylsilyl hydroxylamine (0.4 ml, 3.2 mmol) was added, and the mixture was left at −10° C. for 5 h. The mixture was then acidified with 4M acetic acid, extracted with EtOAc/H$_2$O. The aqueous layer was back-extracted with EtOAc, and the combined organic layers were washed with brine, dried (MgSO$_4$) and concentrated. The residue was purified by chromatography (chloroform/methanol/NH$_3$ (25%) 90:10:1) or crystallisation to afford the hydroxamic acid of general formula (I).

General Procedure 2

Formation of hydroxamic acids of general formula (I) from the corresponding esters of general formula (III).

To a solution of ester with general formula (III) (0.20 mmol) in dry methanol (2 ml) was added O-trimethylsilyl-hydroxylamine (72 μl, 0.60 mmol) and sodium methoxide (1.4M, 214 μl, 0.30 mmol). After stirring at rt for 1 hour, the solution was acidified with 4M AcOH to pH 4, concentrated under reduced pressure and extracted with EtOAc/H$_2$O. The aqueous layer was back-extracted with EtOAc, and the combined organic layers were washed with brine, dried (MgSO$_4$) and concentrated under reduced pressure. The residue was purified by chromatography (chloroform/methanol/NH$_3$ (25% aq.) 90:10:1) or crystallisation to afford the hydroxamic acid of general formula (I).

General Procedure 3

Formation of carboxylic acids of general formula (II) from the corresponding oxazaphosphacycloalkane esters of general formula (III).

A solution of ester with general formula (III) (0.26 mmol) in methanol (2 ml) and aqueous sodium hydroxide (2M, 2 ml) was stirred overnight at rt, acidified with 4M AcOH and extracted with EtOAc/H$_2$O. The aqueous phase was back-extracted with EtOAc, and the combined layers were washed with brine, dried (MgSO$_4$) and concentrated under reduced pressure. The residue was purified by chromatography (chloroform/methanol/acetic acid 80:20:1) or by crystallisation to afford the carboxylic acid of general formula (II).

General Procedure 4

Formation of oxazaphosphacycloalkane esters of general formula (III) by cyclisation of phosphonyldichlorides of general formula (IV) with amino alcohols of general formula (V).

A solution of amino alcohol of general formula (V) (0.42 mmol) and NMM (0.85 mmol) in dry CH$_2$Cl$_2$ (20 ml) was cooled to −40° C. under argon, and a solution phosphony-idichloride of general formula (IV) (0.42 mmol) in dry CH$_2$Cl$_2$ (10 ml) was added. The mixture was stirred at −40° C. for 1 hour, then at rt overnight. After quenching with water, the aqueous phase was extracted with EtOAc. The combined organic layers were washed with brine, dried (MgSO$_4$) and concentrated under reduced pressure. The residue was purified by chromatography (chloroform/methanol) to afford the oxazaphosphacycloalkane ester of general formula (III).

General Procedure 5

Formation of oxazaphosphacycloalkanes of general formula (VII) by cyclisation of phosphonyldichlorides of general formula (IV) with amino alcohols of general formula (VI).

A solution of amino alcohol of general formula (VI) (9.57 mmol) and N-ethylmorpholine (19.1 mmol) in dry CH$_2$Cl$_2$ and a solution of phosphonyldichloride of general formula (IV) in dry CH$_2$Cl$_2$ (each with a total volume of 9 ml) were added simultaneously to 22 ml dry CH$_2$Cl$_2$ at 0° C. with stirring over a period of 2 hours. After the addition was completed, the suspension was stirred overnight at rt and extracted with EtOAc/H$_2$O. The aqueous phase was back-extracted thoroughly with EtOAc, and the combined organic extracts were dried (MgSO$_4$) and concentrated under reduced pressure. The residue was purified by crystallisation to afford the oxazaphosphacycloalkane of general formula (VII).

General Procedure 6

Formation of oxazaphosphacycloalkane esters of general formula (III) by alkylation of oxazaphosphacycloalkanes of general formula (VII) with bromoacetic acid esters of general formula (VIII).

A solution of oxazaphosphacycloalkane of general formula (VII) (0.76 mmol) in dry THF (4 ml) was cooled to −70° C., and n-butyllithium (0.76 mmol) was added dropwise followed by a solution of bromo- or iodoacetic acid ester of general formula (VIII) (0.76 mmol) in dry THF (1.5 ml). The mixture was removed from the cooling bath and stirred at rt for 4 hours, quenched with water and extracted with EtOAc/H$_2$O. The aqueous phase was back-extracted with EtOAc, and the combined organic layers were washed with water and brine, dried (MgSO$_4$) and concentrated under reduced pressure. The residue was purified by chromatography to afford the oxazaphosphacycloalkane ester of general formula (III).

Preparation 1

(±)-2-Oxo-2-phenyl-1,3,2-oxazaphosphorinane (compound 201).

General procedure 5.

Starting materials: 3-Amino-1-propanol and phenylphosphonic dichloride.

$^1$H NMR (CDCl$_3$) δ 7.87-7.75 (m, 2H), 7.56-7.40 (m, 3H), 4.45 (m, 1H), 4.12 (m, 1H), 3.74 (bs, 1H), 3.43 (m, 1H), 3.20 (m, 1H), 2.06 (m, 1H), 1.73 (m, 1H).

Preparation 2

(±)-2-Oxo-2-phenyl-1,3,2-oxazaphosphorepane (compound 202).

General procedure 5.

Starting materials: 4-Amino-1-butanol and phenylphosphonic dichloride.

$^{13}$C NMR (CDCl$_3$) δ 131.5, 131.4, 130.9, 128.3, 65.4, 41.2, 31.9, 29.9.

Preparation 3

(±)-2-Oxo-2-phenyl-1,3,2-oxazaphosphorocane (compound 203).

General procedure 5.

Starting materials: 5-Amino-1-pentanol and phenylphosphonic dichloride.

$^{13}$C NMR (CDCl$_3$) δ 131.5, 131.4, 130.9, 128.3, 66.0, 41.3, 29.7, 29.2, 24.2.

Preparation 4

(±)-2-(4-Methoxyphenyl)-2-oxo-1,3,2-oxazaphosphorinane (compound 204).

General procedure 5.

Starting materials: 3-Amino-1-propanol and 4-methoxyphenylphosphonic dichloride.

$^1$H NMR (CDCl$_3$) δ 7.75 (m, 2H), 6.96 (m, 2H), 4.45 (m, 1H), 4.12 (m, 1H), 3.85 (s, 3H), 3.43 (m, 2H), 3.21 (m, 1H), 2.04 (m, 1H), 1.76 (m, 1H).

Preparation 5

(±)-2-(4-Methoxyphenyl)-2-oxo-1,3,2-oxazaphosphorepane (compound 205)

General procedure 5.

Starting materials: 4-Amino-1-butanol and 4-methoxyphenylphosphonic dichloride.

$^{13}$C NMR (CDCl$_3$) δ 162.2, 132.8, 122.8, 113.9, 65.2, 55.3, 41.2, 32.0, 30.0.

Preparation 6

(±)-2-Oxo-2-(4-phenoxyphenyl)-1,3,2-oxazaphosphorepane (compound 206)

General procedure 5.

Starting materials: 4-Amino-1-butanol and phenylphosphonic dichloride.

$^{13}$C NMR (CDCl$_3$) δ 160.6, 156.0, 132.9, 129.9, 125.2, 124.2, 119.8, 117.8, 65.4, 41.2, 32.0, 30.0

Preparation 7

(±)-2-Oxo-2-(2-phenylethyl)-1,3,2-oxazaphosphorinane (compound 207).

General procedure 5.

Starting materials: 3-Amino-1-propanol and 2-phenylethyl phosphonic dichloride.

$^1$H NMR (CDCl$_3$) δ 7.30 (m, 2H), 7.22 (m, 3H), 4.41 (m, 1H), 4.16 (m, 1H), 3.33 (m, 1H), 3.15 (m, 1H), 2.69 (m, 3H), 2.12 (m, 2H), 1.98 (m, 1H), 1.76 (m, 1H).

Preparation 8

(±)-2-Heptyl-2-oxo-1,3,2-oxazaphosphorinane (compound 208).

General procedure 5.

Starting materials: 3-Amino-1-propanol and n-heptylphosphonic dichloride.

$^1$H NMR (CDCl$_3$) δ 4.41 (m, 1H), 4.17 (m, 1H), 3.35 (m, 1H), 3.19 (m, 1H), 2.91 (bs, 1H), 1.98 (m, 1H), 1.77 (m, 2H), 1.62 (m, 2H), 1.48-1.20 (m, 9H), 0.88 (t, 3H).

Preparation 9

(±)-2-(4-Biphenylyl)-2-oxo-1 3,2-oxazaphosphorinane (compound 209).

General procedure 5.

Starting materials: 3-Amino-1-propanol and 4-biphenylylphosphonic dichloride.

$^1$H NMR (CDCl$_3$) δ 7.88 (m, 2H), 7.68 (m, 2H), 7.60 (m, 2H), 7.43 (m, 3H), 4.50 (m, 1H), 4.18 (m, 1H), 3.46 (m, 2H), 3.27 (m, 1H), 2.08 (m, 1H), 1.79 (m, 1H).

Preparation 10

(±)-Ethyl 2-(4-chlorophenoxy)-2-oxo-1,3,2-oxazaphosphorinane-3-acetate (compound 210).

General procedure 4.

Starting materials: 4-Chlorophenylphosphoryl dichloride and N-(3-hydroxypropyl)glycine ethyl ester.

$^{13}$C NMR (CDCl$_3$) δ 169.7, 149.6, 129.9, 129.7, 121.4, 70.0, 61.2, 49.8, 48.0, 25.9, 14.2.

Preparation 11

(±)-Methyl 2-(4-chlorophenoxy)-2-oxo-1,3,2-oxazaphosphorepane-3-acetate (compound 211).

General procedure 4.

Starting materials: 4-Chlorophenylphosphoryl dichloride and N-(4-hydroxy-butyl)glycine methyl ester.

$^{13}$C NMR (CDCl$_3$) δ 171.1, 149.6, 130.1, 129.5, 122.1, 67.1, 52.1, 49.9, 48.2, 29.6, 26.3.

Preparation 12

(±)-Ethyl 2-[(4-bromophenyl)methyl]-2-oxo-1,3,2-oxazaphosphorinane-3-acetate (compound 212).

General procedure 4.

Starting materials: 4-Bromophenylphosphonic dichloride and N-(3-hydroxypropyl)glycine ethyl ester.

$^1$H NMR (CDCl$_3$) δ (d, 2H), 7.27 (dd, 2H), 4.32 (m, 1H), 4.24-3.98 (m, 2H), 4.19 (q, 2H), 3.57 (dd, 1H), 3.23 (m, 3H), 2,97 (m, 1H), 1.88 (m, 1H), 1.33 (m, 1H), 1.28 (t, 3H).

Preparation 13

(±)-Ethyl 2-[(4-biphenylyl)methyl]-2-oxo-1,3,2-oxazaphosphorinane-3-acetate (compound 213).

Procedure: A mixture of compound 210 (0.21 mmol) and Pd(PPh$_3$)$_4$ (0.0105 mmol) in toluene (1.5 ml) was stirred for 30 min under an argon atmosphere, after which phenyl boronic acid (0.42 mmol) and Na$_2$CO$_3$ (0.46 mmol in 230 μl H$_2$O) was added, and the mixture was stirred at 110° C. overnight. The mixture was diluted with ether, filtered through Celite, concentrated under reduced pressure, and purified by flash chromatography to afford compound 211.

$^1$H NMR (CDCl$_3$) δ 7.58(m, 4H), 7.43 (m, 4H), 7.33 (m, 1H), 4.34 (m, 1H), 4.25-4.00 (m, 2H), 4.20 (q, 2H), 3.63 (dd, 1H), 3.45-3.18 (m, 3H), 2.99 (m, 1H), 1.87(m, 1H), 1.36 (m, 1H), 1.28 (t, 3H).

Preparation 14

(±)-Ethyl 2-(4-biphenylyl)-2-oxo-1,3,2-oxazaphosphorinane-3-acetate (compound 214).

General procedure 6.

Starting materials: Compound 209 and ethyl bromoacetate.

$^1$H NMR (CDCl$_3$) δ 7.95 (m, 2H), 7.68 (m, 2H), 7.61 (m, 2H), 7.46 (m, 2H), 7.40 (m, 1H), 4.53 (m, 1H), 4.25 (m, 1H), 4.20-4.00 (m, 3H), 3.75 (dd, 1H), 3.47 (m, 1H), 3.31 (m, 1H), 2.14 (m, 1H), 2.05 (m, 1H), 1.23 (t, 3H).

Preparation 15

(±)-Methyl 2-(4-biphenylyl)-2-oxo-1,3,2-oxazaphosphorepane-3-acetate (compound 215).

General procedure 4.

Starting materials: 4-Biphenylylphosphonic dichloride and N-(4-hydroxybutyl)glycine methyl ester.

$^{13}$C NMR (CDCl$_3$) δ 171.9, 144.4, 140.3, 131.8, 129.2, 128.9, 127.9, 127.3, 127.0, 65.3, 51.9, 48.5, 47.5, 29.5, 26.6.

Preparation 16

(±)-Ethyl 2-heptyl-2-oxo-1,3,2-oxazaphosphorinane-3-acetate (compound 216).

General procedure 4.

Starting materials: n-Heptylphosphonic dichloride and N-(3-hydroxypropyl)glycine ethyl ester.

$^1$H NMR (CDCl$_3$) δ 4.39 (m, 1H), 4.18 (q, 2H), 4.17 (m, 2H), 3.60 (dd, 1H), 3.43 (m, 1H), 3.05 (m, 1H), 2.10 (m, 1H), (m, 3H), 1.61 (m, 2H), 1.46-1.20 (m, 8H), 1.27 (t, 3H), 0.88 (t, 3H).

Preparation 17

(±)-Methyl 2-heptyl-2-oxo-1,3,2-oxazaphosphorepane-3-acetate (compound 217).

General procedure 4.

Starting materials: n-Heptylphosphonic dichloride and N-(4-hydroxybutyl)glycine methyl ester.

$^{13}$C NMR (CDCl$_3$) δ 172.2, 64.4, 51.9, 48.5, 47.6, 31.7, 30.9, 29.4, 28.9, 26.9, 26.5, 22.6, 22.5, 14.1.

Preparation 18

(±)-Ethyl 2-oxo-2-[4-(phenylamino)phenyl]-1,3,2-oxazaphosphorinane-3-acetate (compound 218).

Procedure: A mixture of aniline (0.25 mmol), compound 244 (0.27 mmol), Pd$_2$(dba)$_3$ (0.006 mmol), 2,2'-bis(diphenylphosphino)-1,1'-binapthyl (BINAP, 0.02 mmol), and CsCO$_4$ (0.35 mmol) in dioxane (1 ml) under an argon atmosphere was heated to 100° C. overnight. The suspension was then diluted with ether, filtered, concentrated under reduced pressure, and purified by flash chromatography to afford compound 216.

$^1$H NMR (CDCl$_3$) δ 7.73 (m, 2H), 7.32 (m, 2H), 7.15 (m, 2H), 7.04 (m, 3H), 6.10 (bs, 1H), 4.48 (m, 1H), 4.30-4.05 (m, 3H), 3.98 (dd, 1H), 3.65 (dd, 1H), 3.5-3.2 (m, 2H), 2.05 (m, 2H), 1.23 (t, 3H).

Preparation 19

(±)-Ethyl 2-oxo-2-phenyl-1,3,2-oxazaphosphorinane-3-acetate (compound 219).

General procedure 6.

Starting materials: Compound 201 and ethyl bromoacetate.

$^{13}$H NMR (CDCl$_3$) δ 7.88 (m, 2H), 7.47 (m, 3H), 4.51 (m, 1H), 4.3-4.1 (m, 1H), 4.13 (q, 2H), 4.03 (dd, 1H), 3.73 (dd, 1H), 3.44 (m, 1H), 3.28 (m, 1H), 2.14 (m, 1H), 2.00 (m, 1H), 1.35-1.17 (t, 3H).

Preparation 20

(±)-Ethyl 2-oxo-2-phenyl-1,3,2-oxazaphosphorepane-3-acetate (compound 220).

General procedure 4.

Starting materials: Phenylphosphonic dichloride and N-(4-hydroxybutyl)glycine methyl ester.

$^{13}$C NMR (CDCl$_3$) δ 171.3, 131.6, 131.3, 130.6, 128.3, 65.3, 61.0, 48.6, 47.4, 29.5, 26.5, 14.2.

Preparation 21

(±)-Ethyl α-Butyl-2-oxo-2-phenyl-1,3,2-oxazaphosphorepane-3-acetate (diastereomers 1, compound 221).

General procedure 6.

Starting materials: Compound 202 and ethyl 2-iodohexanoate.

$^{13}$C NMR (CDCl$_3$) δ 172.5, 131.5, 131.4, 136.0, 128.0, 65.4, 60.4, 59.2, 43.9, 30.7, 29.8, 29.4, 28.6, 22.5, 14.0, 13.8.

Preparation 22

(±)-Ethyl α-Butyl-2-oxo-2-phenyl-1,3,2-oxazaphosphorepane-3-acetate (diastereomers 2, compound 222).

General procedure 6.

Starting materials: Compound 202 and ethyl 2-iodohexanoate.

$^{13}$C NMR (CDCl$_3$) δ 173.3, 131.5, 131.4, 131.2, 128.2, 65.3, 60.9, 57.8, 41.7, 29.6, 29.0, 28.5, 27.7, 22.3, 14.2, 13.8.

Preparation 23

(±)-Ethyl 2-(4-methoxyphenyl)-2-oxo-1,3,2-oxazaphosphorinane-3-acetate (compound 223).

General procedure 6.

Starting materials: Compound 204 and ethyl bromoacetate.

$^1$H NMR (CDCl$_3$) δ 7.83 (m, 2H), 6.96 (m, 2H), 4.49 (m, 1H), 4.30-4.05 (m, 3H), 3.98 (dd, 1H), 3.84 (s, 3H), 3.65 (dd, 1H), 3.41 (m, 1H), 3.28 (m, 1H), 2.07 (m, 2H), 1.23 (t, 3H).

Preparation 24

(±)-Methyl 2-(4-methoxyphenyl)-2-oxo-1,3,2-oxazaphosphorepane-3-acetate (compound 224).

General procedure 4.

Starting materials: 4-Methoxyphenylphosphonic dichloride and N-(4-hydroxybutyl)glycine methyl ester.

$^1$C NMR (CDCl$_3$) δ 171.9, 162.3, 133.2, 122.0, 113.8, 65.2, 55.3, 51.9, 48.4, 47.4, 29.5, 26.5.

Preparation 25

(±)-Ethyl 2-(4-methoxyphenyl)-2-oxo-1,3,2-oxazaphosphoronane-3-acetate (compound 225).

General procedure 4.

Starting materials: 4-Methoxyphenylphosphonic dichloride and N-(5-hydroxypentyl)glycine methyl ester.

$^{13}$C NMR (CDCl$_3$) δ 171.2, 162.3, 133.8, 121.7, 113.8, 60.9, 60.5, 55.3, 45.9, 42.3, 27.7, 24.3, 19.1, 18.5, 14.2.

Preparation 26

(αR)-Methyl 2-(4-methoxyphenyl)-α-(1-methylethyl)-2-oxo-1,3,2-oxazaphosphorinane-3-acetate (diastereomer 1, compound 226).

General procedure 4.

Starting materials: 4-Methoxyphenylphosphonic dichloride and N-(3-hydroxypropyl)-D-valine methyl ester.

$^1$H NMR (CDCl$_3$) δ 7.64 (m, 2H), 6.94 (m, 2H), 4.44 (m, 1H), 4.20 (m, 1H), 3.85 (t, 1H), 3.84 (s, 3H), 3.45 (s, 3H), 3.43 (m, 2H), 2.16 (m, 2H), 1.96 (m, 1H), 1.14 (d, 3H), 0.90 (d, 3H).

Preparation 27

(αR)-Methyl 2-(4-methoxyphenyl)-α-(1-methylethyl)-2-oxo-1,3,2-oxazaphosphorinane-3-acetate (diastereomer 2, compound 227).

General procedure 4.

Starting materials: 4-Methoxyphenylphosphonic dichloride and N-(3-hydroxypropyl)-D-valine methyl ester.

$^1$H NMR (CDCl$_3$) δ 7.78 (m, 2H), 6.95 (m, 2H), 4.49 (m, 1H), 4.24 (m, 1H), 3.85 (s, 3H), 3.76 (s, 3H), 3.68 (m, 1H), 3.46 (dd, 1H), 3.22 (m, 1H), 2.08 (m, 3H), 0.80 (d, 3H), 0.70 (d, 3H).

Preparation 28

(±)-Ethyl α-butyl-2-(4-methoxyphenyl)-2-oxo-1,3,2-oxazaphosphorepane-3-acetate (diastereomers 1, compound 228).

General procedure 4.

Starting materials: 4-Methoxyphenylphosphonic dichloride and N-(4-hydroxybutyl)-(±)-norleucine ethyl ester.

$^{13}$C NMR (CDCl$_3$) δ 172.7, 162.2, 133.4, 122.5, 113.5, 65.3, 60.4, 59.2, 55.3, 43.9, 30.8, 29.8, 29.5, 28.6, 22.5, 14.0, 13.9.

Preparation 29

(±)-Ethyl α-butyl-2-(4-methoxyphenyl)-2-oxo-1,3,2-oxazaphosphorepane-3-acetate (diastereomers 2 compound 229).

General procedure 4.

Starting materials: 4-Methoxyphenylphosphonic dichloride and N-(4-hydroxybutyl)-(±)-norleucine ethyl ester.

$^{13}$C NMR (CDCl$_3$) δ 173.4, 162.2, 133.3, 122.7, 113.7, 65.2, 60.9, 57.8, 52.3, 41.6, 29.6, 29.0, 28.5, 27.7, 22.3, 14.2, 13.8.

Preparation 30

(±)-Ethyl α-butyl-2-(4-methoxyphenyl)-2-oxo-1,3,2-oxazaphosphorocane-3-acetate (diastereomers 1, compound 230).

General procedure 4.

Starting materials: 4-Methoxyphenylphosphonic dichloride and N-(5-hydroxypentyl)-(±)-norleucine ethyl ester.

$^{13}$C NMR (CDCl$_3$) δ 172.4, 162.1, 133.3, 122.3, 113.5, 65.2, 60.4, 59.1, 55.3, 44.0, 31.6, 29.3, 29.1, 28.9, 24.4, 22.6, 14.0.

Preparation 31

(±)-Ethyl α-butyl-2-(4-methoxyphenyl)-2-oxo-1,3,2-oxazaphosphorocane-3-acetate (diastereomers 2, compound 231).

General procedure 4.

Starting materials: 4-Methoxyphenylphosphonic dichloride and N-(5-hydroxypentyl)-(±)-norleucine ethyl ester.

Calcd. for $C_{20}H_{32}NO_5P$: 397.20; Found [M+H]$^+$=398, [M+Na]$^+$=420.

Preparation 32

(±)-Methyl α-allyl-2-(4-methoxyphenyl)-2-oxo-1,3,2-oxazaphosphorinane-3-acetate (diastereomers 1, compound 232).

General procedure 4.

Starting materials: 4-Methoxyphenylphosphonic dichloride and N-(3-hydroxypropyl)-(±)-allylglycine methyl ester.

$^{13}$C NMR (CDCl$_3$) δ 172.3, 162.5, 134.1, 133.8, 121.8, 117.9, 113.9, 66.7, 57.0, 55.3, 51.7, 41.3, 34.4, 26.7.

Preparation 33

(±)-Methyl α-allyl-2-(4-methoxyphenyl)-2-oxo-1,3,2-oxazaphosphorinane-3-acetate (diastereomers 2, compound 233).

General procedure 4.

Starting materials: 4-Methoxyphenylphosphonic dichloride and N-(3-hydroxypropyl)-(±)-allylglycine methyl ester.

$^{13}$C NMR (CDCl$_3$) δ 172.7, 162.5, 134.1, 134.0, 122.0, 117.9, 113.8, 66.2, 57.3, 55.3, 52.1, 40.8, 34.3, 26.3.

Preparation 34

(±)-Ethyl α-allyl-2-(4-methoxyphenyl)-2-oxo-1,3,2-oxazaphosphorepane-3-acetate (diastereomers 1, compound 234).

General procedure 4.

Starting materials: 4-Methoxyphenylphosphonic dichloride and N-(4-hydroxybutyl)-(±)-allylglycine methyl ester.

$^{13}$C NMR (CDCl$_3$) δ 172.0, 162.2, 134.8, 133.4, 122.4, 117.9, 113.5, 65.3, 60.6, 58.9, 55.3, 43.9, 35.2, 29.5, 29.3, 13.9.

Preparation 35

(±)-Ethyl α-allyl-2-(4-methoxyphenyl)-2-oxo-1,3,2-oxazaphosphorepane-3-acetate (diastereomers 2, compound 235).

General procedure 4.

Starting materials: 4-Methoxyphenylphosphonic dichloride and N-(4-hydroxybutyl)-(±)-allylglycine methyl ester.

$^{13}$C NMR (CDCl$_3$) δ 172.6, 162.2, 133.9, 133.4, 122.6, 117.9, 113.7, 65.2, 61.0, 57.8, 55.3, 42.1, 34.0, 29.6, 27.7, 14.2.

Preparation 36

(αR)-Methyl 2-(4-methoxyphenyl)-α-(2-methylpropyl)-2-oxo-1,3,2-oxazaphosphorinane-3-acetate (diastereomer 1, compound 236).

General procedure 4.

Starting materials: 4-Methoxyphenylphosphonic dichloride and N-(3-hydroxypropyl)-D-leucine methyl ester.

$^{1}$H NMR (CDCl$_3$) δ 7.75 (m, 2H), 6.95 (m, 2H), 4.43 (m, 1H), 4.34 (m, 1H), 4.17 (m, 1H), 3.84 (s, 3H), 3.56 (s, 3H), 3.37 (m, 2H), 2.10-1.55 (m, 5H), 1.03 (d, 3H), 0.97 (d, 3H).

Preparation 37

(αR)-Methyl 2-(4-methoxyphenyl)-α-(2-methylpropyl)-2-oxo-1,3,2-oxazaphosphorinane-3-acetate (diastereomer 2, compound 237).

General procedure 4.

Starting materials: 4-Methoxyphenylphosphonic dichloride and N-(3-hydroxypropyl)-D-leucine methyl ester.

$^{13}$C NMR (CDCl$_3$) δ 173.7, 162.5, 133.8, 122.2, 113.9, 66.0, 55.4, 55.3, 52.0, 40.4, 38.5, 26.5, 24.5, 22.8, 21.5.

Preparation 38

(±)-Ethyl 2-(4-methoxyphenyl)-α-(2-methylpropyl)-2-oxo-1,3,2-oxazaphosphorepane-3-acetate (diastereomers 1, compound 238).

General procedure 6.

Starting materials: Compound 205 and ethyl 2-iodo-4-methylvaleroate.

$^{13}$C NMR (CDCl$_3$) δ 172.9, 162.1, 133.4, 122.5, 113.5, 65.3, 60.5, 57.3, 55.3, 43.8, 39.9, 29.8, 29.5, 24.9, 23.0, 22.0, 13.9.

Preparation 39

(±)-Ethyl 2-(4-methoxyphenyl)-α-(2-methylpropyl)-2-oxo-1,3,2-oxazaphosphorepane-3-acetate (diastereomers 2, compound 239).

General procedure 6.

Starting materials: Compound 205 and ethyl 2-iodo-4-methylvaleroate.

$^{13}$C NMR (CDCl$_3$) δ 173.6, 162.2, 133.2, 122.8, 113.7, 65.2, 60.9, 55.9, 55.3, 41.7, 38.4, 29.6, 27.7, 24.6, 22.7, 22.3, 14.2.

Preparation 40

(αS)-Methyl 2-(4-methoxyphenyl)-α-(2-methylpropyl)-2-oxo-1,3,2-oxazaphosphorinane-3-acetate (diastereomer 1, compound 240).

General procedure 4.

Starting materials: 4-Methoxyphenylphosphonic dichloride and N-(3-hydroxypropyl)-L-leucine methyl ester.

$^{13}$C NMR (CDCl$_3$) δ 173.5, 162.5, 133.8, 121.7, 113.9, 66.7, 55.7, 55.3, 51.6, 41.2, 38.6, 26.9, 24.7, 23.1, 21.7.

Preparation 41

(αS)-Methyl 2-(4-methoxyphenyl)-α-(2-methylpropyl)-2-oxo-1,3,2-oxazaphosphorinane-3-acetate (diastereomer 2, compound 241).

General procedure 4.

Starting materials: 4-Methoxyphenylphosphonic dichloride and N-(3-hydroxypropyl)-L-leucine methyl ester.

$^{13}$C NMR (CDCl$_3$) δ 173.7, 162.5, 133.9, 122.2, 113.9, 66.0, 55.4, 55.3, 52.0, 40.4, 38.5, 26.5, 24.5, 22.8, 21.5.

Preparation 42

(±)-Ethyl 2-(4-methoxyphenyl)-α-octyl-2-oxo-1,3,2-oxazaphosphorepane-3-acetate (diastereomers 1, compound 242).

General procedure 6.

Starting materials: Compound 205 and ethyl 2-iododecanoate.

$^{1}$H NMR (CDCl$_3$) δ 7.74 (m, 2H), 6.91 (m, 2H), 4.61 (m, 1H), 4.34 (m, 1H), 4.16 (m, 1H), 3.89 (dq, 2H), 3.82 (s, 3H), 3.20 (m, 1H), 3.07 (m, 1H), 2.02-1.10 (m, 18H), 0.98 (t, 3H), 0.88 (bt, 3H).

Preparation 43

(±)-Ethyl 2-(4-methoxyphenyl)-α-octyl-2-oxo-1,3,2-oxazaphosphorepane-3-acetate (diastereomers 2, compound 243).

General procedure 6.

Starting materials: Compound 205 and ethyl 2-iododecanoate.

$^{13}$C NMR (CDCl$_3$) δ 173.4, 162.2, 133.3, 122.7, 113.7, 65.2, 60.9, 57.8, 55.3, 41.6, 31.8, 29.6, 29.3, 29.2, 29.1, 27.7, 26.3, 22.6, 14.2, 14.1.

Preparation 44

(αS)-Ethyl 2-(4-methoxyphenyl)-2-oxo-α-phenylmethyl-1,3,2-oxazaphosphorinane-3-acetate (diastereomer 1, compound 244).

General procedure 4.

Starting materials: 4-Methoxyphenylphosphonic dichloride and N-(3-hydroxypropyl)-L-phenylalanine ethyl ester.

$^1$H NMR (CDCl$_3$) δ 7.75 (m, 2H), 7.35-7.16 (m, 5H), 6.93 (m, 2H), 4.58 (m, 1H), 4.29-4.02 (m, 2H), 3.95 (q, 2H), 3.83 (s, 3H), 3.54-3.26 (m, 3H), 3.14 (dd, 1H), 1.89 (m, 2H), 1.04 (t, 3H).

Preparation 45

(αS)-Ethyl 2-(4-methoxyphenyl)-2-oxo-α-phenylmethyl-1,3,2-oxazaphosphorinane-3-acetate (diastereomer 2, compound 245).

General procedure 4.

Starting materials: 4-Methoxyphenylphosphonic dichloride and N-(3-hydroxypropyl)-L-phenylalanine ethyl ester.

$^1$H NMR (CDCl$_3$) δ 7.23-7.05 (m, 7H), 6.70 (m, 2H), 4.60 (m, 1H), 4.50 (m, 1H), 4.21 (q, 2H), 4.12 (m, 1H), 3.81 (s, 3H), 3.60 (m, 1H), 3.20 (m, 2H), 2.91 (dd, 1H), 2.20 (m, 1H), 1.83 (m, 1H), 1.28 (t, 3H).

Preparation 46

(αR)-Methyl 2-(4-methoxyphenyl)-2-oxo-α-phenylmethyl-1,3,2-oxazaphosphorinane-3-acetate (diastereomer 1, compound 246).

General procedure 4.

Starting materials: 4-Methoxyphenylphosphonic dichloride and N-(3-hydroxypropyl)-D-phenylaianine methyl ester.

$^{13}$C NMR (CDCl$_3$) δ 172.2, 162.5, 136.8, 133.8, 129.4, 128.4, 126.7, 121.7, 113.9, 66.2, 58.5, 55.3, 51.6, 41.1, 36.3, 26.7.

Preparation 47

(αR)-Methyl 2-(4-methoxyphenyl)-2-oxo-α-phenylmethyl-1,3,2-oxazaphosphorinane-3-acetate (diastereomer 2, compound 247).

Starting materials: 4-Methoxyphenylphosphonic dichloride and N-(3-hydroxypropyl)-D-phenylalanine methyl ester.

$^{13}$C NMR (CDCl$_3$) δ 172.8, 162.1, 137.2, 133.5, 129.2, 128.7, 126.8, 121.4, 113.8, 66.5, 59.2, 55.3, 52.2, 41.0, 35.6, 26.2.

Preparation 48

(±)-Ethyl 2-oxo-2-(4-phenoxyphenyl)-1,3,2-oxazaphosghorinane-3-acetate (compound 248).

General procedure 4.

Starting materials: 4-Phenoxyphenylphosphonic dichloride and N-3-hydroxypropyl)glycine ethyl ester.

$^1$H NMR (CDCl$_3$) δ 7.85 (m, 2H), 7.38 (m, 2H), 7.18 (m, 1H), 7.04 (m, 4H), 4.50 (m, 1H), 4.23 (m, 1H), 4.14 (q, 2H), 4.02 (dd,1H), 3.68 (dd, 1H), 3.41 (m, 1H), 3.28 (m, 1H), 2.12 (m, 1H), 2.03 (m, 1H), 1.23 (t, 3H).

Preparation 49

(±)-Methyl 2-oxo-2-(4-phenoxyphenyl)-1,3,2-oxazaphosphorepane-3-acetate (compound 249).

General procedure 4.

Starting materials: 4-Phenoxyphenylphosphonic dichloride and N-(4-hydroxybutyl)glycine methyl ester.

$^1$H NMR (CDCl$_3$) δ 7.87 (m, 2H), 7.37 (m, 2H), 7.16 (m, 1H), 7.03 (m,4H), 4.54 (m, 1H), 4.37 (m, 1H), 4.15 (m, 1H), 3,85 (dd, 1H), 3.70 (s, 3H), 3.16 (m, 1H), 2.94 (m, 1H), 1.77 (m, 4H).

Preparation 50

(±)-Methyl 2-oxo-2-(4-phenoxyphenyl)-1,3,2-oxazaphosphorocane-3-acetate (compound 250).

General procedure 4.

Starting materials: 4-Phenoxyphenylphosphonic dichloride and N-(5-hydroxypentyl)glycine methyl ester.

$^{13}$C NMR (CDCl$_3$) δ 171.6, 160.6, 155.9, 133.5, 129.9, 124.7, 124.2, 119.9, 117.6, 66.1, 51.8, 46.0, 45.4, 28.6, 25.1, 24.4.

Preparation 51

(±)-Methyl α-allyl-2-oxo-2-(4-phenoxyphenyl)-1,3,2-oxazaphosphorinane-3-acetate (diastereomers 1, compound 251).

General procedure 4.

Starting materials: 4-Phenoxyphenylphosphonic dichloride and N-(3-hydroxypropyl)-(±)-allylglycine methyl ester.

$^{13}$C NMR (CDCl$_3$) δ 172.3, 160.9, 155.8, 134.1, 133.9, 130.0, 124.4, 124.3, 120.0, 118.0, 117.7, 66.9, 57.0, 51.8, 41.4, 34.4, 26.7.

Preparation 52

(±)-Methyl α-allyl-2-oxo-2-(4-phenoxyphenyl)-1,3,2-oxazaphosphorinane-3-acetate (diastereomers 2, compound 252).

General procedure 4.

Starting materials: 4-Phenoxyphenylphosphonic dichloride and N-(3-hydroxypropyl)-(±)-allylglycine methyl ester.

$^{13}$C NMR (CDCl$_3$) δ 172.6, 160.9, 155.8, 134.0, 134.0, 130.0, 124.6, 124.4, 119.9, 118.0, 117.6, 66.3, 57.3, 52.1, 40.8, 34.3, 26.3.

Preparation 53

(±)-Ethyl α-butyl-2-oxo-2-(4-phenoxyphenyl)-1,3,2-oxazaphosphorepane-3-acetate (diastereomers 1, compound 253).

General procedure 6.

Starting materials: Compound 206 and ethyl 2-iodohexanoate.

$^{13}$C NMR (CDCl$_3$) δ 172.6, 160.5, 156.0, 133.5, 129.9, 125.0, 124.2, 119.8, 117.5, 65.4, 60.5, 59.2, 43.9, 30.8, 29.8, 29.4, 28.7, 22.5, 14.0, 13.9.

Preparation 54

(±)-Ethyl α-butyl-2-oxo-2-(4-phenoxyphenyl)-1,3,2-oxazaphosphorepane-3-acetate (diastereomers 2, compound 254).

General procedure 6.

Starting materials: Compound 206 and ethyl 2-iodohexanoate.

$^{13}$C NMR (CDCl$_3$) δ 173.3, 160.5, 155.9, 133.4, 130.0, 125.2, 124.2, 119.8, 117.7, 65.3, 60.9, 57.8, 41.7, 29.6, 29.0, 28.5, 27.7, 22.3, 14.2, 13.8.

Preparation 55

(αR)-Methyl α-(2-methylpropyl)-2-oxo-2-(4-phenoxyphenyl)-1,3,2-oxazaphosphorinane-3-acetate (diastereomer 1, compound 255).

General procedure 4.

Starting materials: 4-Phenoxyphenylphosphonic dichloride and N-(3-hydroxypropyl)-D-leucine methyl ester.

$^{13}$C NMR (CDCl$_3$) δ 173.4, 160.8, 155.8, 133.9, 130.0, 124.3, 124.3, 119.9, 117.7, 66.9, 55.7, 51.7, 41.2, 38.6, 26.9, 24.7, 23.2, 21.7.

Preparation 56

(αR)-Methyl α-(2-methylpropyl)-2-oxo-2-(4-phenoxyphenyl)-1,3,2-oxazaphosphorinane-3-acetate (diastereomer 2, compound 256).

General procedure 4.

Starting materials: 4-Phenoxyphenylphosphonic dichloride and N-(3-hydroxypropyl)-D-leucine methyl ester.

$^{13}$C NMR (CDCl$_3$) δ 173.7, 160.9, 155.9, 133.9, 130.0, 124.9, 124.3, 119.8, 117.8, 66.1, 55.4, 52.0, 40.4, 38.4, 26.4, 24.5, 22.9, 21.5.

Preparation 57

(±)-Ethyl α-octyl-2-oxo-2-(4-phenoxyphenyl)-1,3,2-oxazaphosphorepane-3-acetate (diastereomers 1, compound 257).

General procedure 6.

Starting materials: Compound 206 and ethyl 2-iododecanoate.

$^{13}$C NMR (CDCl$_3$) δ 172.6, 160.4, 156.0, 133.5, 129.9, 125.0, 124.2, 119.8, 117.5, 65.4, 60.5, 59.3, 43.9, 31.9, 31.1, 29.8, 29.5, 29.3, 26.5, 22.7, 14.1, 13.9.

Preparation 58

(±)-Ethyl α-octyl-2-oxo-2-(4-phenoxyphenyl)-1,3,2-oxazaphosphorepane-3-acetate (diastereomers 2, compound 258).

General procedure 6.

Starting materials: Compound 206 and ethyl 2-iododecanoate.

MS. Calcd for C$_{28}$H$_{40}$NO$_5$P 501.26; Found [M+H]$^+$=502, [M+Na]$^+$=524.

Preparation 59

(αR)-Methyl α-(1-methylethyl)-2-oxo-2-(4-phenoxyphenyl)-1,3,2-oxazaphosphorinane-3-acetate (diastereomer 1, compound 259).

General procedure 4.

Starting materials: 4-Phenoxyphenyl phosphonic dichloride and N-(3-hydroxypropyl)-D-valine methyl ester.

$^{13}$C NMR (CDCl$_3$) δ 172.4, 160.7, 155.8, 133.6, 130.0, 124.9, 124.4, 119.9, 117.7, 66.8, 63.0, 51.1, 41.0, 27.2, 26.7, 19.4, 19.3.

Preparation 60

(±)-Ethyl 2-oxo-2-(2-phenylethyl)-1,3,2-oxazaphosphorinane-3-acetate (compound 260).

General procedure 6.

Starting materials: Compound 207 and ethyl bromoacetate.

$^1$H NMR (CDCl$_3$) δ 7.25 (m, 5H), 4.39 (m, 1H), 4.17 (m, 4H), 3.60 (dd, 1H), 3.44 (m, 1H), 3.05 (m, 1H), 2.17 (m, 3H), 1.90 (m, 1H), 1.61 (m, 1H), 1.36 (m, 1H), 1.26 (t, 3H).

Preparation 61

(±)- Methyl 2-(4-methoxyphenyl)-2-oxo-1,3,2-oxazaphosphorocane-3-acetate (compound 261).

General procedure 4.

Starting materials: 4-Methoxyphenylphosphonic dichloride and N-(5-hydroxypentyl)glycine methyl ester.

$^{13}$C NMR (CDCl$_3$) δ 171.7, 162.2, 133.3, 122.2, 113.7, 66.0, 55.3, 51.8, 46.2, 45.4, 28.7, 25.2, 24.4.

Preparation 62

(±)-Methyl 2-oxo-2-phenyl-1,3,2-oxazaphosphorocane-3-acetate (compound 262).

General procedure 4.

Starting materials: Phenylphosphonic dichloride and N-(5-hydroxypentyl)glycine methyl ester.

$^{13}$C NMR (CDCl$_3$) δ 171.6, 131.6, 131.4, 130.8, 128.2, 66.2, 51.8, 46.2, 45.4, 28.7, 25.1, 24.4.

Preparation 63

(±)-Methyl 2-heptyl-2-oxo-1,3,2-oxazaphosphorocane-3-acetate (compound 263).

General procedure 4.

Starting materials: n-Heptylphosphonic dichloride and N-(5-hydroxypentyl)glycine methyl ester.

$^{13}$C NMR (CDCl$_3$) δ 171.9, 65.9, 51.8, 46.0, 44.8, 31.7, 30.9, 28.9, 28.6, 27.1, 25.2, 24.5, 22.6, 22.5, 14.1.

Preparation 64

(αR)-Methyl 2-(4-biphenylyl)-α-(1-methylethyl)-2-oxo-1,3,2-oxazaphosphorinane-3-acetate (diastereomer 1, compound 264).

General procedure 4.

Starting materials: 4-Biphenylylphosphonic dichloride and N-(3-hydroxypropyl)-D-valine methyl ester.

$^1$H NMR (CDCl$_3$) δ 7.78 (m, 2H), 7.66 (m, 2H), 7.60 (m, 2H), 7.46 (m, 2H), 7.39 (m, 1H), 4.48 (m, 1H), 4.27 (m, 1H), 3.92 (t, 1H), 3.74 (m, 1H), 3.60-3.30 (m, 1H), 3.42 (s, 3H), 2.21 (m, 2H), 1.99 (m, 1H), 1.16 (d, 3H), 0.92 (d, 3H).

Preparation 65

(αR)-Methyl 2-(4-biphenylyl)-α-(1-methylethyl)-2-oxo-1,3,2-oxazaphosphorinane-3-acetate (diastereomer 2, compound 265).

General procedure 4.

Starting materials: 4-Biphenylylphosphonic dichloride and N-(3-hydroxypropyl)-D-valine methyl ester.

$^1$H NMR (CDCl$_3$) δ 7.90 (m, 2H), 7.68 (m, 2H), 7.61 (m, 2H), 7.47 (m, 2H), 7.39 (m, 1H), 4.53 (m, 1H), 4.30 (m, 1H), 3.82-3.66 (m, 1H), 3.78 (s, 3H), 3.60 (dd, 1H), 3.26 (m, 1H), 2.12 (m, 2H), 1.84 (m, 1H), 0.83 (d, 3H), 0.73 (d, 3H).

Preparation 66

(αR)-Methyl 2-(4-biphenylyl)-2-oxo-α-phenylmethyl-1,3,2-oxazaphosphorinane-3-acetate (diastereomer 1, compound 266).

General procedure 4.

Starting materials: 4-Biphenylylphosphonic dichloride and N-(3-hydroxypropyl)-D-phenylalanine methyl ester.

$^1$H NMR (CDCl$_3$) δ 7.85 (m, 2H), 7.65 (m, 2H), 7.59 (m, 2H), 7.45 (m,3H), 7.37-7.16 (m, 5H), 4.72 (m, 1H), 4.30-4.05 (m, 2H), 3.53-3.30 (m, 3H), 3.48 (s, 3H), 3.16 (dd, 1H), 1.91 (m, 2H).

Preparation 67

(αR)-Methyl 2-(4-biphenylyl)-2-oxo-α-phenylmethyl-1,3,2-oxazaphosphorinane-3-acetate (diastereomer 2, compound 267).

General procedure 4.

Starting materials: 4-Biphenylylphosphonic dichloride and N-(3-hydroxypropyl)-D-phenylalanine methyl ester.

$^1$H NMR (CDCl$_3$) δ 7.56 (m, 2H), 7.47 (m, 2H), 7.40 (m, 3H), 7.25-7.15 (m,5H), 7.10 (m, 2H), 4.72 (m, 1H), 4.54 (m, 1H), 4.25-4.07(m, 1H), 3.78 (s, 3H), 3.60 (m, 1H), 3.24 (m, 2H), 2.94 (dd, 1H), 2.23 (m, 1H), 1.88 (m, 1H).

Preparation 68

(±)-Ethyl 2-[4-(4-chlorophenyloxy)-phenyl]-2-oxo-1,3,2-oxazaphosphorepane-3-acetate (compound 268).

General procedure 4.

Starting materials: 4-(4-Chlorophenoxy)phenylphosphonic dichloride and N-(4-hydroxybutyl)glycine methyl ester.

$^{13}$C NMR (CDCl$_3$) δ 171.3, 160.1, 154.6, 133.5, 130.0, 129.3, 125.1, 121.1, 117.8, 65.3, 61.0, 48.4, 47.3, 29.5, 26.5, 14.2.

Preparation 69

(±)-Ethyl 2-[4-(4-chlorophenyloxy)-phenyl]-2-oxo-1,3,2-oxazaphosphorocane-3-acetate (compound 269).

General procedure 4.

Starting materials: 4-(4-Chlorphenoxy)phenylphosphonic dichloride and N-(5-hydroxypentyl)glycine methyl ester.

$^1$H NMR (CDCl$_3$) δ 7.94 (m, 2H), 7.32 (m, 2H), 7.05-6.94 (m, 4H), 4.47 (m, 2H), 4.16 (dq, 2H), 4.04 (m, 1H), 3.71 (dd, 1H), 3.18 (m, 1H), 3.03 (m, 1H), 2.00-1.56 (m, 5H), 1.44 (m, 1H), 1.24 (t, 3H).

Preparation 70

(±)-Ethyl 2-(4'-bromo-4-biphenylyl)-2-oxo-1,3,2-oxazaphosphorinane-3-acetate (compound 270).

General procedure 4.

Starting materials: 4'-Bromo-4-biphenylylphosphonic dichloride and N-(3-hydroxypropyl)glycine ethyl ester.

$^1$H NMR (CDCl$_3$) δ 7.95 (m, 2H), 7.72-7.42 (m, 6H), 4.53 (m, 1H), 4.26 (m, 1H), 4.15 (q, 2H), 4.06 (dd, 1H), 3.74 (dd, 1H), 3.47 (m, 1H), 3.31 (m, 1H), 2.16 (m, 1H), 2.03 (m, 1H), 1.23 (t, 3H).

Preparation 71

(±)-Ethyl 2-(4'-bromo-4-biphenylyl)-2-oxo-1,3,2-oxazaphosphorepane-3-acetate (compound 271).

General procedure 4.

Starting materials: 4'-Bromo-4-biphenylylphosphonic dichloride and N-(4-hydroxybutyl)glycine ethyl ester.

$^{13}$C NMR (CDCl$_3$) δ 171.3, 143.1, 139.2, 132.0, 131.9, 129.8, 128.8, 126.8, 122.3, 65.4, 61.0, 48.6, 47.4, 29.5, 26.6, 14.2.

Preparation 72

(±)-Methyl 2-(4'-bromo-4-biphenylyl)-2-oxo-1,3,2-oxazaphosphorocane-3-acetate (compound 272).

General procedure 4.

Starting materials: 4'-Bromo-4-biphenylylphosphonic dichloride and N-(5-hydroxypentyl)glycine methyl ester.

$^1$H NMR (CDCl$_3$) δ 8.02 (m, 2H), 7.63 (m, 2H), 7.58 (m, 2H), 7.47 (m, 2H), 4.50 (m, 2H), 4.07 (m, 1H), 3.77 (m, 1H), 3.71 (s, 3H), 3.23 (m, 1H), 3.05 (m, 1H), 2.00-1.33 (m, 6H).

Preparation 73

(±)-Ethyl 2-oxo-2-[2-(1-naphtyl)-ethyl]-1,3,2-oxazaphosphorinane-3-acetate (compound 273).

General procedure 4.

Starting materials: 2-(1-naphtyl)ethylphosphonic dichloride and N-(3-hydroxypropyl)glycine ethyl ester.

$^{13}$C NMR (CDCl$_3$) δ 170.7, 137.6, 133.9, 131.5, 128.9, 127.0, 126.1, 125.7, 125.6, 123.5, 67.0, 61.1, 49.8, 47.2, 28.4, 26.2, 25.9, 14.2.

Preparation 74

(±)-Ethyl 2-phenyl-2-thioxo-1,3,2-oxazaphosphorinane-3-acetate (compound 274).

General procedure 4.

Starting materials: Thio-phenylphosphonic dichloride and N-(3-hydroxypropyl)glycine ethyl ester.

$^{13}$C NMR (CDCl$_3$) δ 170.2, 132.7, 132.4, 131.7, 128.6, 66.3, 61.0, 50.8, 47.0, 26.3, 14.2.

Preparation 75

(±)-Ethyl 2-phenyl-2-thioxo-1,3,2-oxazaphosphorepane-3-acetate (compound 275).

General procedure 4.

Starting materials: Thio-phenylphosphonic dichloride and N-(4-hydroxybutyl)glycine ethyl ester.

$^{13}$C NMR (CDCl$_3$) δ 171.3, 135.4, 131.3, 130.5, 128.2, 64.7, 61.0, 49.9, 47.9, 29.1, 25.7, 14.2.

Preparation 76

(±)-Methyl 2-phenyl-2-thioxo-1,3,2-oxazaphosphorocane-3-acetate (compound 276).

General procedure 4.

Starting materials: Thio-phenylphosphonic dichloride and N-(5-hydroxypentyl)glycine methyl ester.

$^{13}$C NMR (CDCl$_3$) δ 171.5, 135.7, 131.2, 130.6, 128.2, 66.0, 51.9, 46.9, 45.4, 28.3, 25.0, 24.2.

Preparation 77

(±)-Ethyl 2-[4-(4-chlorophenyloxy)-phenyl]-2-oxo-1,3,2-oxazaphosphorinane-3-acetate (compound 277).

General procedure 4.

Starting materials: 4-(4-chlorophenoxy)phenylphosphonic dichloride and N-(3-hydroxypropyl)glycine ethyl ester.

$^{13}$C NMR (CDCl$_3$) δ 170.3, 160.6, 154.4, 134.2, 130.0, 129.5, 124.5, 121.2, 117.8, 66.9, 61.1, 49.3, 47.3, 26.1, 14.2.

Preparation 78

(αR)-Methyl 2-[4-(4-chlorophenoxy)-phenyl]-α-(2-methylethyl)-2-oxo-1,3,2-oxazaphosphorinane-3-acetate (diastereomer 1, compound 278).

General procedure 4.

Starting materials: 4-(4-Chlorophenoxy)phenylphosphonic dichloride and N-(3-hydroxypropyl)-D-valine methyl ester.

$^{13}$C NMR (CDCl$_3$) δ 172.3, 160.3, 154.5, 133.6, 130.0, 129.5, 125.5, 121.1, 117.8, 66.8, 63.1, 51.1, 41.0, 27.2, 26.7, 19.4, 19.3.

Preparation 79

(αR)-Methyl 2-[4-(4-chlorophenoxy)-phenyl]-α-(2-methylethyl)-2-oxo-1,3,2-oxazaphosphorinane-3-acetate (diastereomer 2, compound 279).

General procedure 4.

Starting materials: 4-(4-chlorophenoxy) phenylphosphonic dichloride and N-(3-hydroxypropyl)-D-valine methyl ester.

$^{13}$C NMR (CDCl$_3$) δ 173.0, 160.6, 154.4, 134.5, 130.0, 129.6, 124.3, 121.2, 117.6, 66.0, 63.4, 51.8, 40.2, 27.6, 26.5, 19.6, 19.4.

Preparation 80

(±)-Ethyl 2-(4-bromophenyl)-2-oxo-1,3,2-oxazaphosphorinane-3-acetate (compound 280).

General procedure 4.

Starting materials: 4-Bromophenylphosphonic dichloride and N-(3-hydroxypropyl)glycine ethyl ester.

(CDCl$_3$) δ 7.75 (m, 2H), 7.60 (m, 2H), 4.50 (m, 1H), 4.22 (m, 1H), 4.14 (q, 2H), 4.04 (dd, 1H), 3.68 (dd, 1H), 3.42 (m, 1H), 3.27 (m, 1H), 2.14 (m, 1H), 2.00 (m, 1H), 1.23 (t, 3H).

Preparation 81

(±)-Ethyl 2-(4-bromophenyl)-2-oxo-1,3,2-oxazaphosphorepane-3-acetate (compound 281).

General procedure 4.

Starting materials: 4Bromophenylphosphonic dichloride and N-(4-hydroxybutyl)glycine ethyl ester.

$^{13}$C NMR (CDCl$_3$) δ 171.2, 132.9, 131.5, 129.7, 126.6, 65.4, 61.1, 48.5, 47.4, 29.4, 26.5, 14.2.

Preparation 82

(±)-Ethyl 2-[4-(phenylmethoxy)phenyl]-2-oxo-1,3,2-oxazaphosphorinane-3-acetate (compound 282).

General procedure 4.

Starting materials: 4-(Phenylmethoxy)phenylphosphonic dichloride and N-(3-hydroxypropyl)glycine ethyl ester.

$^{13}$C NMR (CDCl$_3$) δ 170.4, 161.8, 136.3, 134.1, 128.7, 128.2, 127.5, 121.6, 114.9, 70.0, 66.7, 61.0, 49.3, 47.2, 26.1, 14.1.

Preparation 83

(±)-Ethyl 2-[4-(phenylmethoxy)phenyl]-2-oxo-1,3,2-oxazaphosphorepane-3-acetate (compound 283).

General procedure 4.

Starting materials: 4-(Phenylmethoxy)phenylphosphonic dichloride and N-(4-hydroxybutyl)glycine ethyl ester.

$^{13}$C NMR (CDCl$_3$) δ 171.4, 161.4, 136.5, 133.2, 128.7, 128.1, 127.5, 122.4, 114.7, 70.0, 65.2, 61.0, 48.6, 47.4, 29.5, 26.5, 14.2.

Preparation 84

(±)-Ethyl 2-[4-(phenylmethoxy)phenyl]-2-oxo-1,3,2-oxazaphosphorocane-3-acetate (compound 284).

General procedure 4.

Starting materials: 4-(Phenylmethoxy)phenylphosphonic dichloride and N-(5-hydroxypentyl)glycine ethyl ester.

$^1$H NMR (CDCl$_3$) δ 7.89 (m, 2H), 7.45-7.28 (m, 5H), 7.02 (m, 2H), 5.10 (s, 2H), 4.45 (m, 2H), 4.15 (dq, 2H), 4.02 (m, 1H), 3.71 (dd, 1H), 3.16 (m, 1H), 3.01 (m, 1H), 2.00-1.60 (m, 5H), 1.43 (m, 1H), 1.23 (t, 3H).

Preparation 85

(±)-Ethyl 2-oxo-2-[4-(4-trifluoromethylphenoxy)phenyl]-1,3,2-oxazaphosphorinane-3-acetate (compound 285).

General procedure 4.

Starting materials: 4-(Trifluoromethylphenoxy) phenylphosphonic dichloride and N-(3-hydroxypropyl) glycine ethyl ester.

$^1$H NMR (CDCl$_3$) δ 7.91 (m, 2H), 7.62 (m, 2H), 7.14-7.05 (m, 4H), 4.52 (m, 1H), 4.24 (m, 1H), 4.15 (q, 2H), 4.06 (dd, 1H), 3.70 (dd, 1H), 3.45 (m, 1H), 3.29 (m, 1H), 2.14 (m, 1H), 2.03 (m, 1H), 1.24 (t, 3H).

Preparation 86

(±)-Ethyl 2-oxo-2-[4-(4-trifluoromethylphenoxy)phenyl]-1 3,2-oxazaphosphorepane-3-acetate (compound 286).

General procedure 4.

Starting materials: 4-(Trifluoromethylphenoxy) phenylphosphonic dichloride and N-(4-hydroxybutyl) glycine ethyl ester.

$^{13}$C NMR (CDCl$_3$) δ 171.4, 159.3, 159.0, 133.6, 127.3, 126.2, 119.0, 118.9, 65.4, 61.1, 48.4, 47.4, 29.5, 26.5, 14.2.

Preparation 87

(αR)-Methyl α-(2-methylethyl)-2-oxo-2-[4-(4-trifluoromethylphenoxy)phenyl]-1,3,2-oxazaphosphorinane-3-acetate (diastereomer 1, compound 287).

General procedure 4.

Starting materials: 4-(trifluoromethylphenoxy) phenylphosphonic dichloride and N-(3-hydroxypropyl)-D-valine methyl ester.

$^{13}$C NMR (CDCl$_3$) δ 172.3, 159.2, 159.1, 133.8, 127.4, 126.7, 126.0, 124.1, 119.0, 118.9, 66.9, 63.1, 51.1, 41.0, 27.2, 26.7, 19.4, 19.3.

Preparation 88

(αR)-Methyl α-(2-methylethyl)-2-oxo-2-[4-(4-trifluoromethylphenoxy)phenyl]-1,3,2-oxazaphosphorinane-3-acetate (diastereomer 2, compound 288).

General procedure 4.

Starting materials: 4-(Trifluoromethylphenoxy) phenylphosphonic dichloride and N-(3-hydroxypropyl)-D-valine methyl ester.

$^{13}$C NMR (CDCl$_3$) δ 173.0, 159.5, 159.0, 134.6, 127.4, 126.1, 125.6, 124.1, 119.2, 118.7, 66.1, 63.5, 51.8, 40.2, 27.6, 26.5, 19.7, 19.4.

Preparation 89

(±)-Ethyl 2-[4-(4-bromophenoxy)-phenyl]-2-oxo-1,3,2-oxazaphosphorinane-3-acetate (compound 289).

General procedure 4.

Starting materials: 4-(4-Bromophenoxy) phenylphosphonic dichloride and N-(3-hydroxypropyl) glycine ethyl ester.

$^{13}$C NMR (CDCl$_3$) δ 170.3, 160.5, 155.0, 134.2, 133.0, 124.7, 121.6, 117.9, 117.0, 66.9, 61.1, 49.3, 47.3, 26.1, 14.2.

Preparation 90

(±)-Ethyl 2- [4-(4-bromophenoxy)-phenyl]-2-oxo-1,3,2-oxazaphosphorepane-3-acetate (compound 290).

General procedure 4.

Starting materials: 4-(4-Bromophenoxy) phenylphosphonic dichloride and N-(4-hydroxybutyl) glycine ethyl ester.

$^{13}$C NMR (CDCl$_3$) δ 171.4, 160.0, 155.3, 133.5, 132.9, 125.2, 121.4, 117.9, 116.7, 65.3, 61.0, 48.4, 47.3, 29.5, 26.5, 14.2.

Preparation 91

(±)-Ethyl 2-(4-nitrophenyl)-2-oxo-1 3,2-oxazaphosphorepane-3-acetate (compound 291).

General procedure 4.

Starting materials: 4-Nitrophenylphosphonic dichloride and N-(4-hydroxybutyl)glycine ethyl ester.

$^{13}$C NMR (CDCl$_3$) δ 171.1, 149.8, 138.0, 132.6, 123.1, 65.9, 61.3, 48.4, 47.4, 29.4, 26.6, 14.2.

Preparation 92

(±)-Ethyl 2-[N-(4-chlorobenzoyl)-4-aminophenyl]-2-oxo-1,3,2-oxazaphosphorepane-3-acetate (compound 292).

Procedure: A solution of compound 291 in methanol was hydrogenated with Pd on carbon (10%) for 1 hour at atm. pressure. Filtration and concentration afforded ethyl 2-(4-aminophenyl)-2-oxo-1,3,2-oxazaphosphorepane-3-acetate. This crude aniline was dissolved in CH$_2$Cl$_2$ with 3 equivalents triethylamine, the solution was cooled to 0° C., and 2 equivalents of 4-chlorobenzoylchloride were added neat. After stirring overnight at r.t., the mixture was concentrated under reduced pressure, redissolved in ethylacetat and washed with water and brine. After filtration and evaporation, the title compound was purified by flash chromatography.

$^{13}$C NMR (CDCl$_3$) δ 171.2, 165.3, 141.6, 138.0, 133.1, 132.0, 129.2, 128.7, 125.3, 120.3, 65.4, 61.1, 48.8, 47.4, 29.4, 26.5, 14.2.

Preparation 93

(±)-Ethyl 2-(N-benzoyl-4-aminophenyl)-2-oxo-1,3,2-oxazaphosphorepane-3-acetate (compound 293).

Procedure: Similar to preparation 92, except that benzoylchloride was used instead of 4-chlorobenzoylchloride.

$^{13}$C NMR (CDCl$_3$) δ 171.3, 166.1, 141.4, 134.7, 132.3, 131.9, 128.6, 127.4, 125.5, 119.9, 65.3, 61.0, 48.7, 47.4, 29.5, 26.5, 14.2.

Preparation 94

(αR)-Methyl α-(2-methylethyl)-2-oxo-2-(4-phenoxyphenyl)-1,3,2-oxazaphosphorinane-3-acetate (diastereomer 1, compound 294).

General procedure 4.

Starting materials: 4-Phenoxyphenylphosphonic dichloride and N-(3-hydroxypropyl)-D-valine methyl ester.

$^{13}$C NMR (CDCl$_3$) δ 173.0, 161.1, 155.7, 134.4, 130.0, 124.4, 123.6, 120.0, 117.5, 66.0, 63.4, 51.7, 40.2, 27.5, 26.5, 19.6, 19.4.

Preparation 95

(±)-Ethyl α-butyl-2-(4-methoxyphenyl)-2-oxo-1,3,2-oxazaphosphorinane-3-acetate (diastereomers 1, compound 295).

General procedure 4.

Starting materials: 4-Methoxyphenylphosphonic dichloride and N-(3-hydroxypropyl)-(±)-norleucine ethyl ester.

$^{13}$C NMR (CDCl$_3$) δ 172.7, 162.5, 133.9, 121.8, 113.9, 66.8, 60.7, 57.6, 55.3, 41.2, 29.4, 28.4, 26.9, 22.4, 14.1, 13.9.

Preparation 96

(±)-Ethyl α-butyl-2-(4-methoxyphenyl)-2-oxo-1,3,2-oxazaphosphorinane-3-acetate (diastereomers 2, compound 296).

General procedure 4.

Starting materials: 4-Methoxyphenylphosphonic dichloride and N-(3-hydroxypropyl)-(±)-norleucine ethyl ester.

$^{13}$C NMR (CDCl$_3$) δ 173.1, 162.5, 133.8, 122.4, 113.9, 65.9, 60.9, 57.3, 55.3, 40.2, 29.1, 28.4, 26.5, 22.1, 14.2, 13.8.

Preparation 97

(±)-Ethyl 2-oxo-2-phenyl-1,3,2-oxazaphosphoronane-3-acetate (compound 297).

General procedure 4.

Starting materials: Phenylphosphonic dichloride and N-(5-hydroxypentyl)glycine methyl ester.

$^{13}$C NMR (CDCl$_3$) δ 171.1, 131.9, 131.7, 130.4, 128.2, 60.9, 60.6, 45.9, 42.3, 27.7, 24.4, 19.1, 18.4, 14.2.

Preparation 100

(αR)-2-(4-Methoxyphenyl)-α-(1-methylethyl)-2-oxo-1,3,2-oxazaphosphorinane-3-acetic acid (diastereomer 1, compound 300).

General procedure 3.

Starting materials: Compound 226.

$^{1}$H NMR (CD$_3$OD) δ 7.72 (m,2H), 7.07 (m, 2H), 4.46 (m, 1H), 4.27 (m,1H), 3.89 (s, 3H), 3.73 (t,1H), 3.67-3.36 (m, 2H), 2.21 (m, 2H), 1.98 (m, 1H), 1.16 (d, 3H), 1.02 (d, 3H).

Preparation 101

(αR)-2-(4-Methoxyphenyl)-α-(1-methylethyl)-2-oxo-1,3,2-oxazaphosphorinane-3-acetic acid (diastereomer 2, compound 301).

General procedure 3.

Starting materials: Compound 227.

$^{1}$H NMR (CD$_3$OD) δ 7.86 (m,2H), 6.98 (m, 2H), 4.50 (m, 1H), 4.33 (m,1H), 3.84 (s, 3H), 3.51 (m,1H), 3.37-3.10 (m, 2H), 2.13 (m, 3H), 0.81 (d, 3H), 0.54 (d, 3H).

Preparation 102

(αR)-2-(4-Biphenylyl)-α-(1-methylethyl)-2-oxo-1,3,2-oxazaphosphorinane-3-acetic acid (diastereomer 1, compound 302).

General procedure 3.

Starting materials: Compound 264.

$^{1}$H NMR (CD$_3$OD) δ 8.06 (m, 2H), 7.55 (bs, 4H), 7.35 (bs, 3H), 4.47 (m, 2H), 3.41 (m, 1H), 3.23 (m, 1H), 2.18 (m, 3H), 0.88 (bd, 3H), 0.45 (d, 3H).

Preparation 103

(αR)-2-(4-Biphenylyl)-2-oxo-α-phenylmethyl-1,3,2-oxazaphosphorinane-3-acetic acid (diastereomer 1, compound 303).

General procedure 3.

Starting materials: Compound 266.

$^{1}$H NMR (CD$_3$OD) δ 7.87 (m, 2H), 7.73 (m, 2H), 7.65 (m, 2H), 7.46 (m, 2H), 7.42-7.25 (m, 5H), 7.21 (m, 1H), 4.60 (m, 1H), 4.16 (m, 2H), 3.60-3.28 (m, 3H), 3.14 (dd, 1H), 1.90 (m, 2H).

Preparation 104

(αR)-2-(4-Biphenylyl)-2-oxo-α-phenylmethyl-1,3,2-oxazaphosphorinane-3-acetic acid (diastereomer 2, compound 304).

General procedure 3.
Starting materials: Compound 267.
$^1$H NMR (CD$_3$OD) δ 7.54 (m, 2H), 7.49-7.25 (m, 7H), 6.99 (m, 3H), 6.89 (m, 2H), 4.51 (m, 1H), 4.18 (m, 2H), 3.71-3.28 (m, 2H), 3.14 (m, 1H), 2.85 (dd, 1H), 2.14 (m, 2H).

Preparation 105

(±)-2-Oxo-2-phenyl-1,3,2-oxazaphosphorepane-3-acetic acid (compound 305)

General procedure 3.
Starting materials: Compound 220.
$^{13}$C NMR (DMSO-d$_6$) δ 172.4, 131.3, 131.2, 130.8, 128.1, 64.7, 47.8, 46.9, 28.9, 25.9.

Preparation 106

(±)-2-Oxo-2-phenyl-1,3,2-oxazaphosphorocane-3-acetic acid (compound 306)

General procedure 3.
Starting material : Compound 262.
$^{13}$C NMR (DMSO-d$_6$) δ 172.2, 131.4, 131.3, 130.9, 128.1, 65.3, 45.8, 45.3, 27.9, 24.6, 24.0.

Preparation 107

(±)-α-Butyl-2-oxo-2-phenyl-1,3,2-oxazaphosphorepane-3-acetic acid (diastereomers 1, compound 307)

General procedure 3.
Starting materials: Compound 221.
$^{13}$C NMR (CD$_3$OD) δ 175.3, 132.9, 132.6, 131.5, 129.3, 67.3, 61.0, 45.9, 31.9, 30.6, 30.5, 30.1, 23.5, 14.3.

Preparation 108

(±)-α-Butyl-2-oxo-2-phenyl-1,3,2-oxazaphosphorepane-3-acetic acid (diastereomers 2, compound 308)

General procedure 3.
Starting materials: Compound 222.
$^1$H NMR (CD$_3$OD) δ 7.84 (m, 2H), 7.62 (m, 1H), 7.54 (m, 2H), 4.79 (m, 1H), 4.33 (m, 1H), 4.25 (m, 1H), 3.23 (m, 1H), 3.06 (m, 1H), 1.96 (m, 3H), 1.85 (m, 1H), 1.72 (m, 1H), 1.55 (m, 1H), 1.23 (m, 2H), 1.00 (m, 2H), 0.77 (t, 3H).

Preparation 109

(±)-2-(4-Methoxyphenyl)-2-oxo-1,3,2-oxazaphosphorinane-3-acetic acid (compound 309).

General procedure: 3.
Starting material: Compound 223.
$^{13}$C NMR (CD$_3$OD) δ 176.0, 164.8, 135.5, 115.3, 68.5, 56.0, 27.2.

Preparation 110

(±)-2-(4-Methoxyphenyl)-2-oxo-1,3,2-oxazaphosphorepane-3-acetic acid (compound 310).

General procedure: 3.
Starting material: Compound 224.

Preparation 111

(±)-α-Butyl-2-(4-methoxyphenyl)-2-oxo-1,3,2-oxazaphosphorinane-3-acetic acid (diastereomers 1, compound 311).

General procedure: 3.
Starting material: Compound 295.
$^{13}$C NMR (DMSO-d$_6$) δ 173.6, 161.6, 133.0, 122.5, 113.9, 67.1, 56.8, 55.2, 41.1, 28.6, 27.9, 26.4, 21.6, 13.8.

Preparation 112

(±)-α-Butyl-2-(4-methoxyphenyl)-2-oxo-1,3,2-oxazaphosphorinane-3-acetic acid (diastereomers 2 compound 312).

General procedure: 3.
Starting material: Compound 296.
$^{13}$C NMR (CDCl$_3$) δ 172.6, 163.7, 135.1, 118.0, 114.1, 66.5, 57.9, 55.5, 40.8, 27.8, 26.9, 26.1, 22.0, 13.8.

Preparation 113

(±)-α-Butyl-2-(4-methoxyphenyl)-2-oxo-1,3,2-oxazaphosphorepane-3-acetic acid (diastereomers 1, compound 313).

General procedure: 3.
Starting material: Compound 228.
$^1$H NMR (DMSO-d$_6$) δ 7.63 (m, 2H), 6.98 (m, 2H), 4.45 (q, 1H), 4.11 (m, 1H), 4.03 (m, 1H), 3.79 (s, 3H), 3.20-2.90 (m, 2H), 1.90-1.20 (m, 1OH), 0.87 (bt, 3H).

Preparation 114

(±)-α-Butyl-2-(4-methoxyphenyl)-2-oxo-1 3,2-oxazaphosphorepane-3-acetic acid (diastereomers 2, compound 314).

General procedure: 3.
Starting material: Compound 229.
$^1$H NMR (DMSO-d6) δ 7.65 (m, 2H), 7.01 (m, 2H), 4.55 (q, 1H), 4.05 (m, 2H), 3.80 (s, 3H), 3.09 (m, 1H), 2.84 (m, 1H), 1.90-1.20 (m, 6H), 1.10 (m, 2H), 0.86 (m, 2H), 0.67 (t, 3H).

Preparation 115

(±)-α-Butyl-2-(4-methoxyphenyl)-2-oxo-1,3,2-oxazaphosphorocane-3-acetic acid (diastereomers 1, compound 315).

General procedure: 3.
Starting material: Compound 230.
MS. Calcd for C$_{18}$H$_{28}$NO$_5$P 369.17, Found [M+H]$^+$=370, [M−H]$^-$=368.

Preparation 116

(±)-α-Butyl-2-(4-methoxyphenyl)-2-oxo-1,3,2-oxazaphosphorocane-3-acetic acid (diastereomers 2, compound 316).

General procedure: 3.
Starting material: Compound 231.
MS. Calcd for C$_{18}$H$_{28}$NO$_5$P 369.17, Found [M+H]$^+$=370, [M−H]$^-$=368.

Preparation 117

(±)-α-Allyl-2-(4-methoxyphenyl)-2-oxo-1 3,2-oxazaphosphorinane-3-acetic acid (diastereomers 1, compound 317).

General procedure: 3.
Starting material: Compound 232.
$^1$H NMR (CD$_3$OD) δ 7.78 (m, 2H), 7.02 (m, 2H), 5.95 (m, 1H), 5.20 (m, 1H), 5.12 (m, 1H), 4.38 (m, 1H), 4.20 (m, 2H), 3.85 (s, 3H), 3.38 (m, 2H), 2.66 (m, 2H), 2.06 (m, 1H), 1.91 (m, 1H).

Preparation 118

(±)-α-Allyl-2-(4-methoxyphenyl)-2-oxo-1,3,2-oxazaphosphorinane-3-acetic acid (diastereomers 2, compound 318).

General procedure: 3.

Starting material: Compound 233.

$^1$H NMR (CD$_3$OD) δ 7.73 (m, 2H), 7.04 (m, 2H), 5.47 (m, 1H), 5.02 (m, 1H), 4.89 (bd, 1H), 4.52 (m, 1H), 4.30 (m, 1H), 4.05 (m, 1H), 3.86 (s, 3H), 3.31 (m, 1H), 3.26 (m, 1H), 2.56 (m, 1H), 2.41 (m, 1H), 2.21 (m, 1H), 2.03 (m, 1H).

Preparation 119

(αR)-2-(4-Methoxyphenyl)-α-(2-methylpropyl)-2-oxo-1,3,2-oxazaphosphorinane-3-acetic acid (diastereomer 1, compound 319).

General procedure: 3.

Starting material: Compound 236.

$^1$H NMR (CD$_3$OD) δ 7.82 (m, 2H), 7.07 (m, 2H), 4.46 (m, 1H), 4.23 (m, 2H), 3.89 (s, 3H), 3.43 (m, 2H), 2.04 (m, 2H), 1.84 (m, 2H), 1.69 (m, 1H), 1.05 (d, 3H), 1.03 (d, 3H).

Preparation 120

(αR)-2-(4-Methoxyphenyl)-α-(2-methylpropyl)-2-oxo-1,3,2-oxazaphosphorinane-3-acetic acid (diastereomer 2, compound 320).

General procedure: 3.

Starting material: Compound 237.

$^1$H NMR (CD$_3$OD) δ 7.79 (m, 2H), 7.09 (m, 2H), 4.58 (m, 1H), 4.36 (m, 1H), 4.01 (m, 1H), 3.90 (s, 3H), 3.57 (m, 1H), 3.31 (m, 1H), 2.27 (m, 1H), 2.14 (m, 1H), 1.62 (m, 2H), 1.42 (m, 1H), 0.82 (d, 3H), 0.59 (d, 3H).

Preparation 121

(±)-2-(4-Methoxyphenyl)-α-(2-methylpropyl)-2-oxo-1,3,2-oxazaphosphorepane-3-acetic acid (diastereomers 1, compound 321).

General procedure: 3.

Starting material: Compound 238.

$^1$H NMR (CD$_3$OD) δ 7.72 (m, 2H), 6.98 (m, 2H), 4.58 (m, 1H), 4.30 (m, 1H), 4.18 (m, 1H), 3.83 (s, 3H), 3.21 (m, 1H), 3.10 (m, 1H), 2.03-1.55 (m, 7H), 1.03 (d, 3H), 0.98 (d, 3H).

Preparation 122

(±)-2-(4-Methoxyphenyl)-α-(2-methylpropyl)-2-oxo-1,3,2-oxazaphosphorepane-3-acetic acid (diastereomers 2, compound 322).

General procedure: 3.

Starting material: Compound 239.

$^1$H NMR (CD$_3$OD) δ 7.72 (m, 2H), 7.03 (m, 2H), 4.72 (m, 1H), 4.35 (m, 1H), 4.16 (m, 1H), 3.85 (s, 3H), 3.22 (m, 1H), 3.01 (m, 1H), 1.89 (m, 3H), 1.68 (m, 2H), 1.30 (m, 2H), 0.81 (d, 3H), 0.79 (d, 3H).

Preparation 123

(αS)-2-(4-Methoxyphenyl)-α-(2-methylpropyl)-2-oxo-1,3,2-oxazaphosphorinane-3-acetic acid (diastereomer 1, compound 323).

General procedure: 3.

Starting material: Compound 240.

$^{13}$C NMR (DMSO-d$_6$) δ 174.0, 161.8, 133.2, 122.5, 114.1, 67.3, 55.2, 55.2, 41.1, 38.1, 26.6, 24.1, 23.2, 21.4.

Preparation 124

(αS)-2-(4-Methoxyphenyl)-α-(2-methylpropyl)-2-oxo-1,3,2-oxazaphosphorinane-3-acetic acid (diastereomer 2, compound 324).

General procedure: 3.

Starting material: Compound 241.

$^{13}$C NMR (DMSO-d$_6$) δ 174.1, 163.1, 162.0, 133.4, 122.8, 114.0, 66.4, 55.4, 54.9, 40.3, 37.6, 25.8, 24.0, 22.8, 21.0.

Preparation 125

(±)-2-(4-Methoxyphenyl)-α-octyl-2-oxo-1,3,2-oxazaphosphorepane-3-acetic acid (diastereomers 1, compound 325).

General procedure: 3.

Starting material: Compound 242.

$^1$H NMR (CD$_3$OD) δ 7.72 (m, 2H), 6.98 (m, 2H), 4.62 (m, 1H), 4.18 (m, 1H), 4.13 (m, 1H), 3.83 (s, 3H), 3.21 (m, 1H), 3.11 (m, 1H), 2.00-1.20 (m, 18H), 0.90 (bt, 3H).

Preparation 126

(±)-2-(4-Methoxyphenyl)-α-octyl-2-oxo-1,3,2-oxazaphosphorepane-3-acetic acid (diastereomers 2, compound 326).

General procedure: 3.

Starting material: Compound 243.

$^1$H NMR(CD$_3$OD) δ 7.73 (m, 2H), 7.02 (m, 2H), 4.71 (m, 1H), 4.25 (m, 1H), 4.17 (m, 1H), 3.85 (s, 3H), 3.17 (m, 1H), 3.01 (m, 1H), 1.90 (m, 3H), 1.77 (m, 1H), 1.66 (m, 1H), 1.52 (m, 1H), 1.37-1.04 (m, 1OH), 0.96 (m, 2H), 0.88 (m, 3H).

Preparation 127

(αR)-2-(4-Methoxyphenyl)-2-oxo-α-phenylmethyl-1,3,2-oxazaphosphorinane-3-acetic acid (diastereomer 1, compound 327).

General procedure: 3

Starting material:Compound 246

$^{13}$C NMR (CD$_3$OD) δ 164.8, 139.2, 135.3, 130.9, 129.8, 128.0, 122.7, 115.5, 68.8, 56.3, 43.3, 37.9, 28.1.

Preparation 128

(αR)-2-(4-Methoxyphenyl)-2-oxo-α-phenylmethyl-1,3,2-oxazaphosphorinane-3-acetic acid (diastereomer 2, compound 328).

General procedure: 3

Starting material: Compound 247.

$^{13}$C NMR (CD$_3$OD) δ 179.5, 164.4, 140.2, 136.1, 130.4, 129.3, 127.2, 119.6, 114.9, 67.8, 63.0, 55.9, 42.1, 36.2, 27.4.

Preparation 129

(±)-2-(4-Methoxyphenyl)-2-oxo-α-propyl-1,3,2-oxazaphosphorinane-3-acetic acid (diastereomers 1, compound 329).

Compound 317 (0.18 mmol) was dissolved in methanol (4 ml), 10% Pd/C (25 mg) was added and the mixture was hydrogenated for 6 h, filtered through celite and concentrated under reduced pressure to afford compound 329.

$^1$H NMR (CD$_3$OD) δ 7.74 (m, 2H), 7.04 (m, 2H), 4.54 (m, 1H), 4.32 (m, 1H), 3.89 (m, 1H), 3.86 (s, 3H), 3.54 (m, 1H), 3.24 (m, IH), 2.22 (m, 1H), 2.08 (m, 1H), 1.74 (m, 1H), 1.63 (m, 1H), 1.17 (m, 1H), 1.00 (m, 1H), 0.72 (t, 3H).

Preparation 130

(±)-2-(4-Methoxyphenyl)-2-oxo-α-propyl-1,3,2-oxazaphosphorinane-3-acetic acid (diastereomers 2, compound 330).

Compound 318 (0.16 mmol) was dissolved in methanol (5 ml), 10% Pd/C (25 mg) was added and the mixture was hydrogenated for 5 h, filtered through celite and concentrated under reduced pressure to afford compound 330.

$^1$H NMR (CD$_3$OD) δ 7.80 (m, 2H), 7.02 (m, 2H), 4.40 (m, 1H), 4.20 (m, 1H), 4.04 (m, 1H), 3.84 (s, 3H), 3.39 (m, 2H), 2.14-1.40 (m, 6H), 0.99 (t, 3H).

Preparation 131

(±)-α-Allyl-2-(4-methoxyphenyl)-2-oxo-1,3,2-oxazaphosphorepane-3-acetic acid (diastereomer s1, compound 331).

General procedure: 3

Starting material: Compound 234.

$^1$H NMR (CD$_3$OD) δ 7.73 (m, 2H), 6.98 (m, 2H), 5.93 (m, 1H), 5.20 (m, 1H), 5.13 (m, 1H), 4.61 (m, 1H), 4.35 (m, 1H), 4.15 (m, 1H), 3.83 (s, 3H), 3.20 (m, 1H), 3.07 (m, 1H), 2.75 (m, 1H), 2.58 (m, 1H), 1.88 (m, 2H), 1.78 (m, 2H).

Preparation 132

(±)-α-Allyl-2-(4-methoxyphenyl)-2-oxo-1 3,2-oxazaphosphorepane-3-acetic acid (diastereomers 2, compound 332).

General procedure: 3

Starting material: Compound 235.

$^1$H NMR (CD$_3$OD) δ 7.72 (m, 2H), 7.00 (m, 2H), 5.50 (m, 1H), 4.92 (m, 1H), 4.77 (m, 1H), 4.23 (m, 1H), 4.11 (m, 1H), 3.84 (s, 3H), 3.25 (m, 1H), 2.95 (m, 2H), 2.52 (m, 1H), 2.24 (m, 1H), 2.06-1.72 (m, 3H), 1.62 (m, 1H).

Preparation 133

(±)-α-Allyl-2-oxo-2-(4-phenoxyphenyl)-1,3,2-oxazaphosphorinane-3-acetic acid (diastereomers 1, compound 333).

General procedure: 3

Starting material: Compound 250.

$^1$H NMR (CD$_3$OD) δ 7.82 (m, 2H), 7.41 (m, 2H), 7.20 (m, 1H), 7.06 (m, 2H), 7.03 (m, 2H), 5.95 (m, 1H), 5.21 (m, 1H), 5.13 (m, 1H), 4.41 (m, 1H), 4.23 (m, 2H), 3.39 (m, 2H), 2.72 (m, 1H), 2.62 (m, 1H), 2.08 (m, 1H), 1.92 (m, 1H).

Preparation 134

(±)-α-Allyl-2-oxo-2-(4-phenoxyphenyl)-1,3,2-oxazaphosphorinane-3-acetic acid (diastereomers 2, compound 334).

General procedure: 3

Starting material: Compound 252.

$^1$H NMR (CD$_3$OD) δ 7.77 (m, 2H), 7.42 (m, 2H), 7.21 (m, 1H), 7.06 (m, 4H), 5.48 (m, 1H), 5.03 (m, 1H), 4.89 (m, 1H), 4.54 (m, 1H), 4.32 (m, 1H), 4.10 (m, 1H), 3.49 (m, 1H), 3.28 (m, 1H), 2.59 (m, 1H), 2.45 (m, 1H), 2.23 (m, 1H), 2.04 (m, 1H).

Preparation 135

(±)-α-Butyl-2-oxo-2-(4-phenoxyphenyl)-1,3,2-oxazaphosphorepane-3-acetic acid (diastereomers 1, compound 335).

General procedure: 3

Starting material: Compound 253.

$^1$H NMR (CD$_3$OD) δ 7.77 (m, 2H), 7.41 (m, 2H), 7.20 (m, 1H), 7.04 (m, 4H), 4.74 (m, 1H), 4.26 (m, 1H), 4.17 (m, 1H), 3.40-2.90 (m, 2H), 2.00-0.84 (m, 10H), 0.77 (t, 3H).

Preparation 136

(±)-α-Butyl-2-oxo-2-(4-phenoxyphenyl)-1,3,2-oxazaphosphorepane-3-acetic acid (diastereomers 2, compound 336).

General procedure: 3

Starting material: Compound 254.

$^1$H NMR (CD$_3$OD) δ 7.81 (m, 2H), 7.39 (m, 2H), 7.18 (m, 1H), 7.03 (m, 2H), 6.98 (m, 2H), 4.65 (m, 1H), 4.15 (m, 1H), 3.97 (m, 1H), 3.35 (m, 1H), 310 (m, 1H), 2.06-1.60 (m, 6H), 1.40 (m, 4H), 0.91 (bt, 3H).

Preparation 137

(αR)-α-(2-Methylpropyl)-2-oxo-2-(4-phenoxyphenyl)-1,3,2-oxazaphosphorinane-3-acetic acid (diastereomer 1, compound 337).

General procedure: 3

Starting material: Compound 255.

$^1$H NMR (CD$_3$OD) δ 7.81 (m, 2H), 7.41 (m, 2H), 7.20 (m, 1H), 7.06 (m, 2H), 7.03 (m, 2H), 4.43 (m, 1H), 4.21 (m, 2H), 3.40 (m, 2H), 2.00 (m, 2H), 1.79 (m, 2H), 1.66 (m, 1H), 1.01 (d, 3H), 0.99 (d, 3H).

Preparation 138

(αR)-α-(2-Methylpropyl)-2-oxo-2-(4-phenoxyphenyl)-1,3,2-oxazaphosphorinane-3-acetic acid (diastereomer 2, compound 338).

General procedure: 3

Starting material: Compound 256.

$^1$H NMR (CD$_3$OD) δ 7.79 (m, 2H), 7.41 (m, 2H), 7.21 (m, 1H), 7.10-7.00 (m, 4H), 4.55 (m, 1H), 4.34 (m, 1H), 3.98 (m, 1H), 3.53 (m, 1H), 3.26 (m, 1H), 2.24 (m, 1H), 2.09 (m, 1H), 1.59 (m, 2H), 1.38 (m, 1H), 0.79 (d, 3H), 0.58 (d, 3H).

Preparation 139

(±)-α-Octyl-2-oxo-2-(4-phenoxyphenyl)-1,3,2-oxazaphosphorepane-3-acetic acid (diastereomers 1, compound 339).

General procedure: 3

Starting material: Compound 257.

$^1$H NMR (CD$_3$OD) δ 7.76 (m, 2H), 7.40 (m, 2H), 7.19 (m, 1H), 7.05 (m, 2H), 7.00 (m, 2H), 4.64 (dq, 1H), 4.17 (m, 2H), 3.15 (m, 2H), 2.02-1.25 (m, 18H), 0.90 (bt, 3H).

Preparation 140

(±)-α-Octyl-2-oxo-2-(4-phenoxyphenyl)-1,3,2-oxazaphosphorepane-3-acetic acid (diastereomers 2, compound 340).

General procedure: 3

Starting material: Compound 258.

MS. Calcd for C$_{26}$H$_{36}$NO$_5$P 473.23, Found [M+H]$^+$=474, [M−H]$^−$=472.

Preparation 141

(αR)-α-(2-Methylethyl)-2-oxo-2-(4-phenoxyphenyl)-1 3,2-oxazaphosphorinane-3-acetic acid (diastereomer 1, compound 341).

General procedure 3.

Starting material: Compound 259.

$^{13}$C NMR (CD$_3$OD) δ 175.4, 162.6, 157.1, 134.8, 131.2, 125.7, 125.5, 121.1, 118.7, 69.1, 65.7, 42.8, 28.4, 27.9, 20.1, 20.0.

Preparation 142

(αR)-α-(2-Methylethyl)-2-oxo-2-(4-phenoxyphenyl)-1,3, 2-oxazaphosphorinane-3-acetic acid (diastereomer 2, compound 342).

General procedure 3.

Starting material: Compound 294.

$^{13}$C NMR (CD$_3$OD) δ 178.6, 162.9, 156.9, 136.4, 131.3, 125.8, 124.3, 121.1, 118.2, 68.4, 67.3, 42.2, 27.3, 20.9, 19.6.

Preparation 143

(±)-2-(4-(4-Chlorophenoxy)-phenyl)-2-oxo-1,3,2-oxazaphosphorepane-3-acetic acid (compound 343).

General procedure 3.

Starting material: Compound 268.

$^{13}$C NMR (DMSO-d$_6$) δ 173.1, 158.9, 154.5, 133.3, 130.0, 128.0, 126.6, 121.1, 117.5, 64.5, 48.8, 46.6, 29.0, 25.7.

Preparation 144

(αR)-2-[4-(4-Chlorophenoxy)-phenyl]-α-(2-methylethyl)- 2-oxo-1,3,2-oxazaphosphorinane-3-acetic acid (diastereomer 1, compound 344).

General procedure 3.

Starting material: Compound 278

$^{13}$C NMR (CD$_3$OD) δ 175.4, 162.0, 156.0, 135.0, 131.2, 130.6, 126.2, 122.4, 119.0, 69.1, 65.7, 42.8, 28.3, 27.9, 20.1, 20.0.

Preparation 145

(αR)-α-(2-Methylethyl)-2-oxo-2-[4-(4-trifluoromethylphenoxy)-phenyl]-1,3,2-oxazaphosphorinane-3-acetic acid (diastereomer 1, compound 345).

General procedure 3.

Starting material: Compound 287

$^{13}$C NMR (CD$_3$OD) δ 174.8, 160.9, 160.8, 135.1, 128.6, 125.0, 120.4, 120.2, 69.2, 65.3, 42.7, 28.3, 27.8, 20.1, 19.9.

Preparation 146

(αR)-α-(2-Methylethyl)-2-oxo-2-[4-(4-trifluoromethylphenoxy)-phenyl]-1,3,2-oxazaphosphorinane-3-acetic acid (diastereomer 2, compound 346).

General procedure 3.

Starting material: Compound 288

MS. Calcd for C$_{21}$H$_{23}$F$_3$NO$_5$P 457.13, Found [M+H]= 458, [M−H]$^-$=456.

Preparation 147

(±)-2-[4-(4-Bromophenoxy)-phenyl]-2-oxo-1,3,2-oxazaphosphorinane-3-acetic acid (compound 347).

General procedure 3.

Starting material: Compound 289

$^{13}$C NMR (CD$_3$OD) δ 173.3, 162.3, 156.5, 135.3, 134.2, 125.6, 122.9, 119.1, 118.1, 69.1, 49.7, 48.5, 27.2.

Preparation 148

(±)-2-[4-(4-Bromophenoxy)-phenyl]-2-oxo-1 3,2-oxazaphosphorepane-3-acetic acid (compound 348).

General procedure 3.

Starting material: Compound 290

$^{13}$C NMR (CD$_3$OD) δ 176.9, 161.8, 156.7, 134.9, 134.2, 125.8, 122.8, 118.9, 117.9, 67.3, 50.8, 30.7, 27.9.

Preparation 149

(±)-2-(4-Nitrophenyl)-2-oxo-1,3,2-oxazaphosphorepane-3-acetic acid (compound 349).

General procedure 3.

Starting material: Compound 291.

$^1$H NMR (DMSO-d$_6$) δ 8.27 (m, 2H), 8.18 (m, 2H), 6.7 (bs, 1H), 4.43 (q, 1H), 4.11 (dd, 1H), 3.90 (dd, 1H), 3.60 (dd, 1H), 2.93 (m, 2H), 1.87-1.50 (m, 4H).

Preparation 150

(±)-2-[N-(4-Chlorobenzoyl)-4-aminophenyl]-2-oxo-1 3,2-oxazaphosphorepane-3-acetic acid (compound 350).

General procedure 3.

Starting material: Compound 292

$^1$H NMR (DMSO-d$_6$) δ 10.51 (bs, 1H), 8.00 (m, 2H), 7.85 (m, 4H), 7.62 (m, 2H), 4.37 (q, 1H), 4.03 (dd, 1H), 3.87 (dd, 1H), 3.59 (dd, 1H), 2.95 (m, 2H), 1.85-1.45 (m, 4H).

Preparation 151

(±)-2-(N-Benzoyl-4-aminophenyl)-2-oxo-1,3,2-oxazaphosphorepane-3-acetic acid (compound 351).

General procedure 3.

Starting material: Compound 293

$^{13}$C NMR (CD$_3$OD) δ 174.4, 169.0, 143.6, 136.1, 133.4, 133.1, 129.7, 128.7, 126.5, 121.3, 67.2, 30.7, 27.7.

Preparation 152

(±)-2-Phenyl-2-thioxo-1,3,2-oxazaphosphorinane-3-acetic acid (compound 352).

Preparation 153

(±)-2-Phenyl-2-thioxo-1,3,2-oxazaphosphorepane-3-acetic acid (compound 353).

General procedure 3.

Starting material: Compound 275.

$^{13}$C NMR (DMSO-d$_6$) δ 172.2, 135.4, 131.1, 130.0, 128.1, 64.4, 48.9, 47.5, 28.5, 25.0.

Example 1

(±)-2-(4-Chlorophenoxy)-2-oxo-1,3,2-oxazaphosphorinane-3-acetohydroxamic acid (compound 101).

General procedure 2.

Starting material: Compound 210.

$^{13}$C NMR (DMSO-d$_6$) δ 165.0, 149.5, 129.5, 128.5, 122.0, 70.2, 48.0, 47.6, 25.3.

Example 2

(±)-2-(4-Chlorophenoxy)-2-oxo-1,3,2-oxazaphosphorepane-3-acetohydroxamic acid (compound 102).

General procedure 2.

Starting material: Compound 211.

MS. Calcd for C$_{12}$H$_{16}$ClN$_2$O$_5$P 334.05, Found [M+H]$^+$= 335, [M+Na]$^+$=357.

Example 3

(±)-2-[(4-Bromophenyl)methyl]-2-oxo-1,3,2-oxazaphosphorinane-3-acetohydroxamic acid (compound 103).

General procedure 2.

Starting material: Compound 212.

$^1$H NMR (DMSO-d$_6$) δ 10.0-8.0 (bs, 2H), 7.47 (m, 2H), 7.27 (m, 2H), 4.21 (m, 2H), 3.70-2.90 (m, 6H), 1.92 (m, 1H), 1.49 (m 1H).

Example 4

(±)-2-[(4-Biphenylyl)methyl]-2-oxo-1,3,2-oxazaphosphorinane-3-acetohydroxamic acid (compound 104).

General procedure 2.

Starting material: Compound 213.

$^1$H NMR (DMSO-d$_6$) δ 11.0-8.0 (bs, 2H), 7.65 (m, 2H), 7.59 (m, 2H), 7.46 (m, 2H), 7.42-7.30 (m, 3H), 4.24 (m, 2H), 3.65-3.15 (m, 5H), 3.02 (m, 1H), 1.94 (m, 1H), 1.51 (m 1H).

Example 5

(±)-2-(4-Biphenylyl)-2-oxo-1,3,2-oxazaphosphorinane-3-acetohydroxamic acid (compound 105).

General procedure 2.

Starting material: Compound 214.

$^1$H NMR (DMSO-d$_6$) δ 11.0-9.8 (bs, 1H), 9.2-8.7 (bs, 1H), 7.87 (m, 1H), 7.80 (m, 3H), 7.72 (m, 2H), 7.51 (m, 2H), 7.42 (m, 1H), 4.36 (m, 1H), 4.13 (m, 1H), 3.58 (m, 2H), 3.40-3.10 (m, 2H), 2.07 (m, 1H), 1.86 (m, 1H).

Example 6

(±)-2-(4-Biphenylyl)-2-oxo-1,3,2-oxazaphosphorepane-3-acetohydroxamic acid (compound 106).

General procedure 2.

Starting material: Compound 215.

$^{13}$C NMR (DMSO-d$_6$) δ 166.8, 142.9, 139.4, 131.7, 130.2, 129.1, 128.1, 126.9, 126.5, 64.8, 46.5, 29.0, 25.9.

Example 7

(±)-2-Heptyl-2-oxo-1,3,2-oxazaphosphorinane-3-acetohydroxamic acid (compound 107).

General procedure 2.

Starting material: Compound 216.

$^1$H NMR (DMSO-d$_6$) δ 11.0-9.8 (bs, 1H), 9.1-8.6 (bs, 1H), 4.16 (m, 2H), 3.55 (dd, 1H), 3.40-3.15 (m, 2H), 2.98 (m, 1H), 2.05-1.60 (m, 4H), 1.55-1.12 (m, 10H), 0.87 (t, 3H).

Example 8

(±)-2-Heptyl-2-oxo-1,3,2-oxazaphosphorepane-3-acetohydroxamic acid (compound 108).

General procedure 2.

Starting material: Compound 217.

$^{13}$C NMR (DMSO-d$_6$) δ 166.9, 63.5, 46.6, 46.4, 31.0, 30.1, 28.9, 28.2, 26.1, 25.6, 22.1, 22.0, 13.8.

Example 9

(±)-2-Oxo-2-[4-(phenylamino)phenyl]-1,3,2-oxazaphosphorinane-3-acetohydroxamic acid (compound 109).

General procedure 2.

Starting material: Compound 218.

$^1$H NMR (DMSO-d$_6$) δ 11.0-9.8 (bs, 1H), 9.15-8.50 (m, 2H), 7.59 (m, 2H), 7.30 (m, 2H), 7.16 (m, 2H), 7.09 (m, 2H), 6.95 (m, 1H), 4.29 (m, 1H), 4.08 (m, 1H), 3.70-2.80 (m, 4H), 2.00 (m, 1H), 1.88 (m, 1H).

Example 10

(±)-2-Oxo-2-phenyl-1,3,2-oxazaphosphorinane-3-acetohydroxamic acid (compound 110).

General procedure 2.

Starting material: Compound 219.

$^1$H NMR (DMSO-d$_6$) δ 10.6-9.9 (bs, 1H), 9.1-8.7 (bs, 1H), 7.77 (m, 2H), 7.53 (m, 3H), 4.34 (m, 1H), 4.10 (m, 1H), 3.75-2.50 (m, 4H), 2.04 (m, 1H), 1.82 (m, 1H).

Example 11

(±)-2-Oxo-2-phenyl-1,3,2-oxazaphosphorepane-3-acetohydroxamic acid (compound 111).

General procedure 2.

Starting material: Compound 220.

$^{13}$C NMR (DMSO-d$_6$) δ 166.7, 131.5, 131.3, 131.0, 128.2, 64.7, 46.5, 46.4, 29.0, 25.9.

Example 12

2-Oxo-2-phenyl-1,3,2-oxazaphosphoronane-3-acetohydroxamic acid (compound 112).

General procedure 2.

Starting material: Compound 297.

$^1$H NMR (DMSO-d$_6$) δ 10.53 (bs, 1H), 8.91 (bs, 1H), 7.97 (m, 2H), 7.59-7.42 (m, 3H), 4.48 (m, 1H), 4.01 (dd, 1H), 3.88 (m, 1H), 3.42 (m, 1H), 2.89 (m, 1H), 2.62 (m, 1H), 1.90-1.60 (m, 2H), 1.58-1.05 (m, 6H).

Example 13

(±)-α-Butyl-2-oxo-2-phenyl-1,3,2-oxazaphosphorepane-3-acetohydroxamic acid (compound 113).

General procedure 1.

Starting material: Compound 307.

$^{13}$C NMR (DMSO-d$_6$) δ 168.1, 131.4, 131.1, 130.7, 128.1, 64.7, 55.0, 42.2, 31.2, 29.4, 28.7, 28.0, 21.9, 13.8.

Example 14

(±)-α-Butyl-2-oxo-2-phenyl-1,3,2-oxazaphosphorepane-3-acetohydroxamic acid (compound 114).

General procedure 1.

Starting material: Compound 308.

$^1$H NMR (DMSO-d$_6$) δ 10.60 (bs, 1H), 8.86 (bs, 1H), 7.72 (m, 2H), 7.56 (m, 1H), 7.49 (m, 2H), 4.34 (m, 1H), 4.11 (m, 1H), 3.94 (m, 1H), 2.84 (m, 1H), 1.86-1.49 (m, 5H), 1.26 (m, 1H), 1.09 (m, 2H), 0.85 (m, 2H), 0.67 (t, 3H).

Example 15

(±)-2-(4-Methoxyphenyl)-2-oxo-1,3,2-oxazaphosphorinane-3-acetohydroxamic acid (compound 115).

General procedure 2.

Starting material: Compound 223.

$^1$H NMR (DMSO-d$_6$) δ 11.0-8.0 (m, 2H), 7.71 (m, 2H), 7.04 (m, 2H), 4.30 (m, 1H), 4.06 (m, 1H), 3.82 (s, 3H), 3.46 (m, 2H), 3.21 (m, 2H), 2.01 (m, 1H), 1.85 (m, 1H).

Example 16

(±)-2-(4-Methoxyphenyl)-2-oxo-1,3,2-oxazaphosphorepane-3-acetohydroxamic acid (compound 116).

General procedure 2.

Starting material: Compound 224.

$^{13}$C NMR (DMSO-d$_6$) δ 166.7, 161.5, 132.8, 122.7, 113.6, 64.4, 55.1, 46.4, 46.3, 28.9, 25.8.

Example 17

(±)-2-(4-Methoxyphenyl)-2-oxo-1,3,2-oxazaphosphoronane-3-acetohydroxamic acid (compound 117).

General procedure 2.

Starting material: Compound 225.

$^{13}$C NMR (DMSO-d$_6$) δ 166.4, 161.6, 133.5, 122.4, 113.7, 59.6, 55.3, 44.0, 41.5, 27.3, 23.9, 18.5, 17.9.

Example 18

(αR)-2-(4-Methoxyphenyl)-α-(1-methylethyl)-2-oxo-1,3,2-oxazaphosphorinane-3-acetohydroxamic acid (diastereomer 1, compound 118).

General procedure 1.

Starting material: Compound 300.

$^1$H NMR (CD$_3$OD) δ 7.60 (m, 2H), 7.06 (m, 2H), 4.36 (m, 1H), 4.11 (m, 1H), 3.85 (s, 3H), 3.71 (m, 1H), 3.42 (m, 2H), 2.30 (m, 1H), 2.11 (m, 1H), 1.86 (m, 1H), 1.12 (d, 3H), 0.96-0.88 (d, 3H).

Example 19

(αR)-2-(4-Methoxyphenyl)-α-(1-methylethyl)-2-oxo-1,3,2-oxazaphosphorinane-3-acetohydroxamic acid (diastereomer 2, compound 119).

General procedure 1.

Starting material: Compound 301.

$^{13}$C NMR (DMSO-d$_6$) δ 167.9, 161.8, 133.6, 122.2, 113.7, 66.3, 60.4, 55.2, 25.7, 25.6, 19.3, 19.3.

Example 20

(±)-α-Butyl-2-(4-methoxyphenyl)-2-oxo-1,3,2-oxazaphosphorinane-3-acetohydroxamic acid (diastereomers 1, compound 120).

General procedure 1.

Starting material: Compound 311.

$^{13}$C NMR (DMSO-d$_6$) δ 168.0, 161.5, 132.8, 122.5, 114.1, 67.2, 55.2, 53.9, 41.2, 29.4, 27.6, 26.7, 21.7, 13.8.

Example 21

(±)-α-Butyl-2-(4-methoxyphenyl)-2-oxo-1,3,2-oxazaphosphorinane-3-acetohydroxamic acid (diastereomers 2, compound 121).

General procedure 1.

Starting material: Compound 312.

$^{13}$C NMR (CDCl$_3$) δ 168.7, 163.3, 134.6, 119.6, 114.0, 66.4, 55.4, 55.0, 40.5, 27.8, 26.6, 26.3, 22.1, 13.9.

Example 22

(±)-α-Butyl-2-(4-methoxyphenyl)-2-oxo-1,3,2-oxazaphosphorepane-3-acetohydroxamic acid (diastereomers 1, compound 122).

General procedure 1.

Starting material: Compound 313.

$^{13}$C NMR (DMSO-d$_6$) δ 168.2, 161.3, 132.6, 122.8, 113.6, 64.5, 55.1, 55.0, 42.1, 31.2, 29.4, 28.7, 28.0, 21.9, 13.9.

Example 23

(±)-α-Butyl-2-(4-methoxyphenyl)-2-oxo-1,3,2-oxazaphosphorepane-3-acetohydroxamic acid (diastereomers 2, compound 123).

General procedure 1.

Starting material: Compound 314.

$^{13}$C NMR (DMSO-d$_6$) δ 168.1, 161.6, 132.7, 122.7, 113.7, 64.9, 55.2, 54.2, 41.0, 28.8, 28.4, 27.8, 27.5, 21.6, 13.6.

Example 24

(±)-α-Butyl-2-(4-methoxyphenyl)-2-oxo-1,3,2-oxazaphosphorocane-3-acetohydroxamic acid (diastereomers 1, compound 124).

General procedure 1.

Starting material: Compound 315.

$^1$H NMR (DMSO-d$_6$) δ 10.77 (bs, 1H), 8.75 (bs, 1H), 7.59 (m, 2H), 6.99 (m, 2H), 4.26 (m, 1H), 3.94 (m, 2H), 3.80 (s, 3H), 3.53 (m, 1H), 2.82 (m, 1H), 1.93-1.40 (m, 8H), 1.27 (m, 2H), 1.17 (m, 2H), 0.84 (t, 3H).

Example 25

(±)-α-Butyl-2-(4-methoxyphenyl)-2-oxo-1,3,2-oxazaphosphorocane-3-acetohydroxamic acid (diastereomers 2, compound 125).

General procedure 1.

Starting material: Compound 316.

MS. Calcd for C$_{18}$H$_{29}$N$_2$O$_5$P 384.18, Found [M+H]$^+$= 385, [M−H]$^−$=383.

Example 26

(±)-α-Allyl-2-(4-methoxyphenyl)-2-oxo-1,3,2-oxazaphosphorinane-3-acetohydroxamic acid (diastereomers 1, compound 126).

General procedure 1.

Starting material: Compound 317.

$^{13}$C NMR (DMSO-d$_6$) δ 167.4, 161.6, 134.4, 132.8, 122.5, 117.4, 114.1, 67.1, 55.2, 53.6, 41.1, 34.2, 26.6.

Example 27

(±)-α-Allyl-2-(4-methoxyphenyl)-2-oxo-1,3,2-oxazaphosphorinane-3-acetohydroxamic acid (diastereomers 2, compound 127).

General procedure 1.

Starting material: Compound 318.

$^{13}$C NMR (DMSO-d$_6$) δ 167.6, 162.0, 134.5, 133.7, 121.6, 117.3, 113.9, 66.7, 55.2, 54.0, 32.8, 25.7.

Example 28

(±)-α-Allyl-2-(4-methoxyphenyl)-2-oxo-1,3,2-oxazaphosphorepane-3-acetohydroxamic acid (diastereomers 1, compound 128).

General procedure 1.

Starting material: Compound 331.

$^{13}$C NMR (DMSO-d$_6$) δ 167.5, 161.4, 134.6, 132.7, 122.7, 117.5, 113.7, 64.5, 55.1, 54.5, 42.0, 35.6, 29.0, 28.7.

Example 29

(±)-α-Allyl-2-(4-methoxyphenyl)-2-oxo-1,3,2-oxazaphosphorepane-3-acetohydroxamic acid (diastereomers 2, compound 129).

General procedure 1.

Starting material: Compound 332.

$^1$H NMR (DMSO-d$_6$) δ 10.54 (bs, 1H), 8.87 (bs, 1H), 7.64 (m, 2H), 7.03 (m, 2H), 5.39 (m, 1H), 4.94 (dd, 1H), 4.81 (dd, 1H), 4.33 (m, 1H), 4.05 (m, 2H), 3.81 (s, 3H), 2.81 (m, 1H), 2.39 (m, 1H), 2.07 (m, 1H), 1.76 (m, 2H), 1.57 (m, 2H).

Example 30

(αR)-2-(4-Methoxyphenyl)-α-(2-methylpropyl)-2-oxo-1,3,2-oxazaphosphorinane-3-acetohydroxamic acid (diastereomer 1, compound 130).

General procedure 1.

Starting material: Compound 319.

$^{13}$C NMR (DMSO-d$_6$) δ 168.0, 161.6, 132.8, 122.4, 114.1, 67.2, 55.2, 52.1, 41.1, 26.7, 24.0, 22.8, 21.9.

Example 31

(αR)-2-(4-Methoxyphenyl)-α-(2-methylpropyl)-2-oxo-1,3,2-oxazaphosphorinane-3-acetohydroxamic acid (diastereomer 2, compound 131).

General procedure 1.

Starting material: Compound 320.

$^{13}$C NMR (DMSO-d$_6$) δ 168.1, 162.0, 133.5, 121.9, 113.9, 66.5, 55.3, 52.0, 40.1, 37.3, 25.8, 23.7, 22.3, 21.8.

Example 32

(αS)-2-(4-Methoxyphenyl)-α-(2-methylpropyl)-2-oxo-1,3,2-oxazaphosphorinane-3-acetohydroxamic acid (diastereomer 1, compound 132).

General procedure 1.

Starting material: Compound 323.

$^{13}$C NMR (DMSO-d$_6$) δ 168.1, 161.5, 132.8, 122.5, 114.1, 67.2, 55.2, 52.1, 41.1, 26.8, 24.0, 22.8, 21.9.

Example 33

(αS)-2-(4-Methoxyphenyl)-α-(2-methylpropyl)-2-oxo-1,3,2-oxazaphosphorinane-3-acetohydroxamic acid (diastereomer 2, compound 133).

General procedure 1.

Starting material: Compound 324.

$^{13}$C NMR (DMSO-d$_6$) δ 168.1, 162.0, 133.5, 122.0, 113.9, 66.5, 55.3, 52.0, 40.1, 37.3, 25.8, 23.7, 22.3, 21.8.

Example 34

(±)-2-(4-Methoxyphenyl)-α-(2-methylpropyl)-2-oxo-1,3,2-oxazaphosphorepane-3-acetohydroxamic acid (diastereomers 1, compound 134).

General procedure 1.

Starting material: Compound 321.

$^{13}$C NMR (DMSO-d$_6$) δ 168.1, 161.3, 132.7, 122.7, 113.6, 64.5, 55.1, 53.2, 41.9, 40.5, 29.3, 28.7, 24.3, 22.5, 22.4.

Example 35

(±)-2-(4-Methoxyphenyl)-α-(2-methylpropyl)-2-oxo-1,3,2-oxazaphosphorepane-3-acetohydroxamic acid (diastereomers 2, compound 135).

General procedure 1.

Starting material: Compound 322.

$^1$H NMR (DMSO-d$_6$) δ 10.3 (bs, 1H), 8.85 (bs, 1H), 7.64 (m, 2H), 7.03 (m, 2H), 4.31 (m, 1H), 4.03 (m, 2H), 3.80 (s, 3H), 2.82 (m, 1H), 1.75 (m, 2H), 1.56 (m, 3H), 1.30-0.88 (m, 2H), 0.75 (d, 3H), 0.69 (d, 3H).

Example 36

(±)-2-(4-Methoxyphenyl)-α-propyl-2-oxo-1,3,2-oxazaphosphorinane-3-acetohydroxamic acid (diastereomers 1, compound 136).

General procedure 1.

Starting material: Compound 329.

$^1$H NMR (DMSO-d$_6$) δ 10.40 (bs, 1H), 8.85 (bs, 1H), 7.56 (m, 2H), 7.03 (m, 2H), 4.25 (m, 1H), 3.95 (m, 2H), 3.81 (s, 3H), 3.57 (m, 1H), 3.16 (m, 1H), 1.96-1.20 (m, 6H), 0.92 (t, 3H).

Example 37

(±)-2-(4-Methoxyphenyl)-α-propyl-2-oxo-1,3,2-oxazaphosphorinane-3-acetohydroxamic acid (diastereomers 2, compound 137).

General procedure 1.

Starting material: Compound 330.

$^1$H NMR (DMSO-d$_6$) δ 10.57 (bs, 1H), 8.86 (bs, 1H), 7.67 (m, 2H), 7.06 (m, 2H), 4.36-4.10 (m, 2H), 3.82 (s, 3H), 3.62 (m, 1H), 3.48 (m, 1H), 3.10 (m, 1H), 2.01 (m, 1H), 1.90 (m, 1H), 1.58 (m, 1H), 1.44 (m, 1H), 1.03 (m, 1H), 0.88 (m, 1H), 0.65 (t, 3H).

Example 38

(±)-2-(4-Methoxyphenyl)-α-octyl-2-oxo-1,3,2-oxazaphosphorepane-3-acetohydroxamic acid (diastereomers 1, compound 138).

General procedure 1.

Starting material: Compound 325.

$^{13}$C NMR (CDCl$_3$) δ 168.2, 161.3, 132.6, 122.8, 113.7, 64.5, 55.1, 42.3, 31.5, 31.2, 29.4, 28.9, 28.8, 28.5, 25.8, 22.0, 13.9.

Example 39

(±)-2-(4-Methoxyphenyl)-α-octyl-2-oxo-1,3,2-oxazaphosphorepane-3-acetohydroxamic acid (diastereomers 2, compound 139).

General procedure 1.

Starting material: Compound 326.

$^1$H NMR (DMSO-d$_6$) δ 10.55 (bs, 1H), 8.84 (bs, 1H), 7.64 (m, 2H), 7.02 (m, 2H), 4.31 (m, 1H), 4.07 (m, 1H), 3.91 (q, 1H), 3.80 (s, 3H), 3.22 (m, 1H), 2.84 (m, 1H), 1.85-0.93 (m, 18H), 0.84 (t, 3H).

Example 40

(αR)-2-(4-Methoxyphenyl)-2-oxo-α-phenylmethyl-1,3,2-oxazaphosphorinane-3-acetohydroxamic acid (diastereomer 1, compound 140).

General procedure 1.

Starting material: Compound 327

$^1$H NMR (CD$_3$OD) δ 7.64 (m, 2H), 7.32-7.15 (m, 5H), 7.04 (m, 2H), 4.21 (m, 2H), 4.10 (m, 1H), 3.84 (s, 3H), 3.83 (m, 1H), 3.43 (m, 1H), 3.31 (m, 1H), 3.06 (dd, 1H), 1.87 (m, 2H).

Example 41

(αS)-2-(4-Methoxyphenyl)-2-oxo-α-phenylmethyl-1,3,2-oxazaphosphorinane-3-acetohydroxamic acid (diastereomer 1, compound 141).

General procedures: 3 followed by 1

Starting material: Compound 244 (the intermediate carboxylic acid was not characterized).

$^1$H NMR (CD$_3$OD) δ 7.54 (m, 2H), 7.23-7.05 (m, 5H), 6.94 (m, 2H), 4.12 (m, 2H), 3.99 (m, 1H), 3.75 (s, 3H), 3.72 (m, 1H), 3.40-3.18 (m, 2H), 2.96 (dd, 1H), 1.79 (m, 2H).

Example 42

(αS)-2-(4-Methoxyphenyl)-2-oxo-α-phenylmethyl-1,3,2-oxazaphosphorinane-3-acetohydroxamic acid (diastereomer 2, compound 142).

General procedures: 3 followed by 1

Starting material: Compound 245 (the intermediate carboxylic acid was not characterized).

$^1$H NMR (DMSO-d$_6$) δ 10.55 (bs, 1H), 8.90 (bs, 1H), 7.23-7.16 (m, 3H), 7.10-6.94 (m, 4H), 6.78 (m, 2H), 4.27 (m, 1H), 4.05 (m, 2H), 3.78 (s, 3H), 3.63 (m, 1H), 3.12 (m, 1H), 2.90 (m, 2H), 2.06 (m, 1H), 1.75 (m, 1H).

Example 43

(±)-2-Oxo-2-(4-phenoxyphenyl)-1,3,2-oxazaphosphorinane-3-acetohydroxamic acid (compound 143).

General procedure 2.

Starting material: Compound 248.

$^1$H NMR (DMSO-d$_6$) δ 10.5-8.5 (m, 2H), 7.78 (m, 2H), 7.45 (m, 2H), 7.23 (m, 1H), 7.11 (m, 2H), 7.05 (m, 2H), 4.32 (m, 1H).

Example 44

(±)-2-Oxo-2-(4-phenoxyphenyl)-1,3,2-oxazaphosphorepane-3-acetohydroxamic acid (compound 144).

General procedure 2.

Starting material: Compound 249.

$^1$H NMR (DMSO-d$_6$) δ 11.0-10.1 (bs, 1H), 9.3-8.5 (bs, 1H), 7.82 (m, 2H), 7.44 (m, 2H), 7.22 (m, 1H), 7.10 (m, 2H), 7.03 (m, 2H), 4.35 (m, 1H), 4.05 (m, 1H), 3.82 (m, 1H), 3.54 (m, 1H), 2.91 (m, 2H), 1.88-1.43 (m, 4H).

Example 45

(±)-2-Oxo-2-(4-phenoxyphenyl)-1,3,2-oxazaphosphorocane-3-acetohydroxamic acid (compound 145).

General procedure 2.

Starting material: Compound 250.

$^1$H NMR (DMSO-d$_6$) δ 10.1 (bs, 1H), 8.89 (bs, 1H), 7.89 (m, 2H), 7.44 (m, 2H), 7.22 (m, 1H), 7.09 (m, 2H), 7.02 (m, 2H), 4.23 (m, 1H), 4.04-3.80 (m, 2H), 3.43 (m, 1H), 2.94 (m, 2H), 1.89-1.20 (m, 6H).

Example 46

(±)-α-Allyl-2-oxo-2-(4-phenoxyphenyl)-1,3,2-oxazaphosphorinane-3-acetohydroxamic acid (diastereomers 1, compound 146).

General procedure 1.

Starting material: Compound 333.

$^{13}$C NMR (DMSO-d$_6$) δ 167.6, 160.0, 155.2, 134.4, 134.0, 130.2, 124.7, 124.4, 119.6, 117.4, 117.4, 66.9, 54.0, 40.3, 32.9, 25.7.

Example 47

(±)-α-Allyl-2-oxo-2-(4-phenoxyphenyl)-1,3,2-oxazaphosphorinane-3-acetohydroxamic acid (diastereomers 2, compound 147).

General procedure 1.

Starting material: Compound 334.

$^1$H NMR (DMSO-d$_6$) δ 10.3 (bs, 1H), 9.2 (bs, 1H), 7.63 (m, 2H), 7.45 (m, 2H), 7.23 (m, 1H), 7.11 (m, 2H), 7.04 (m, 2H), 5.76 (m, 1H), 5.17 (m, 1H), 5.09 (m, 1H), 4.26 (m, 1H), 4.10 (m, 1H), 3.98 (m, 1H), 3.61 (m, 1H), 3.17 (m, 1H), 2.50 (m, 2H), 1.89 (m, 1H), 1.70 (m, 1H).

Example 48

(αR)-α-(2-Methylpropyl)-2-oxo-2-(4-phenoxyphenyl)-1,3,2-oxazaphosphorinane-3-acetohydroxamic acid (diastereomer 1, compound 148).

General procedure 1.

Starting material: Compound 337.

$^{13}$C NMR (DMSO-d$_6$) δ 168.0, 159.9, 155.3, 133.9, 130.2, 125.1, 124.4, 119.4, 117.6, 66.8, 52.0, 37.4, 25.9, 23.7, 22.3, 21.9.

Example 49

(αR)-α-(2-Methylpropyl)-2-oxo-2-(4-phenoxyphenyl)-1,3,2-oxazaphosphorinane-3-acetohydroxamic acid (diastereomer 2, compound 149).

General procedure 1.

Starting material: Compound 338.

$^{13}$C NMR (DMSO-d$_6$) δ 168.0, 159.6, 155.1, 133.1, 130.2, 125.4, 124.4, 119.7, 117.5, 67.4, 52.1, 41.0, 26.7, 24.0, 22.8, 21.9.

Example 50

(αR)-α-(2-Methylethyl)-2-oxo-2-(4-phenoxyphenyl)-1,3,2-oxazaphosphorinane-3-acetohydroxamic acid (diastereomer 1, compound 150).

General procedure: 1.

Starting material: Compound 341

$^1$H NMR (DMSO-d$_6$) δ 10.64/9.51 (s, 1H), 8.82/8.63 (s, 1H), 7.56 (m, 2H), 7.45 (m, 2H), 7.23 (m, 1H), 7.11 (m, 2H), 7.04 (m, 2H), 4.28 (m, 1H), 3.96 (m, 1H), 3.64 (m, 1H), 3.53 (t, 1H), 3.14 (m, 1H), 2.15 (m, 1H), 1.94 (m, 1H), 1.69 (m, 1H), 1.01 (d, 3H), 0.82 (d, 3H).

Example 51

(αR)-α-(2-Methylethyl)-2-oxo-2-(4-phenoxyphenyl)-1,3,2-oxazaphosphorinane-3-acetohydroxamic acid (diastereomer 2, compound 151).

General procedure: 1.

Starting material: Compound 342

$^1$H NMR (DMSO-d$_6$) δ 10.4 (bs, 1H), 8.87 (s, 1H), 7.76 (m, 2H), 7.45 (m, 2H), 7.23 (m, 1H), 7.13-7.01 (m, 4H), 4.28 (m, 2H), 3.56 (m, 1H), 3.16 (m, 1H), 3.08 (m, 1H), 2.19-1.74 (m, 3H), 0.72 (d, 3H), 0.50 (d, 3H).

Example 52

(±)-α-Butyl-2-oxo-2-(4-phenoxyphenyl)-1,3,2-oxazaphosphorepane-3-acetohydroxamic acid (diastereomers 1, compound 152).

General procedure: 1.

Starting material: Compound 335.

$^1$H NMR (DMSO-d$_6$) δ 10.66 (bs, 1H), 8.72 (bs, 1H), 7.67 (dd, 2H), 7.44 (bt, 2H), 7.22 (bt, 1H), 7.10 (bd, 2H), 6.99 (dd, 2H), 4.36 (q, 1H), 4.16-3.75 (m, 3H), 2.74 (m, 1H), 1.90-1.12 (m, 10H), 0.88 (t, 3H).

Example 53

(±)-α-Butyl-2-oxo-2-(4-phenoxyphenyl)-1,3,2-oxazaohosphorepane-3-acetohydroxamic acid (diastereomers 2, compound 153).

General procedure: 1.

Starting material: Compound 336.

$^1$H NMR (DMSO-d$_6$) δ 10.58 (bs, 1H), 8.86 (bs, 1H), 7.72 (m, 2H), 7.44 (m, 2H), 7.22 (m, 1H), 7.07 (m, 2H), 7.05 (m, 2H), 4.33 (m, 1H), 4.09 (m, 1H), 3.92 (q, 1H), 3.31 (m, 1H), 2.84 (m, 1H), 1.88-1.50 (m, 4H), 1.29 (m, 2H), 1.11 (m, 2H), 0.87 (m, 2H), 0.70 (t, 3H).

Example 54

(±)-α-Octyl-2-oxo-2-(4-phenoxyphenyl)-1,3,2-oxazaphosphorepane-3-acetohydroxamic acid (diastereomers 1, compound 154).

General procedure: 1.

Starting material: Compound 339.

MS. Calcd for $C_{26}H_{37}N_2O_5P$ 488.24, Found [M+H]$^+$= 489, [M−H]$^-$=487.

Example 55

(±)-α-Octyl-2-oxo-2-(4-phenoxyphenyl)-1,3,2-oxazaphosphorepane-3-acetohydroxamic acid (diastereomers 2, compound 155).

General procedure: 1.

Starting material: Compound 340.

$^1$H NMR (DMSO-d$_6$) δ 10.65 (bs, 1H), 8.71 (bs, 1H), 7.67 (m, 2H), 7.44 (m, 2H), 7.22 (m, 1H), 7.10 (m, 2H), 6.99 (dd, 2H), 4.36 (q, 1H), 4.17-3.75 (m, 3H), 2.75 (m, 1H), 1.89-1.10 (m, 18H), 0.87 (t, 3H).

Example 56

(±)-2-Oxo-2-(2-phenylethyl)-1,3,2-oxazaphosphorinane-3-acetohydroxamic acid (compound 156).

General procedure 2.

Starting material: Compound 260.

$^1$H NMR (DMSO-d$_6$) δ 11.0-9.2 (bs, 1H), 9.2-8.5 (bs, 1H), 7.28 (m, 4H), 7.19 (m, 1H), 4.21 (m, 2H), 3.63 (dd, 1H), 3.42-3.20 (m, 2H), 3.00 (m, 1H), 2.76 (m, 2H), 2.28-1.88 (m, 3H), 1.72 (m, 1H).

Example 57

(±)-2-(4-Methoxyphenyl)-2-oxo-1,3,2-oxazaphosphorocane-3-acetohydroxamic acid (compound 157).

General procedure 2.

Starting material: Compound 261.

$^{13}$C NMR (DMSO-d$_6$) δ 166.5, 161.6, 133.1, 123.0, 113.6, 65.3, 55.3, 44.7, 44.6, 28.1, 24.6, 24.1.

Example 58

(±)-2-Oxo-2-phenyl-1,3,2-oxazaphosphorocane-3-acetohydroxamic acid (compound 158).

General procedure 2.

Starting material: Compound 262.

$^{13}$C NMR (DMSO-d$_6$) δ 166.3, 131.7, 131.3, 131.1, 128.1, 65.5, 44.6, 44.5, 28.0, 24.5, 24.2.

Example 59

(±)-2-Heptyl-2-oxo-1,3,2-oxazaphosphorocane-3-acetohydroxamic acid (compound 159).

General procedure 2.

Starting material: Compound 263.

$^{13}$C NMR (DMSO-d$_6$) δ 166.5, 64.8, 44.5, 43.9, 31.0, 30.1, 28.2, 27.9, 26.2, 24.7, 24.1, 22.0, 22.0, 13.8.

Example 60

(αR)-2-(4-Biphenylyl)-α-(1-methylethyl)-2-oxo-1,3,2-oxazaphosphorinane-3-acetohydroxamic acid (diastereomer 2, compound 160).

General procedure 1.

Starting material: Compound 302.

MS. Calcd for $C_{20}H_{25}N_2O_4P$ 388.16, Found [M+H]$^+$= 389, [M+Na]$^+$=411.

Example 61

(±)-2-[4-(4-Chlorophenyloxy)-phenyl]-2-oxo-1,3,2-oxazaphosphorepane-3-acetohydroxamic acid (compound 161).

General procedure 2.

Starting material: Compound 268.

$^{13}$C NMR (DMSO-d$_6$) δ 166.6, 159.0, 154.4, 133.3, 130.0, 128.0, 126.1, 121.2, 117.5, 64.6, 46.4, 28.9, 25.8.

Example 62

(±)-2-[4-(4-Chlorophenyloxy)-phenyl]-2-oxo-1,3,2-oxazaphosphorocane-3-acetohydroxamic acid (compound 162).

General procedure 2.

Starting material: Compound 269.

$^{13}$C NMR (DMSO-d$_6$) δ 166.2, 159.0, 154.4, 133.4, 130.0, 128.0, 126.4, 121.1, 117.5, 65.5, 44.3, 27.9, 24.4, 24.0.

Example 63

(αR)-2-[4-(4-Chlorophenyloxy)-phenyl]-α-(2-methylethyl)-2-oxo-1,3,2-oxazaphosphorinane-3-acetohydroxamic acid (compound 163).

General procedure 1.

Starting material: Compound 344.

$^1$H NMR (DMSO-d$_6$) δ 10.64 (bs, 1H), 8.81 (s, 1H), 7.58 (m, 2H), 7.49 (m, 2H), 7.14 (m, 2H), 7.07 (m, 2H), 4.28 (m, 1H), 3.97 (m, 1H), 3.66 (m, 1H), 3.52 (m, 1H), 3.14 (m, 1H), 2.16 (m, 1H), 1.94 (m, 1H), 1.70 (m, 1H), 1.01 (d, 3H), 0.82 (d, 3H).

Example 64

(±)-2-(4'-Bromo-4-biphenylyl)-2-oxo-1,3,2-oxazaphosphorinane-3-acetohydroxamic acid (compound 164).

General procedure 2.

Starting material: Compound 270.

$^1$H NMR (DMSO-d$_6$) δ 10.4 (bs, 1H), 9.0 (bs, 1H), 7.93-7.74 (m, 4H), 7.69 (bs, 4H), 4.36 (m, 1H), 4.13 (m, 1H), 3.69-3.13 (m, 4H), 2.06 (m, 1H), 1.86 (m, 1H).

Example 65

(±)-2-(4'-Bromo-4-biphenylyl)-2-oxo-1,3,2-oxazaphosphorepane-3-acetohydroxamic acid (compound 165).

General procedure 2.

Starting material: Compound 271.

$^{13}$C NMR (DMSO-d$_6$) δ 166.6, 141.5, 138.4, 131.8, 131.7, 130.6, 128.9, 126.3, 121.6, 64.7, 46.4, 46.3, 28.9, 25.8.

Example 66

(±)-2-(4'-Bromo-4-biphenylyl)-2-oxo-1,3,2-oxazaphosphorocane-3-acetohydroxamic acid (compound 166).

General procedure 2.

Starting material: Compound 272.

MS. Calcd for $C_{19}H_{22}BrN_2O_4P$ 452.05, Found $[M-H]^- = $ 451.

Example 67

(±)-2-[2-(1-Naphtyl)-ethyl]-2-oxo-1,3,2-oxazaphosphorinane-3-acetohydroxamic acid (compound 167).

General procedure: 2.

Starting material: Compound 273

$^{13}$C NMR (CDCl$_3$) δ 166.9, 136.7, 133.9, 131.3, 129.0, 127.3, 126.3, 125.8, 125.7, 125.6, 123.2, 67.0, 49.6, 47.4, 27.3, 26.0, 25.8.

Example 68

(±)-2-Phenyl-2-thioxo-1,3,2-oxazaphosphorinane-3-acetohydroxamic acid (compound 168).

General procedure 2.

Starting material: Compound 274.

$^{13}$C NMR (DMSO-d$_6$) δ 165.2, 132.7, 132.2, 131.2, 128.5, 66.3, 49.4, 46.5, 25.5.

Example 69

(±)-2-Phenyl-2-thioxo-1,3,2-oxazaphosphorepane-3-acetamide (compound 169).

General procedure 2.

Starting material: Compound 275.

$^{13}$C NMR (DMSO-d$_6$) δ 166.5, 135.6, 130.9, 130.1, 128.0, 64.3, 47.3, 46.9, 28.4, 24.8.

Example 70

(±)-2-Phenyl-2-thioxo-1,3,2-oxazaphosphorocane-3-acetamide (compound 170).

General procedure 2.

Starting material: Compound 276.

$^{13}$C NMR (DMSO-d$_6$) δ 166.0, 136.0, 130.9, 130.4, 128.0, 65.5, 44.9, 44.4, 27.5, 24.1, 23.8.

Example 71

(±)-2-[4-(4-Chlorophenyloxy)-phenyl]-2-oxo-1,3,2-oxazaphosphorinane-3-acetohydroxamic acid (compound 171).

General procedure: 2

Starting material: Compound 277.

$^{13}$C NMR (DMSO-d$_6$) δ 165.7, 159.4, 154.2, 133.7, 130.0, 128.2, 125.7, 121.4, 117.7, 67.1, 47.9, 47.1, 25.4.

Example 72

(±)-2-(4-Bromophenyl)-2-oxo-1,3,2-oxazaphosphorinane-3-acetohydroxamic acid (compound 172).

General procedure 2.

Starting material: Compound 280.

$^1$H NMR (DMSO-d$_6$) δ 10.6-9.8 (bs, 1H), 9.2-8.7 (bs, 1H), 7.71 (m, 4H), 4.34 (m, 1H), 4.12 (m, 1H), 3.95-3.30 (m, 2H), 3.25 (m, 2H), 2.05 (m, 1H), 1.83 (m, 1H).

Example 73

(±)-2-(4-Bromophenyl)-2-oxo-1,3,2-oxazaphosphorepane-3-acetohydroxamic acid (compound 173).

General procedure 2.

Starting material: Compound 281.

$^{13}$C NMR (DMSO-d$_6$) δ 166.5, 133.0, 131.1, 130.7, 125.2, 64.8, 46.4, 46.3, 28.8, 25.8.

Example 74

(±)-2-Oxo-2-(4-phenylmethoxyphenyl)-1,3,2-oxazaphosphorinane-3-acetohydroxamic acid (compound 174).

General procedure 2.

Starting material: Compound 282.

$^1$H NMR (DMSO-d$_6$) δ 7.72 (m, 2H), 7.50-7.30 (m, 5H), 7.12 (m, 2H), 5.17 (s, 2H), 4.30 (m, 1H), 4.07 (m, 1H), 3.46 (m, 2H), 3.22 (m, 2H), 2.01 (m, 1H), 1.85 (m, 1H).

Example 75

(±)-2-Oxo-2-(4-phenylmethoxyphenyl)-1,3,2-oxazaphosphorepane-3-acetohydroxamic acid (compound 175).

General procedure 2.

Starting material: Compound 283.

$^{13}$C NMR (DMSO-d$_6$) δ 166.7, 160.5, 136.6, 132.8, 128.4, 127.8, 127.6, 123.0, 114.4, 69.2, 64.5, 46.3, 28.9, 25.7.

Example 76

(±)-2-Oxo-2-(4-phenylmethoxyphenyl)-1,3,2-oxazaphosphorocane-3-acetohydroxamic acid (compound 176).

General procedure 2.

Starting material: Compound 284.

$^{13}$C NMR (DMSO-d$_6$) δ 166.3, 160.5, 136.6, 133.0, 128.4, 127.8, 127.6, 123.2, 114.3, 69.1, 65.2, 44.4, 27.9, 24.5, 24.0.

Example 77

(±)-2-[2-(4-Chlorophenoxy)-phenyl]-2-oxo-1,3,2-oxazaphosphorepane-3-acetohydroxamic acid (compound 177).

Compound 177 was isolated as a by-product from the synthesis of compound 161 (example 61).

$^{13}$C NMR (DMSO-d$_6$) δ 166.9, 157.8, 155.7, 133.6, 133.3, 129.6, 127.2, 123.4, 122.9, 120.5, 119.2, 64.5, 47.3, 47.2, 28.8, 26.0.

Example 78

(±)-2-Oxo-2-[4-(4-trifluoromethylphenoxy)-phenyl]-1,3,2-oxazaphosphorinane-3-acetohydroxamic acid (compound 178).

General procedure 2.

Starting material: Compound 285.

$^{13}$C NMR (DMSO-d$_6$) δ 165.7, 159.0, 158.2, 133.8, 127.5, 126.9, 124.2, 124.1, 119.1, 118.9, 67.2, 47.9, 47.1, 25.4.

Example 79

(±)-2-Oxo-2-[4-(4-trifluoromethylphenoxy)-phenyl]-1,3,2-oxazaphosphorepane-3-acetohydroxamic acid (compound 179).

General procedure 2.

Starting material: Compound 286.

$^{13}$C NMR (DMSO-d$_6$) δ 166.6, 159.2, 157.8, 133.4, 127.5, 127.2, 124.1, 124.1, 118.9, 118.8, 64.7, 46.4, 28.9, 25.8.

Example 80

(αR)-α-(2-Methylethyl)-2-oxo-2-[4-(4-trifluoromethylphenoxy)-phenyl]-1,3,2-oxazaphosphorinane-3-acetohydroxamic acid (diastereomer 1, compound 180).

General procedure 1.

Starting material: Compound 287.

MS. Calcd for $C_{21}H_{24}F_3N_2O_5P$ 472.14, Found $[M+H]^+$=473, $[M-H]^-$=471.

Example 81

(αR)-α-(2-Methylethyl)-2-oxo-2-[4-(4-trifluoromethylphenoxy)-phenyl]-1,3,2-oxazaphosphorinane-3-acetohydroxamic acid (diastereomer 2, compound 181).

General procedure 1.

Starting material: Compound 288.

MS. Calcd for $C_{21}H_{24}F_3N_2O_5P$ 472.14, Found $[M+H]^+$=473, $[M-H]^-$=471.

Example 82

(±)-2-[4-(4-Bromophenoxy)-phenyl]-2-oxo-1,3,2-oxazaphosphorinane-3-acetohydroxamic acid (compound 182).

General procedure 2.

Starting material: Compound 289.

$^1$H NMR (DMSO-$d_6$) δ 10.1 (bs, 1H), 8.8 (bs, 1H), 7.79 (m, 2H), 7.61 (m, 2H), 7.13-7.05 (m, 4H), 4.33 (m, 1H), 4.11 (m, 1H), 3.49 (m, 2H), 3.25 (m, 2H), 2.04 (m, 1H), 1.85 (m, 1H).

Example 83

(±)-2-[4-(4-Bromophenoxy)-phenyl]-2-oxo-1,3,2-oxazaphosphorepane-3-acetohydroxamic acid (compound 183).

General procedure 2.

Starting material: Compound 290.

$^{13}$C NMR (DMSO-$d_6$) δ 166.6, 158.9, 154.9, 133.3, 132.9, 126.2, 121.5, 117.6, 116.0, 64.6, 46.4, 28.9, 25.8.

Example 84

(±)-2-(4-nitrophenyl)-2-oxo-1,3,2-oxazaphosphorepane-3-acetohydroxamic acid (compound 184).

General procedure 2.

Starting material: Compound 291.

$^1$H NMR (CDCl$_3$) δ 10.5 (bs, 1H), 8.9 (bs, 1H), 8.24 (m, 2H), 8.04 (m, 2H), 4.60 (m, 1H), 4.22 (dd, 1H), 3.83 (m, 2H), 3.07 (m, 2H), 1.78 (m, 4H).

Example 85

(±)-2-[N-(4-Chlorobenzoyl)-4-aminophenyl]-2-oxo-1,3,2-oxazaphosphorepane-3-acetohydroxamic acid (compound 185).

General procedure 2.

Starting material: Compound 292.

$^{13}$C NMR (DMSO-$d_6$) δ 166.7, 164.6, 141.6, 136.5, 133.3, 131.7, 129.6, 128.4, 126.1, 119.5, 64.6, 46.5, 46.3, 28.9, 25.8.

Example 86

(±)-2-(N-Benzoyl-4-aminophenyl-2-oxo-1,3,2-oxazaphosphorepane-3-acetohydroxamic acid (compound 186).

General procedure 2.

Starting material: Compound 293.

$^{13}$C NMR (DMSO-$d_6$) δ 166.7, 165.8, 141.8, 134.6, 131.7, 131.7, 128.3, 127.7, 125.8, 119.4, 64.5, 46.5, 46.3, 28.9, 25.8.

Example 87

Capsules containing compound 161.

Compound 161 was dissolved in fractionated coconut oil to a final concentration of 10 mg/ml. Ten parts by weight of gelatine, 5 parts by weight of glycerine, 0.08 parts by weight of potassium sorbate, and 14 parts by weight of distilled water were mixed together with heating and formed into soft gelatine capsules. These were then filled each with 500 µl of the oily solution of compound 161.

| Example 88: Tablet containing compound 161 | |
|---|---|
| Compound 161 (active substance) | 50 mg |
| Lactose | 125 mg |
| Starch | 12 mg |
| Methyl cellulose | 2 mg |
| Sodium carboxymethyl cellulose | 10 mg |
| Magnesium stearate | 1 mg |

The active substance, lactose and starch are mixed to a homogeneous state in a suitable mixer and moistened with a 5 percent aqueous solution of methyl cellulose 15 cps. The mixing is continued until granules are formed. If necessary, the wet granulation is passed through a suitable screen and dried to a water content of less than 1% in a suitable drier, e.g. fluid bed or drying oven. The dried granules are passed through a 1 mm screen and mixed to a homogeneous state with sodium carboxymethyl cellulose. Magnesium stearate is added, and the mixing is continued for a short period of time.

Tablets with a weight of 200 mg are produced from the granulation by means of a suitable tabletting machine.

| Example 89: Formulation for injection containing compound 161. | |
|---|---|
| Compound 161 (active substance) | 1% |
| Sodium chloride | q.s. |
| Ethanol | 10% |
| Water for injection to make | 100% |

The active substance is dissolved in ethanol (10%) then water for injection made isotonic with sodium chloride is added to make 100%. The mixture is filled into ampoules and sterilised.

What we claim is:
1. A compound of the general formula I

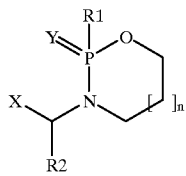

[I]

wherein Y is O or S;
n is 1, 2, 3 or 4;
X represents hydroxamic acid, carboxylic acid, phosphonic acid, acetylthiomethyl group or a mercaptomethyl group;
R1 is

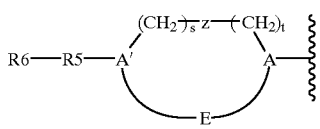

wherein E, when present represents, a bond or methylene or ethylene, optionally substituted with halogen, hydroxy, cyano, nitro, $(C_{1-6})$alkyl, haloalkyl, carboxy, amino, alkylamino, hydroxyalkyl, $(C_{1-6})$alkoxy or alkylcarbonyl;
s and t are independently 0, 1, 2 or 3;
A and A' independently represent a bond, or a saturated or unsaturated cyclic or heterocyclic hydrocarbon di- or triradical, optionally substituted with $(C_{1-6})$alkoxy, $(C_{1-6})$alkyl, phenyl, hydroxy, thio, $C_{1-6}$alkylthio, amino, halogen, cyano, cyanomethyl, trifluoromethyl, nitro, carboxy, —CONH$_2$, haloalkyl, alkylamino, hydroxyalkyl, alkylcarbonyl, —CONHR12 or —CONR12R12 wherein R12 is a $(C_{1-6})$alkyl group or the residue of a natural α-amino acid;
Z represents a bond, O, S, C(O), C(O)NR7, NR7C(O) or NR7, wherein R7 is hydrogen, hydroxy, branched or straight, saturated or unsaturated hydrocarbon radical, optionally substituted with halogen, hydroxy, cyano, nitro, haloalkyl carboxy, amino, alkylamino, hydroxyalkyl, alkoxy or alkylcarbonyl
R5 represents a bond, alkane or alkene diradical, one or more ether diradicals (R—O—R') or amine diradicals (R—N—R'), wherein R and R' independently represent alkane or alkene diradicals with a C-content from 0 to 3;
R6 represents hydrogen, hydroxy, halogen, cyano, nitro, branched or straight, saturated or unsaturated hydrocarbon radical, optionally substituted with halogen, hydroxy, cyano, nitro, haloalkyl, amino, alkylamino, carboxy, hydroxyalkyl, alkoxy or alkylcarbonyl; NR8R9, C(O)NR8R9, C(O)R8, C(O)OR8, S(O)$_2$R9, wherein each R8 and R9 independently represent hydrogen, halogen, a branched or straight, saturated or unsaturated hydrocarbon radical, optionally substituted with halogen, hydroxy, cyano, nitro, haloalkyl, hydroxyalkyl, alkoxy or alkylcarbonyl;

R2 represents hydrogen, $(C_{1-8})$alkyl, $(C_{2-6})$alkenyl, $(C_{3-8})$ cycloalkyl, aryl($C_{0-6}$)alkyl or heteroaryl($C_{0-6}$)alkyl;
provided that when A, A', Z and R5 are all bonds, and s and t are both 0 (zero), then R6 is not hydrogen;
or a salt, hydrate or solvate thereof.

2. A compound according to claim 1 wherein X is hydroxamic acid or carboxylic acid;
R1 is $(C_{1-12})$alkyl, phenyl($C_{0-6}$)alkyl, $(C_{1-6})$alkylphenyl, or phenoxy, or a group R10BR11 where B represents a bond, a divalent $(C_{1-6})$alkyl, oxygen, NH, sulphur or keto group, R10 and R11 independently represent a phenyl or pyrridyl group, any of which may be substututed with $(C_{1-6})$alkoxy, $(C_{1-6})$alkyl, phenyl, hydroxy, thio, $(C_{1-6})$alkylthio, amino, halogen, cyano, cyanomethyl, trifluoromethyl, nitro, carboxy, —CONH$_2$, CONHR12, or —CONR12R12, wherein R12 is a $(C_{1-6})$alkyl or the residue of a natural α-amino acid;
R2 is hydrogen, $(C_{1-6})$alkyl, $(C_{2-6})$alkenyl, $(C_{3-8})$ cycloalkyl, phenyl($C_{1-6}$)alkyl, heteroaryl($C_{0-6}$)alkyl;
Y is oxygen or sulphur;
n is 1,2 or 3;
or a salt, hydrate or solvate thereof.

3. A compound according to claim 1 or 2 wherein X represents CONHOH, Y represents oxygen and n=2.

4. A compound according to claim 1 wherein R1 is selected from the group consisting of alkoxyphenyl, phenoxyphenyl optionally substituted with halogen, halogen substituted hydrocarbon radical or cyano, phenylalkyl or naphtylalkyl both optionally substituted with halogen, phenyl optionally substituted with halogen or nitro, hydrocarbon radical, biphenyl optionally substituted with halogen, benzylphenoxyl, phenyl—(NH)—C(O)—phenyl optionally substituted with halogen or cyano, and methoxy.

5. A compound according to claim 4 wherein R1 is selected from the group consisting of 4-methoxyphenyl, 4-(4-chloro-phenoxy)-phenyl, 4-(4-bromophenoxy)-phenyl, 4-(4-trifluoromethylphenoxy)-phenyl, 4'bromo-4-biphenylyl, N-(4-chlorbenzoyl)-4-aminophenyl, 4-nitrophenyl, N-benzoyl-4-aminophenyl and 4-phenoxyphenyl.

6. A compound according to claim 1 wherein R2 is selected from the group consisting of hydrogen, $(C_{1-8})$alkyl, $(C_{2-6})$alkenyl and aryl($C_{0-6}$)alkyl.

7. A compound according to claim 6 wherein R2 is selected from the group consisting of hydrogen, isopropyl, allyl, isobutyl, n-butyl, n-octyl and benzyl.

8. A compound according to claim 1 which is selected form the group consisting of:
(±)-2-(4-Chlorophenoxy)-2-oxo-1,3,2-oxazaphosphorinane-3-acetohydroxamic acid,
(±)-2-(4-Chlorophenoxy)-2-oxo-1,3,2-oxazaphosphorepane-3-acetohydroxamic acid,
(±)-2-[(4-Bromophenyl)methyl]-2-oxo-1,3,2-oxazaphosphorinane-3-acetohydroxamic acid,
(±)-2-[(4-Biphenylyl)methyl]-2-oxo- 1,3,2-oxazaphosphorinane-3-acetohydroxamic acid,
(±)-2-(4-Biphenylyl)-2-oxo-1,3,2-oxazaphosphorinane-3-acetohydroxamic acid,
(±)-2-(4-Biphenylyl)-2-oxo-1,3,2-oxazaphosphorepane-3-acetohydroxamic acid,
(±)-2-Heptyl-2-oxo-1,3,2-oxazaphosphorinane-3-acetohydroxamic,
(±)-2-Heptyl-2-oxo-1,3,2-oxazaphosphorepane-3-acetohydroxamic acid, (±)-2-Oxo-2-[4-(phenylamino)phenyl]-1,3,2-oxazaphosphorinane-3-acetohydroxamic acid, (±)-2-Oxo-2-phenyl-1,3,2-oxazaphosphorinane-3-acetohydroxamic acid, (±)-2-Oxo-2-phenyl-1,3,2-oxazaphosphorepane-3-acetohydroxamic acid, (±)-2-Oxo-2-phenyl-1,3,2-oxazaphosphoronane-3-acetohydroxamic acid (±)-α-Butyl-2-oxo-2-phenyl-1,3,2-oxazaphosphorepane-3-acetohydroxamic acid, (±)-α-Butyl-2-oxo-2-phenyl-1,3,2-oxazaphosphorepane-3-acetohydroxamic acid, (±)-2-(4-Methoxyphenyl)-2-oxo-1,3,2-oxazaphosphorinane-3-acetohydroxamic acid, (±)-2-(4-Methoxyphenyl)-2-oxo-1,3,2-oxazaphosphorepane-3-acetohydroxamic acid, (±)-2-(4-Methoxyphenyl)-2-oxo-1,3,2-oxazaphosphoronane-3-acetohydroxamic acid, (αR)-2-(4-Methoxyphenyl)-α-(1-methylethyl)-2-oxo-1,3,2-oxazaphosphorinane-3-acetohydroxamic acid (diastereomer 1), (αR)-2-(4-Methoxyphenyl)-α-(1-methylethyl)-2-oxo-1,3,2-oxazaphosphorinane-3-acetohydroxamic acid (diastereomer 2), (±)-α-Butyl-2-(4-methoxyphenyl)-2-oxo-1,3,2-oxazaphosphorinane-3-acetohydroxamic acid (diastereomers 1), (±)-α-Butyl-2-(4-methoxyphenyl)-2-oxo-1,3,2-oxazaphosphorinane-3-acetohydroxamic acid (diastereomers 2), (±)-α-Butyl-2-(4-methoxyphenyl)-2-oxo-1,3,2-oxazaphosphorepane-3-acetohydroxamic acid (diastereomers 1), (±)-α-Butyl-2-(4-methoxyphenyl)-2-oxo-1,3,2-oxazaphosphorepane-3-acetohydroxamic acid (diastereomers 2), (±)-α-Butyl-2-(4-methoxyphenyl)-2-oxo-1,3,2-oxazaphosphorocane-3-acetohydroxamic acid (diastereomers 1), (±)-α-Butyl-2-(4-methoxyphenyl)-2-oxo-1,3,2-oxazaphosphorocane-3-acetohydroxamic acid (diastereomers 2), (±)-α-Allyl-2-(4-methoxyphenyl)-2-oxo-1,3,2-oxazaphosphorinane-3-acetohydroxamic acid (diastereomers 1), (±)-α-Allyl-2-(4-methoxyphenyl)-2-oxo-1,3,2-oxazaphosphorinane-3-acetohydroxamic acid (diastereomers 2,), (±)-α-Allyl-2-(4-methoxyphenyl)-2-oxo-1,3,2-oxazaphosphorepane-3-acetohydroxamic acid (diastereomers 1,), (±)-α-Allyl-2-(4-methoxyphenyl)-2-oxo-1,3,2-oxazaphosphorepane-3-acetohydroxamic acid (diastereomers 2), (αR)-2-(4-Methoxyphenyl)-α-(2-methylpropyl)-2-oxo-1,3,2-oxazaphosphorinane-3-acetohydroxamic acid (diastereomer 1, compound 130), (αR)-2-(4-Methoxyphenyl)-α-(2-methylpropyl)-2-oxo-1,3,2-oxazaphosphorinane-3-acetohydroxamic acid (diastereomer 2), (αS)-2-(4-Methoxyphenyl)-α-(2-methylpropyl)-2-oxo-1,3,2-oxazaphosphorinane-3-acetohydroxamic acid (diastereomer 1), (αS)-2-(4-Methoxyphenyl)-α-(2-methylpropyl)-2-oxo-1,3,2-oxazaphosphorinane-3-acetohydroxamic acid (diastereomer 2), (±)-2-(4-Methoxyphenyl)-α-(2-methylpropyl)-2-oxo-1,3,2-oxazaphosphorepane-3-acetohydroxamic acid (diastereomers 1), (±)-2-(4-Methoxyphenyl)-α-(2-methylpropyl)-2-oxo-1,3,2-oxazaphosphorepane-3-acetohydroxamic acid (diastereomers 2), (±)-2-(4-Methoxyphenyl)-α-propyl-2-oxo-1,3,2-oxazaphosphorinane-3-acetohydroxamic acid (diastereomers 1), (±)-2-(4-Methoxyphenyl)-α-propyl-2-oxo-1,3,2-oxazaphosphorinane-3-acetohydroxamic acid (diastereomers 2,), (±)-2-(4-Methoxyphenyl)-α-octyl-2-oxo-1,3,2-oxazaphosphorepane-3-acetohydroxamic acid (diastereomers 1), (±)-2-(4-Methoxyphenyl)-α-octyl-2-oxo-1,3,2-oxazaphosphorepane-3-acetohydroxamic acid (diastereomers 2,), (αR)-2-(4-Methoxyphenyl)-2-oxo-α-phenylmethyl-1,3,2-oxazaphosphorinane-3-acetohydroxamic acid (diastereomer 1), (αS)-2-(4-Methoxyphenyl)-2-oxo-α-phenylmethyl-1,3,2-oxazaphosphorinane-3-acetohydroxamic acid (diastereomer 1), (αS)-2-(4-Methoxyphenyl)-2-oxo-α-phenylmethyl-1,3,2-oxazaphosphorinane-3-acetohydroxamic acid (diastereomer 2), (±)-2-Oxo-2-(4-phenoxyphenyl)-1,3,2-oxazaphosphorinane-3-acetohydroxamic acid, (±)-2-Oxo-2-(4-phenoxyphenyl)-1,3,2-oxazaphosphorepane-3-acetohydroxamic acid, (±)-2-Oxo-2-(4-phenoxyphenyl)-1,3,2-oxazaphosphorocane-3-acetohydroxamic acid, (±)-α-Allyl-2-oxo-2-(4-phenoxyphenyl)-1,3,2-oxazaphosphorinane-3-acetohydroxamic acid (diastereomers 1.), (±)-α-Allyl-2-oxo-2-(4-phenoxyphenyl)-1,3,2-oxazaphosphorinane-3-acetohydroxamic acid (diastereomers 2), (αR)-α-(2-Methylpropyl)-2-oxo-2-(4-phenoxyphenyl)-1,3,2-oxazaphosphorinane-3-acetohydroxamic acid (diastereomer 1), (αR)-α-(2-Methylpropyl)-2-oxo-2-(4-phenoxyphenyl)-1,3,2-oxazaphosphorinane-3-acetohydroxamic acid (diastereomer 2), (αR)-α-(2-Methylethyl)-2-oxo-2-(4-phenoxyphenyl)-1,3,2-oxazaphosphorinane-3-acetohydroxamic acid (diastereomer 1), (αR)-α-(2-Methylethyl)-2-oxo-2-(4-phenoxyphenyl)-1,3,2-oxazaphosphorinane-3-acetohydroxamic acid (diastereomer 2), (±)-α-Butyl-2-oxo-2-(4-phenoxyphenyl)-1,3,2-oxazaphosphorepane-3-acetohydroxamic acid (diastereomers 1), (±)-α-Butyl-2-oxo-2-(4-phenoxyphenyl)-1,3,2-oxazaphosphorepane-3-acetohydroxamic acid (diastereomers 2), ±)-α-Octyl-2-oxo-2-(4-phenoxyphenyl)-1,3,2-oxazaphosphorepane-3-acetohydroxamic acid (diastereomers 1), (±)-α-Octyl-2-oxo-2-(4-phenoxyphenyl)-1,3,2-oxazaphosphorepane-3-acetohydroxamic acid (diastereomers 2), (±)-2-Oxo-2-(2-phenylethyl)-1,3,2-oxazaphosphorinane-3-acetohydroxamic acid, (±)-2-(4-Methoxyphenyl)-2-oxo-1,3,2-oxazaphosphorocane-3-acetohydroxamic acid, (±)-2-Oxo-2-phenyl-1,3,2-oxazaphosphorocane-3-acetohydroxamic acid, (±)-2-Heptyl-2-oxo-1,3,2-oxazaphosphorocane-3-acetohydroxamic acid, (compound 159), (αR)-2-(4-Biphenylyl)-α-(1-methylethyl)-2-oxo-1,3,2-oxazaphosphorinane-3-acetohydroxamic acid (diastereomer 2), (±)-2-[4-(4-Chlorophenyloxy)-phenyl]-2-oxo-1,3,2-oxazaphosphorepane-3-acetohydroxamic acid, (±)-2-[4-(4-Chlorophenyloxy)-phenyl]-2-oxo-1,3,2-oxazaphosphorocane-3-acetohydroxamic acid, (αR)-2-[4-(4-Chlorophenyloxy)-phenyl]-α-(2-methylethyl)-2-oxo-1,3,2-oxazaphosphorinane-3-acetohydroxamic acid, (±)-2-(4'-Bromo-4-biphenylyl)-2-oxo-1,3,2-oxazaphosphorinane-3-acetohydroxamic acid, (±)-2-(4'-Bromo-4-biphenylyl)-2-oxo-1,3,2-oxazaphosphorepane-3-acetohydroxamic acid, (±)-2-(4'-Bromo-4-biphenylyl)-2-oxo-1,3,2-oxazaphosphorocane-3-acetohydroxamic acid, (±)- 2-[2-(1-Naphtyl)-ethyl]-2-oxo-1,3,2-oxazaphosphorinane-3-acetohydroxamic acid, (±)-2-Phenyl-2-thioxo-1,3,2-oxazaphosphorinane-3-acetohydroxamic acid, (±)-2-Phenyl-2-thioxo-1,3,2-oxazaphosphorepane-3-acetamide, (±)-2-Phenyl-2-thioxo-1,3,2-oxazaphosphorocane-3-acetamide, (±)-2-[4-(4-Chlorophenyloxy)-phenyl]-2-oxo-1,3,2-oxazaphosphorinane-3-acetohydroxamic acid, (±)-2-(4-Bromophenyl)-2-oxo-1,3,2-oxazaphosphorinane-3-acetohydroxamic acid, (±)-2-(4-Bromophenyl)-2-oxo-1,3,2-oxazaphosphorepane-3-acetohydroxamic acid, (±)-2-Oxo-2-(4-phenylmethoxyphenyl)-1,3,2-oxazaphosphorinane-3-acetohydroxamic acid, (±)-2-Oxo-2-(4-phenylmethoxyphenyl)-1,3,2-oxazaphosphorepane-3-acetohydroxamic acid, (±)-2-Oxo-2-(4-phenylmethoxyphenyl)-1,3,2-oxazaphosphorocane-3-acetohydroxamic acid, (±)-2-[2-(4-Chlorophenoxy)-phenyl ]-2-oxo-1,3,2-oxazaphosphorepane-3-acetohydroxamic acid, (±)-2-Oxo-2-[4-(4-trifluoromethylphenoxy)-phenyl]-1,3,2-oxazaphosphorinane-3-acetohydroxamic acid, (±)-2-Oxo-2-[4-(4-trifluoromethylphenoxy)-phenyl]-1,3,2-oxazaphosphorepane-3-acetohydroxamic acid, (αR)-α-(2-Methylethyl)-2-oxo-2-[4-(4-trifluoromethylphenoxy)-phenyl]-1,3,2-oxazaphosphorinane-3-acetohydroxamic acid (diastereomer 1,), (αR)-α-(2-Methylethyl)-2-oxo-2-[4-(4-trifluoromethylphenoxy)-phenyl]-1,3,2-oxazaphosphorinane-3-acetohydroxamic acid (diastereomer 2), (±)-2-[4-(4-Bromophenoxy)-phenyl]-2-oxo-1,3,2-oxazaphosphorinane-3-acetohydroxamic acid, (±)-2-[4-(4-Bromophenoxy)-phenyl]-2-oxo-1,3,2-oxazaphosphorepane-3-acetohydroxamic acid, (±)-2-(4-nitrophenyl)-2-oxo-1,3,2-oxazaphosphorepane-3-acetohydroxamic acid, (±)-2-[N-(4-Chlorobenzoyl)-4-aminophenyl]-2-oxo-1,3,2-oxazaphosphorepane-3-acetohydroxamic acid, (±)-2-(N-Benzoyl-4-aminophenyl-2-oxo-1,3,2-oxazaphosphorepane-3-acetohydroxamic acid;

and the corresponding carboxylic acids.

9. An isomer of a compound according to claim 1, in pure form, or a mixture of isomers of said compounds.

10. A pharmaceutical composition containing an effective amount of one or more of the compounds of claim 1 as an active ingredient, together with pharmaceutically acceptable carriers and/or auxiliary agents.

11. A method for the treatment or prophylaxis of diseases or conditions involving tissue breakdown, inflammation comprising or proliferative disorder comprising administering to a patient in need thereof an effective amount of a compound according to claim 1.

12. A method according to claim 11 wherein the disease or condition is arthritis, rheumatoid arthritis, osteoarthritis, osteopenias, oteroporosis, periodontitis, gingivitis, corneal epidermal or gastric ulceration, skin agning, tumour metastasis, invasion or growth, multiple sclerosis, psoriasis, proliferative retinopathies, neovascular glaucoma, ocular tumours angiofibroma or hemangiomas.

* * * * *